(12) United States Patent
Tuna et al.

(10) Patent No.: US 11,629,193 B2
(45) Date of Patent: Apr. 18, 2023

(54) EGFR BINDING MOLECULES

(71) Applicant: F-STAR BETA LIMITED, Cambridge (GB)

(72) Inventors: Mihriban Tuna, Cambridge (GB); Kin-Mei Leung, Cambridge (GB); Haijun Sun, Cambridge (GB); Melanie Medcalf, Cambridge (GB); Samine Isaac, Cambridge (GB)

(73) Assignee: F-star Therapeutics Limited, Cambridge (GB)

( * ) Notice: Subject to any disclaimer, the term of this patent is extended or adjusted under 35 U.S.C. 154(b) by 383 days.

(21) Appl. No.: 16/319,235

(22) PCT Filed: Jul. 19, 2017

(86) PCT No.: PCT/EP2017/068261
§ 371 (c)(1),
(2) Date: Jan. 18, 2019

(87) PCT Pub. No.: WO2018/015448
PCT Pub. Date: Jan. 25, 2018

(65) Prior Publication Data
US 2019/0202920 A1  Jul. 4, 2019

(30) Foreign Application Priority Data

Jul. 19, 2016  (GB) .................................. 1612520

(51) Int. Cl.
| | | |
|---|---|---|
| *C07K 16/22* | (2006.01) | |
| *C07K 16/28* | (2006.01) | |
| *A61K 39/395* | (2006.01) | |
| *A61K 31/517* | (2006.01) | |
| *A61K 47/68* | (2017.01) | |
| *A61P 11/00* | (2006.01) | |
| *A61P 35/00* | (2006.01) | |
| *C07K 16/46* | (2006.01) | |
| *A61K 39/00* | (2006.01) | |

(52) U.S. Cl.
CPC ........ *C07K 16/2863* (2013.01); *A61K 31/517* (2013.01); *A61K 39/39558* (2013.01); *A61K 47/6813* (2017.08); *A61K 47/6845* (2017.08); *A61P 11/00* (2018.01); *A61P 35/00* (2018.01); *C07K 16/22* (2013.01); *C07K 16/2818* (2013.01); *C07K 16/468* (2013.01); *A61K 2039/505* (2013.01); *A61K 2039/507* (2013.01); *C07K 2317/31* (2013.01); *C07K 2317/33* (2013.01); *C07K 2317/524* (2013.01); *C07K 2317/526* (2013.01); *C07K 2317/53* (2013.01); *C07K 2317/56* (2013.01); *C07K 2317/565* (2013.01); *C07K 2317/73* (2013.01); *C07K 2317/732* (2013.01); *C07K 2317/76* (2013.01); *C07K 2317/77* (2013.01); *C07K 2317/92* (2013.01); *C07K 2317/94* (2013.01); *C07K 2318/20* (2013.01)

(58) Field of Classification Search
CPC ... C07K 16/22; C07K 16/468; C07K 16/2863
USPC ........................................................ 424/133.1
See application file for complete search history.

(56) References Cited

U.S. PATENT DOCUMENTS

| | | | |
|---|---|---|---|
| 7,288,638 B2 | 10/2007 | Jure-Kunkel et al. | |
| 7,592,426 B2 | 9/2009 | Ebel et al. | |
| 8,217,149 B2 | 7/2012 | Irving et al. | |
| 8,383,796 B2 | 2/2013 | Korman et al. | |
| 8,911,732 B2 | 12/2014 | Dennis et al. | |
| 9,567,399 B1 | 2/2017 | Campbell et al. | |
| 9,617,338 B1 | 4/2017 | Campbell et al. | |
| 10,233,258 B2 | 3/2019 | Akamatsu et al. | |
| 11,214,618 B2 | 1/2022 | Tuna et al. | |
| 11,214,620 B2 | 1/2022 | Campbell et al. | |
| 2009/0055944 A1 | 2/2009 | Korman et al. | |
| 2012/0237498 A1 | 9/2012 | Ahrens et al. | |
| 2012/0276104 A1 | 11/2012 | Woisetschlager | |
| 2013/0034559 A1 | 2/2013 | Queva et al. | |
| 2014/0004121 A1 | 1/2014 | Fanslow, III et al. | |
| 2014/0341917 A1 | 11/2014 | Nastri et al. | |
| 2015/0259420 A1 | 9/2015 | Triebel et al. | |
| 2016/0137740 A1 | 5/2016 | Hammond et al. | |
| 2016/0244528 A1 | 8/2016 | Gray et al. | |
| 2017/0198050 A1 | 7/2017 | Eckelman et al. | |

(Continued)

FOREIGN PATENT DOCUMENTS

| | | |
|---|---|---|
| EP | 2407487 A1 | 1/2012 |
| EP | 2546268 A1 | 1/2013 |

(Continued)

OTHER PUBLICATIONS

Levitan (www.cancernetwork.com/view/amgen-halts-rilotumumab-development-due-increased-death-signal pp. 1-3 (Nov. 26, 2014)).*
Search Report under Section 17(5) dated May 2, 2017 by the UK's Intellectual Property Office for GB Application No. 1612520.5 (3 pages).
[No Author Listed] F-star Alpha: a new asset centric company. Retrieved from http://www.onenucleus.com/media/Events/LSLS/11%20feb%202014/Jane%20Dancer.pdf on Jan. 8, 2015. 15 pages.
Asgarov et al., a new anti-mesothelin antibody targets selectively the membrane-associated form. MAbs. Apr. 2017;9(3):567-577. doi: 10.1080/19420862.2017.1288770.

(Continued)

*Primary Examiner* — Lynn A Bristol
(74) *Attorney, Agent, or Firm* — Wolf, Greenfield & Sacks, P.C.

(57) ABSTRACT

The application relates to specific binding members which bind the human epidermal growth factor receptor (EGFR). The specific binding members preferably comprise an EGFR antigen-binding site which may be located in two or more structural loops of a CH3 domain of the specific binding member. The specific binding members are expected to find application in the treatment of cancers expressing EGFR.

20 Claims, 19 Drawing Sheets

Specification includes a Sequence Listing.

(56) References Cited

U.S. PATENT DOCUMENTS

| | | |
|---|---|---|
| 2018/0194862 A1 | 7/2018 | Akamatsu et al. |
| 2018/0339031 A1 | 11/2018 | Masternak et al. |
| 2019/0106494 A1 | 4/2019 | Wang et al. |
| 2019/0256602 A1 | 8/2019 | Campbell et al. |
| 2019/0330344 A1 | 10/2019 | Tuna et al. |
| 2019/0338049 A1* | 11/2019 | Tuna .................. C07K 16/3069 |
| 2020/0407446 A1 | 12/2020 | McCourt et al. |
| 2021/0139590 A1 | 5/2021 | Tuna et al. |
| 2021/0237498 A1 | 8/2021 | Yoda et al. |
| 2021/0238299 A1 | 8/2021 | Pechouckova et al. |
| 2021/0277134 A1 | 9/2021 | Lakins et al. |
| 2021/0301022 A1* | 9/2021 | Wollerton ............... A61P 35/00 |
| 2021/0309753 A1 | 10/2021 | Tuna et al. |
| 2021/0355228 A1 | 11/2021 | Lakins et al. |
| 2022/0048996 A1 | 2/2022 | Tuna et al. |
| 2022/0049007 A1 | 2/2022 | Lakins et al. |
| 2022/0185890 A1 | 6/2022 | Tuna et al. |
| 2022/0185894 A1 | 6/2022 | Campbell et al. |
| 2022/0267421 A1 | 8/2022 | Munoz-Olaya et al. |
| 2022/0275092 A1 | 9/2022 | Morrow et al. |

FOREIGN PATENT DOCUMENTS

| | | |
|---|---|---|
| EP | 2242771 B1 | 7/2013 |
| EP | 2905030 A1 | 8/2015 |
| EP | 3470426 A1 | 4/2019 |
| JP | S51-046628 A | 4/1976 |
| JP | 2003-022886 A | 1/2003 |
| JP | 2012-500006 A | 1/2012 |
| JP | 2017-010741 A | 1/2017 |
| WO | 2006/072620 A1 | 7/2006 |
| WO | 2009/000006 A1 | 12/2008 |
| WO | WO 2009/068204 A1 | 6/2009 |
| WO | 2009/132876 A1 | 11/2009 |
| WO | WO 2010/019570 A2 | 2/2010 |
| WO | WO 2010/111282 A1 | 9/2010 |
| WO | WO 2013/181634 A2 | 12/2013 |
| WO | WO 2014/004549 A2 | 1/2014 |
| WO | WO 2014/008218 A1 | 1/2014 |
| WO | WO 2014/140180 A1 | 9/2014 |
| WO | 2015/048312 A1 | 4/2015 |
| WO | WO 2015/119923 A1 | 8/2015 |
| WO | WO 2015/138920 A1 | 9/2015 |
| WO | 2015/198312 A1 | 12/2015 |
| WO | WO 2015/200119 A1 | 12/2015 |
| WO | WO 2016/028672 A1 | 2/2016 |
| WO | 2016/177802 A1 | 11/2016 |
| WO | 2016/185016 A1 | 11/2016 |
| WO | WO 2016/200782 A1 | 12/2016 |
| WO | WO 2017/009456 A1 | 1/2017 |
| WO | WO 2017/015560 A2 | 1/2017 |
| WO | WO 2017/025498 A1 | 2/2017 |
| WO | 2017/052241 A1 | 3/2017 |
| WO | WO 2017/062888 A1 | 4/2017 |
| WO | 2017/077085 A2 | 5/2017 |
| WO | WO 2017/087589 A1 | 5/2017 |
| WO | WO 2017/087901 A2 | 5/2017 |
| WO | 2017/123650 A2 | 7/2017 |
| WO | 2017/182672 A1 | 10/2017 |
| WO | WO 2017/205738 A1 | 11/2017 |
| WO | 2017/220569 A1 | 12/2017 |
| WO | 2018/017673 A1 | 1/2018 |
| WO | 2017/220990 A9 | 3/2018 |
| WO | 2018/056821 A1 | 3/2018 |
| WO | WO 2018/060480 A1 | 4/2018 |
| WO | WO 2018/127610 A1 | 7/2018 |
| WO | WO 2018/222711 A2 | 12/2018 |
| WO | 2019/025545 A1 | 2/2019 |

OTHER PUBLICATIONS

Bacac et al., Abstract 1494: CEA TCB: a novel head-to-tail 2:1 T cell bispecific antibody for treatment of CEA-positive solid tumors. Oncoimmunology. Aug. 2016; 5(Abstract): e1203498. Epub Jun. 24, 2016. doi: 10.1080/2162402X.2016.1203498.

Chester et al., 4-1BB agonism: adding the accelerator to cancer immunotherapy. Cancer Immunol Immunother. Oct. 2016;65(10):1243-8. doi: 10.1007/s00262-016-1829-2. Epub Mar. 31, 2016.

Chester et al., Dual antibody therapy to harness the innate anti-tumor immune response to enhance antibody targeting of tumors. Curr Opin Immunol. Apr. 2015;33:1-8. doi: 10.1016/j.coi.2014.12.010. Epub Jan. 7, 2015.

Goding et al., Combination of adoptive cell transfer, anti-PD-L1 and anti-LAG-3 antibodies for the treatment of recurrent tumors: better with more. OncoImmunology. Oct. 22, 2013;2(8):e25050-1-e25050-3.

Hasenhindl et al., Creating stable stem regions for loop elongation in Fcabs—insights from combining yeast surface display, in silico loop reconstruction and molecular dynamics simulations. Biochim Biophys Acta. 2014;1844(9):1530-1540. doi:10.1016/j.bbapap.2014.04.020.

Hasenhindl et al., Stability assessment on a library scale: a rapid method for the evaluation of the commutability and insertion of residues in C-terminal loops of the CH3 domains of IgG1—Fc. Protein Eng Des Sel. 2013;26(10):675-682.

Jing et al., Combined immune checkpoint protein blockade and low dose whole body irradiation as immunotherapy for myeloma. Journal of Immunotherapy of Cancer. doi: 10.1186/S40425-014-0043-Z. Jan. 20, 2015. 15 pages.

Kraman et al., A LAG-3/PD-L1 bispecific antibody inhibits tumor growth in two syngeneic colon carcinoma models. Journal of ImmunoTherapy of Cancer. 2016;4(Suppl 1):82(abstract P124).

Kraman et al., A LAG-3/PD-L1 bispecific antibody inhibits tumor growth in two syngeneic colon carcinoma models. Retrieved from http://www.f-star.com/media/73722/A-LAG-3-PD-L1-bispecific-antibody-inhibits-tumour-growth-in-two-syngeneic-colon-carcinoma-models.pdf. Nov. 9-13, 2016. 1 page.

Lakins et al., A Novel CD137/PD-L1 Bispecific Antibody Modulates the Tumour Microenvironmentby Activating CD8+ T cells and Results in Tumour Growth Inhibition. F-Star Poster. Nov. 7, 2018. 1 page. Retrieved from https://www.f-star.com/media/87488/201811-SITC-2018-F-star-FS222-Poster-ONLINE.pdf.

Lee et al., 4-1BB and OX40 dual costimulation synergistically stimulate primary specific CD8 T cells for robust effector function. J Immunol. Sep. 1, 2004;173(5):3002-12. doi: 10.4049/jimmunol.173.5.3002.

Leung et al., A HER2-specific Modified Fc Fragment (Fcab) Induces Antitumor Effects Through Degradation of HER2 and Apoptosis. Mol Ther. Nov. 2015;23(11):1722-1733. doi: 10.1038/mt.2015.127. Epub Aug. 3, 2015. Erratum in: Mol Ther. Nov. 2015;23(11):1794.

Lobner et al., Engineered IgG1—FC—one fragment to bind them all. Immunol Rev. Mar. 2016;270(1):113-31. doi: 10.1111/imr.12385.

Lobner et al., Two-faced Fcab prevents polymerization with VEGF and reveals thermodynamics and the 2.15 Å crystal structure of the complex. MAbs. Oct. 2017;9(7)21088-1104. doi: 10.1080/194208622017.1364825. Epub Aug. 17, 2017.

Lundqvist et al., 31lt Annual Meeting and Associated Programs of the Society for Immunotherapy of Cancer (SITC 2016): Part One. Journal for Immunotherapy of Cancer. Nov. 16, 2016;4(1):74(abstract P124).

Qui et al., CD134 plus CD137 dual costimulation induces Eomesodermin in CD4 T cells to program cytotoxic Th1 differentiation. J Immunol. Oct. 1, 2011;187(7):3555-64. doi: 10.4049/jimmunol.1101244. Epub Aug. 31, 2011.

Ramelet et al., Beneficial outcome of combination therapy with 4-1BB targeting antibody. Eur J Cancer. Nov. 29, 2016;69(Suppl 1):S96-S97.

Sallin et al., The anti-lymphoma activities of anti-CD137 monoclonal antibodies are enhanced in Fc?RIII(-/-) mice. Cancer Immunol Immunother. Sep. 2014;63(9):947-58. doi: 10.1007/s00262-014-1567-2. Epub Jun. 14, 2014.

Schlothauer et al., Novel human IgG1 and IgG4 Fc-engineered antibodies with completely abolished immune effector functions. Protein Eng Des Sel. Oct. 2016;29(10):457-466. doi: 10.1093/protein/gzw040. Epub Aug. 29, 2016.

(56) References Cited

OTHER PUBLICATIONS

Shindo et al., Combination immunotherapy with 4-1BB activation and PD-1 blockade enhances antitumor efficacy in a mouse model of subcutaneous tumor. Anticancer Res. Jan. 2015;35(1):129-36.
Vilgelm et al., Combinatorial approach to cancer immunotherapy: strength in numbers. Journal of Leukocyte Biology. 2016;100(2):275-90. Epub Jun. 2, 2016.
Wozniak-Knopp et al., Designing Fcabs: well-expressed and stable high affinity antigen-binding Fc fragments. Protein Eng Des Sel. Sep. 1, 2017;30(9):657-671. doi: 10.1093/protein/gzx042.
Wozniak-Knopp et al., Introducing antigen-binding sites in structural loops of immunoglobulin constant domains: Fc fragments with engineered HER2/neu-binding sites and antibody properties. Protein Eng Des Sel. 2010;23(4):289-297. doi:10.1093/protein/gzq005.
Xu et al, In vitro Characterization of five humanized OKT3 effector function variant antibodies. Cell Immunol. Feb. 25, 2000;200(1):16-26.
[No Author Listed] Abstract for CHI Immuno-Oncology Summit Europe. Mar. 18-22, 2019. 1 page. PDR303.
[No Author Listed] First-in-Class bispecific antibodies for cancer immunotherapy. Presentation at Takeda. Dec. 13, 2016. 24 pages. PDR160.
[No Author Listed] F-Star Modular Bispecific Antibodies. Summary for ATLAS deck. Presented at JP Morgan. Jan. 2017. 1 page. PDR159.
[No Author Listed], Pipeline Overview: F-star is developing a pipeline of bispecific antibodies focused on oncology and immuno-oncology. F-Start website update. Sep. 2016. 2 pages. PDR126.
Ascierto et al., Initial efficacy of anti-lymphocyte activation gene-3 (anti-LAG-3:BMS-986016) in combination with nivolumab (nivo) in pts with melanoma (MEL) previously treated with anti-PD-1/PD-L1 therapy. J Clin Oncology. May 20, 2017;35(15):9520-9520. Abstract only. doi: 10.1200/JCO.2017.35.15_suppl.9520. EPub May 30, 2017.
Berg et al., Biochemistry. 5th ed. New York. 2002. Accessible at https://www.ncbi.nlm.nih.gov/books/NBK22358/section5.5. Accessed Jun. 9, 2021. 4 pages.
Bernett et al., Abstract P122: Multiple bispecific checkpoint combinations enhance T cell activity. J Immunother Cancer. 2016;4(Suppl 1):P122. 2 pages.
Bernett et al., Multiple bispecific checkpoint combinations enhance T cell activity. Xencor Poster Presentation. 2016. 1 page.
Bodhankar et al., PD-L1 Monoclonal Antibody Treats Ischemic Stroke by Controlling Central Nervous System Inflammation. Stroke. Oct. 2015;46(10):2926-34. doi: 10.1161/STROKEAHA.115.010592. Epub Aug. 25, 2015.
Borlak et al., Immune-mediated liver injury of the cancer therapeutic antibody catumaxomab targeting EpCAM, CD3 and Fcγ receptors. Oncotarget. May 10, 2016;7(19):28059-74. doi: 10.18632/oncotarget.8574.
Brewis, Development of an anti-PD-L1 Fcab. Presentation. Human Antibodies and Hybrodomas Conference. Oct. 22, 2018. PDR 312.
Brewis, Identification of a PD-L1 binding Fcab: a potent inhibitor of immunosuppressive signals. Abstract. Huamn Antibodies and Hybridomas 2018. Jun. 11, 2018. 1 page. PDR282.
Brewis, The use of bispecific antibodies to modulate anti-tumour immune responses. Oral Presentation at ELRIG- Research and Innovation. Mar. 29, 2017. 33 pages. PDR177.
Brewis, The use of bispecific antibodies to modulate anti-tumour immune responses. Oral Presentation at PEPtalk. Jan. 12, 2017. 26 pages. PDR163.
Burova et al., Abstract 1484: Combined treatment with anti-LAG-3 and anti-PD-1 fully human monoclonal antibodies inhibits tumor growth in immunocompetent double-humanized LAG-3/PD-1 mice. Proceedings: AACR 107th Annual Meeting 2016. Apr. 16-20, 2016. New Orleans, LA. doi: 10.1158/1538-7445.AM2016-1484. Published Jul. 2016. 8 pages.
Burova et al., Abstract P195: a novel anti-human LAG-3 antibody in combination with anti-human PD-1 (REGN2810) shows enhanced anti-tumor activity in PD-1 × LAG-3 dual-humanized mice and favorable pharmacokinetic and safety profiles in cynomolgus monkey. J Immunother Cancer. 2016;4(Suppl 1):P195. 2 pages.
Camisaschi et al., LAG-3 expression defines a subset of CD4 (+)CD25(high)Foxp3(+) regulatory T cells that are expanded at tumor sites. J Immunol. Jun. 1, 2010;184(11):6545-51. doi: 10.4049/jimmunol.0903879. Epub Apr. 26, 2010.
Cemerski et al., T cell activation and anti-tumor efficacy of anti-LAG-3 antibodies is independent of LAG-3-MHCII blocking capacity. Poster Presentation. 30th Annual Meeting and Associated Programs of the Society for Immunotherapy of Cancer (SITC 2015). National Harbor, MD. Nov. 4-8, 2015. 1 page.
Chen et al., Molecular mechanisms of T cell co-stimulation and co-inhibition. Nat Rev Immunol. Apr. 2013;13(4):227-42. doi: 10.1038/nri3405. Epub Mar. 8, 2013. Erratum in: Nat Rev Immunol. Jul. 2013;13(7):542.
Chiu et al., Antibody Structure and Function: the Basis for Engineering Therapeutics. Antibodies (Basel). Dec. 3, 2019;8(4):55. doi: 10.3390/antib8040055.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80. doi: 10.1073/pnas.0915174107. Epub Feb. 16, 2010.
Davies, Analytical challenges for next generation biologics. Oral Presentation at Waters Biopharma Mini-Seminar. May 24, 2017. 20 pages. PDR191.
Davies, Bispecific Antibodies: New Opportunities for Novel Therapies. Oral Presentation at Bioprocess UK 2016. Nov. 26, 2016. 14 pages. PDR 135.
Davies, Overcoming the Manufacturing Challenges for Bisepcific mAbs. Oral Presentation at 5th Annual Cell Culture and Bioprocessing Congress. Nov. 6, 2016. 16 pages. PDR142.
Davies, Overcoming the Manufacturing Challenges for Bisepcific mAbs. Oral Presentation at Biopronet 3rd Annual Scientific Symposium. Oct. 20, 2016. 16 pages. PDR136.
Daxini et al., Vasculitis associated with immune checkpoint inhibitors-a systematic review. Clin Rheumatol. Sep. 2018;37(9):2579-2584. doi: 10.1007/s10067-018-4177-0. Epub Jun. 19, 2018.
Demeure et al., T Lymphocytes infiltrating various tumour types express the MHC class II ligand lymphocyte activation gene-3 (LAG-3): role of LAG-3/MHC class II interactions in cell-cell contacts. Eur J Cancer. Sep. 2001;37(13):1709-18. doi: 10.1016/s0959-8049(01)00184-8.
Deng et al., LAG-3 confers poor prognosis and its blockade reshapes antitumor response in head and neck squamous cell carcinoma. Oncoimmunology. Oct. 7, 2016;5(11):e1239005. doi: 10.1080/2162402X.2016.1239005.
Doody et al., Abstract B091: a LAG-3/PD-L1 bispecific antibody inhibits tumor growth in two syngeneic colon carcinoma models. Second CRI-CIMT-EATI-AACR International Cancer Immunotherapy Conference: Translating Science into Survival. Sep. 25-28, 2016. New York, NY. doi: 10.1158/23/26/6066.IMM2016-B091. Published Nov. 2016. 8 pages.
Doody, An anti-murine LAG-3/PD-L1 bispecific antibody which modulates T cell activity and inhibits tumour growth. Oral Presentation at 2nd Annual Advances in Immuno-Oncology. Congress. May 16, 2017. 17 pages. PDR188.
Doody, In vivo Efficacy of bispecific antibodies targeting two immmune-modulatory receptors. Oral Presentation at PEGS Europe. Nov. 4, 2016. 16 pages. PDR144.
Everett et al., A LAG-3/PD-L1 bispecific antibody inhibits tumour growth in two syngeneic colon carcinoma models. Poster Presentation. AACR Tumor Immunology and Immunotherapy. Oct. 21, 2016. 1 page. PDR137.
Everett et al., Abstract PR06: a LAG-3/PD-L1 bispecific antibody inhibits tumour growth in two syngeneic colon carcinoma models. AACR Special Conference on Tumor Immunology and Immunotherapy. Oct. 20-23, 2016. Boston, MA. Doi: 10.1158/2326-6074.TUMIMM16-PR06. Published Mar. 2017. 8 pages.
Everett, A LAG-3/PD-L1 Bispecific Antibody Inhibits Tumour Growth in Two Syngeneic Colon Carcinoma Models. Oral Presentation at AACR Tumor Immunology and Immunotherapy. Boston, MA. Oct. 20-23, 2016. 5 pages. PDR141.

(56) References Cited

OTHER PUBLICATIONS

Fiehler, Development of an anti-PD-L1 Fcab. Presentation. European Antibody Congress. Oct. 29, 2018. 26 pages. PDR312.
Foy et al., Poxvirus-Based Active Immunotherapy with PD-1 and LAG-3 Dual Immune Checkpoint Inhibition Overcomes Compensatory Immune Regulation, Yielding Complete Tumor Regression in Mice. PLoS One. Feb. 24, 2016;11(2):e0150084. doi: 10.1371/journal.pone.0150084.
F-Star, First-in-Class Bispecific Antibodies for Cance Immunotherapy. Jul. 2016. Presentation. 14 pages. PDR119.
Gandhi et al., Expression of LAG-3 by tumor-infiltrating lymphocytes is coincident with the suppression of latent membrane antigen-specific CD8+ T-cell function in Hodgkin lymphoma patients. Blood. Oct. 1, 2006;108(7):2280-9. doi: 10.1182/blood-2006-04-015164. Epub Jun. 6, 2006.
Gliddon, Pushing all the buttons: innovating in immuno-oncology with mAb. Oral Presentation at Phacilitate Immunotherapy World 2017. Jan. 18, 2017. 11 pages. PDR165.
Grosso et al., Programmed death-ligand 1 (PD-L1) expression in various tumor types. J Immunother Cancer. 2013;1(Suppl 1):P53. http://www.immunotherapyofcancer.org/content/1/S1/P53. 1 page.
Haines et al., Abstract 4714: Blockade of LAG-3 amplifies immune activation signatures and augments curative antitumor responses to anti-PD-1 therapy in immune competent mouse models of cancer. Proceedings: AACR Annual Meeting 2017. Apr. 1-5, 2017. Washington, DC. doi: 10.1158/1538-7445.AM2017-4714. Published Jul. 2017. 8 pages.
Herbst et al., Predictive correlates of response to the anti-PD-L1 antibody MPDL3280A in cancer patients. Nature. Nov. 27, 2014;515(7528):563-7. doi: 10.1038/nature14011. Author Manuscript.
Hid Cadena et al., Checks and Balances in Autoimmune Vasculitis. Front Immunol. Feb. 22, 2018;9:315. doi: 10.3389/fimmu.2018.00315.
Horn et al., CD3×PDL1 bi-specific T cell engager (BiTE) simultaneously activates T cells and NKT cells, kills PDL1+ tumor cells, and extends the survival of tumor-bearing humanized mice. Oncotarget. Aug. 3, 2017;8(35):57964-57980. doi: 10.18632/oncotarget.19865.
Huang et al., Abstract PR03: Combinatorial blockade of PD-1, CTLA-4, and LAG-3 pathways inhibits murine ovarian tumor growth. Abstracts: AACR Special Conference: Advances in Ovarian Cancer Research: Exploiting Vulnerabilites. Oct. 17-20, 2015. Orlando, FL. doi: 10.1158/1557-3265.OVCA15-PR03. Published Jan. 2016. 8 pages.
Iwai et al., Involvement of PD-L1 on tumor cells in the escape from host immune system and tumor immunotherapy by PD-L1 blockade. Proc Natl Acad Sci U S A. Sep. 17, 2002;99(19):12293-7. doi: 10.1073/pnas.192461099. Epub Sep. 6, 2002.
Jochems et al., Analyses of functions of an anti-PD-L1/TGF?R2 bispecific fusion protein (M7824). Oncotarget. Sep. 8, 2017;8(43):75217-75231. doi: 10.18632/oncotarget.20680.
Kehry et al., Abstract 271: Targeting PD-1, TIM-3 and LAG-3 in combination for improved immunotherapy combinations. AACR 106th Annual Meeting. Apr. 18-22, 2015. Philadelphia, PA. doi: 10.1158/1538-7445.AM2015-271. 8 pages.
Klooster et al., Abstract B088: Generation of immuno-modulatory receptor binding bispecific antibodies to modulate tumor immunity. Second CRI-CIMT-EATI-AACR International Cancer Immunotherapy Conference: Translating Science into Survival. Sep. 25-28, 2016. New York, NY. doi: 10.1158/2326-6066.IMM2016-B088. 4 pages.
Koopmans et al., A novel bispecific antibody for EGFR-directed blockade of the PD-1/PD-L1 immune checkpoint. Oncoimmunology. May 31, 2018;7(8):e1466016. doi: 10.1080/2162402X.2018.1466016.
Kraman et al., A LAG-3/PD-L1 bispecific antibody inhibits tmour growth in two syngeneic colon carcinoma models. Poster Presentation. BSI/NVVI Congress. Dec. 6, 2016. 1 page. PDR153.
Kraman et al., A LAG-3/PD-L1 bispecific antibody inhibits tumour growth in two syngeneic colon carcinoma models. Abstract B091.

Poster Presentation. CRI-CIMT-EATI-AACR Cancer Immunotherapy Conference. Sep. 26, 2016. 1 page. PDR129.
Kraman et al., A LAG-3/PD-L1 bispecific antibody inhibits tumour growth in two syngeneic colon carcinoma models. Poster 003. Poster Presentation. 2nd Annual Advances in Immuno-Oncology Congress. May 15, 2017. 1 page. PDR185.
Kraman et al., A LAG-3/PD-L1 bispecific antibody inhibits tumour growth in two syngeneic colon carcinoma models. Poster 1103. Poster Presentation. Keystone Symposium—Cancer Immunology and Immunotherapy. Mar. 19, 2017. 1 page. PDR174.
Kraman et al., A LAG-3/PD-L1 bispecific antibody inhibits tumour growth in two syngeneic colon carcinoma models. Poster 128. Poster Presentation at SITC. Nov. 9, 2016. 1 page. PDR143.
Kraman et al., A LAG-3/PD-L1 bispecific antibody inhibits tumour growth in two syngeneic colon carcinoma models. Poster 5651. Poster Presentation. AACR Annual Meeting. Apr. 1, 2017. 1 page. PDR176.
Kraman et al., A LAG-3/PD-L1 bispecific antibody inhibits tumour growth in two syngeneic colon carcinoma models. Poster Presentation. International Conference on Human & Translational Immunology. Sep. 16, 2016. 1 page. PDR123.
Kraman et al., A LAG-3/PD-L1 bispecific antibody inhibits tumour growth in two syngeneic colon carcinoma models. Poster 3005. Poster Presentation. Keystome Symposium—Biobetters and Next-Generation Biologics. Jan. 22-26, 2017. 1 pages. PDR164.
Kraman et al., Abstract 5651:a LAG-3/PD/L1 bispecific antibody inhibits tumor growth in two syngeneic colon carcinoma models. AACR Annual Meeting 2017. Apr. 1-5, 2017. Washington, DC. Doi: 10.1158/1538-7445.AM2017-5651. 8 pages.
La Motte-Mohs et al., Abstract 3217: MGD013, a bispecific PD-1 × LAG-3 Dual-Affinity Re-Targeting (DART®) protein with T-cell immunomodulatory activity for cancer treatment. AACR 107th Annual Meeting. Apr. 16-20, 2016. New Orleans, LA. Doi: 10.1158/1538-7445.AM2016-3217. 8 pages.
La Motte-Mohs et al., MGD013, a bispecific PD-1 × LAG-3 Dual-Affinity Re-Targeting (DART®) protein with T-cell immunomodulatory activity for cancer treatment. Poster Presentation. 2016. http://ir.macrogenics.com/events.cfm. 1 page.
Larkin et al., Combined Nivolumab and Ipilimumab or Monotherapy in Untreated Melanoma. N Engl J Med. Jul. 2, 2015;373(1):23-34. doi: 10.1056/NEJMoa1504030. Epub May 31, 2015. Erratum in: N Engl J Med. Nov. 29, 2018;379(22):2185.
Liu et al., Dual Targeting of Innate and Adaptive Checkpoints on Tumor Cells Limits Immune Evasion. Cell Rep. Aug. 21, 2018;24(8):2101-2111. doi: 10.1016/j.celrep.2018.07.062.
McCourt et al., KY1055; a novel ICOS/PD-L1 bispecific antibody, enhance T cell activation and delivers potent monotherapy antitumour response in vivo. Abstract. CIMT 2018. Feb. 28, 2018. 1 page. PDR245.
McCourt et al., KY1055; a novel ICOS/PD-L1 bispecific antibody, enhance T cell activation and delivers potent monotherapy antitumour response in vivo. Poster Presentation. CIMT Conference. May 9, 2018. 1 page. PDR 264.
McCourt et al., KY1055; a novel ICOS/PD-L1 bispecific antibody, enhance T cell activation and delivers potent monotherapy antitumour response in vivo. Presentation. CIMT Conference. May 9, 2018. 13 pages. PDR265.
Michaelson et al., Anti-tumor activity of stability-engineered IgG-like bispecific antibodies targeting TRAIL-R2 and LTbetaR. MAbs. Mar.-Apr. 2009;1(2):128-41. doi: 10.4161/mabs.1.2.7631. Epub Mar. 11, 2009.
Munoz-Olaya, Development of an anti-PD-L1Fcab. Presentation. PEGS Lisbon. Nov. 16, 2018. 24 pages. PDR321.
Nalivaiko et al., A Recombinant Bispecific CD20×CD95 Antibody With Superior Activity Against Normal and Malignant B-cells. Mol Ther. Feb. 2016;24(2):298-305. doi: 10.1038/mt.2015.209. Epub Nov. 19, 2015.
Pavlidou et al., Simultaneous costimulatory T-cell engagement and checkpoint inhibition by PRS-344/ONC0055, a 4-1BB/PD-L1 bispecific compound for tumor localized activation of the immune system. SITC 2018. Poster Presentation. 2018. 1 page.

(56) References Cited

OTHER PUBLICATIONS

Powles et al., MPDL3280A (anti-PD-L1) treatment leads to clinical activity in metastatic bladder cancer. Nature. Nov. 27, 2014;515(7528):558-62. doi: 10.1038/nature13904.
Sainson et al., KY1055, a novel ICOS/PD-L1 bispecific antibody, efficiently enhances T cell activation and delivers a potent anti-tumour response in vivo. Abstract. AACR. Jan. 22, 2018. 1 page. PDR236.
Sainson et al., KY1055, a novel ICOS/PD-L1 bispecific antibody, efficiently enhances T cell activation and delivers a potent anti-tumour response in vivo. Poster Presentation. AACR 2018. Apr. 4, 2018. 1 page. PDR254.
Strauss et al., Phase I Trial of M7824 (MSB0011359C), a Bifunctional Fusion Protein Targeting PD-L1 and TGF?, in Advanced Solid Tumors. Clin Cancer Res. Mar. 15, 2018;24(6):1287-1295. doi: 10.1158/1078-0432.CCR-17/2653. Epub Jan. 3, 2018.
Tuna, Identification of a PD-L1 binding Fcab: a potent inhibitor of immunosuppressive signals. Abstract. European Antibody Congress. May 3, 2018. 1 page. PDR270.
Tuna, The use of bispecific antibodies to modulate anti-tumour immune responses. Oral Presentation at 10th Annual Proteins and Antibodies Congress. Apr. 24, 2017. 26 pages. PDR183.
Vanamee et al., Structural principles of tumor necrosis factor superfamily signaling. Sci Signal. Jan. 2, 2018;11(511):eaao4910. doi: 10.1126/scisignal.aao4910. 12 pages.
Weismann, A LAG-3/PD-L1 Bispecific Antibody Inhibits Tumour Growth in Two Syngeneic Colon Carcinoma Models. International Conference on Human and Translational Immunology. Rhodes, Greece. Sep. 16-21, 2016. Presentation. 6 pages. PDR128.
Wherry, T cell exhaustion. Nat Immunol. Jun. 2011;12(6):492-9. doi: 10.1038/ni.2035.
Wilton, KY1055, a bispecific mAb2 targeting ICOS and PD-L1. Presentation. Feb. 21, 2018. 17 pages. PDR238.
Wolchok et al., Nivolumab plus ipilimumab in advanced melanoma. N Engl J Med. Jul. 11, 2013;369(2):122-33. doi: 10.1056/NEJMoa1302369. Epub Jun. 2, 2013. Erratum in: N Engl J Med. Nov. 29, 2018;379(22):2185. Author Manuscript.
Woo et al., Immune inhibitory molecules LAG-3 and PD-1 synergistically regulate T-cell function to promote tumoral immune escape. Cancer Res. Feb. 15, 2012;72(4):917-27. doi: 10.1158/0008-5472.CAN-11-1620. Epub Dec. 20, 2011.
Workman et al., Negative regulation of T cell homeostasis by lymphocyte activation gene-3 (CD223). J Immunol. Jan. 15, 2005;174(2):688-95. doi: 10.4049/jimmunol.174.2.688.
Workman et al., The CD4-related molecule, LAG-3 (CD223), regulates the expansion of activated T cells. Eur J Immunol. Apr. 2003;33(4):970-9. doi: 10.1002/eji.200323382.
Wydro, Bispecific antibodies: new opportunities for novel therapies. Oral Presentation at 7th Annual Biologics Symposium. Mar. 1, 2017. 24 pages. PDR172.
Wykes et al., Immune Checkpoint blockade in infectious diseases. Nat Rev Immunol. Feb. 2018;18(2):91-104. doi: 10.1038/nri.2017.112. Epub Oct. 9, 2017.
Zhang et al., Structural basis of a novel PD-L1 nanobody for immune Checkpoint blockade. Cell Discov. Mar. 7, 2017;3:17004. doi: 10.1038/celldisc.2017.4.
U.S. Appl. No. 17/259,634, filed Jan. 12, 2021, Munoz-Olaya et al.
U.S. Appl. No. 17/259,754, filed Jan. 12, 2021, Lakins et al.
U.S. Appl. No. 17/259,642, filed Jan. 12, 2021, Wollerton et al.
U.S. Appl. No. 17/259,714, filed Jan. 12, 2021, Tuna et al.
U.S. Appl. No. 17/259,791, filed Jan. 12, 2021, Lakins et al.
U.S. Appl. No. 17/259,796, filed Jan. 12, 2021, Tuna et al.
[No Author Listed], FS118 First in Human Study in Patients With Advanced Malignancies. Sponsored by F-star Therapeutics Limited. Clinical Trial. Retreived from https://clinicaltrials.gov/ct2/show/NCT03440437. Feb. 22, 2018. 7 pages.
Faroudi et al., Abstract 2399: LAG-3/PD-L1 mAb2 can overcome PD-L1-mediated compensatory upregulation of LAG-3 induced by single-agent checkpoint blockade. Proceedings: AACR Annual Meeting 2019; Mar. 29-Apr. 3, 2019. Atlanta, GA. Doi: 10.1158/1538-7445.AM2019-2399. Published Jul. 2019. 4 pages.
Kraman et al., FS118, a Bispecific Antibody Targeting LAG-3 and PD-L1, Enhances T-Cell Activation Resulting in Potent Antitumor Activity. Clin Cancer Res. Jul. 1, 2020;26(13):3333-3344. doi: 10.1158/1078-0432.CCR-19-3548. Epub Apr. 16, 2020.
Yap et al., A first-in-human phase I study of FS118, an anti-LAG-3/PD-L1 bispecific antibody in patients with solid tumors that have progressed on prior PD-1/PD-L1 therapy. Journal of Clinical Oncology. May 26, 2019;37(15_suppl). 4 pages.
U.S. Appl. No. 17/534,315, filed Nov. 23, 2021, Tuna et al.
U.S. Appl. No. 17/533,230, filed Nov. 23, 2021, Campbell et al.
U.S. Appl. No. 17/610,873, filed Nov. 12, 2021, Morrow.
U.S. Appl. No. 17/259,677, filed Jan. 12, 2021, Munoz-Olaya et al.
U.S. Appl. No. 17/610,873, filed Nov. 12, 2021, Morrow et al.
Asgarov et al., A new anti-mesothelin antibody targets selectively the membrane-associated form. MAbs. Apr. 2017;9(3):Supplementary Data, doi: 10.1080/19420862.2017.1288770. 6 pages.
Awuah et al., Reduced Shedding of Surface Mesothelin Improves Efficacy of Mesothelin-Targeting Recombinant Immunotoxins. Mol Cancer Ther. Jul. 2016;15(7):1648-55. doi: 10.1158/1535-7163.MCT-15-0863. Epub May 18, 2016.
Del Bano et al., A Bispecific Antibody-Based Approach for Targeting Mesothelin in Triple Negative Breast Cancer. Front Immunol. Jul. 10, 2019;10:1593. doi: 10.3389/fimmu.2019.01593.
Hassan et al., Mesothelin Immunotherapy for Cancer: Ready for Prime Time? J Clin Oncol. Dec. 2016;34(34):4171-4179. doi: 10.1200/JCO.2016.68.3672. Epub Oct. 31, 2016.
Hassan et al., Phase II clinical trial of amatuximab, a chimeric antimesothelin antibody with pemetrexed and cisplatin in advanced unresectable pleural mesothelioma. Clin Cancer Res. Dec. 1, 2014;20(23):5927-36. doi: 10.1158/1078-0432.CCR-14-0804. Epub Sep. 17, 2014.
Ho et al., A novel high-affinity human monoclonal antibody to mesothelin. Int J Cancer. May 1, 2011;128(9):2020-30. doi: 10.1002/ijc.25557.
Ma et al., Recognition of mesothelin by the therapeutic antibody MORAb-009: structural and mechanistic insights. J Biol Chem. Sep. 28, 2012;287(40):33123-31. doi: 10.1074/jbc.M112.381756. Epub Jul. 11, 2012.
Tang et al., A human single-domain antibody elicits potent antitumor activity by targeting an epitope in mesothelin close to the cancer cell surface. Mol Cancer Ther. Apr. 2013;12(4):416-26. doi: 10.1158/1535-7163.MCT-12-0731. Epub Jan. 31, 2013.
Zhao et al., Novel Antibody Therapeutics Targeting Mesothelin in Solid Tumors. Clin Cancer Drugs. Oct. 2016;3(2):76-86. doi: 10.2174/2212697X03666160218215744.
Callahan et al., Targeting T Cell Co-receptors for Cancer Therapy. Immunity. May 17, 2016;44(5):1069-78. doi: 10.1016/j.immuni.2016.04.023.
Chatterjee et al., Noninvasive Imaging of Immune Checkpoint Ligand PD-L1 in Tumors and Metastases for Guiding Immunotherapy. Mol Imaging. Jan.-Dec. 2017;16:1536012117718459. doi: 10.1177/1536012117718459. 5 pages.
Chu et al., An Update on Anti-CD137 Antibodies in Immunotherapies for Cancer. Int J Mol Sci. Apr. 12, 2019;20(8):1822. doi: 10.3390/ijms20081822. 17 pages.
El-Khoueiry et al., The relationship of pharmacodynamics (PD) and pharmacokinetics (PK) to clinical outcomes in a phase I study of OX40 agonistic monoclonal antibody (mAb) PF-04518600 (PF-8600). J Clin Oncol. May 20, 2017. 35(15_suppl):3027-3027. Meeting Abstract. 2017 ASCO Annual Meeting I. doi: 10.1200/JCO.2017.35.15_suppl.3027.
Gaspar et al., FS120 m Ab2, a dual agonist bispecific antibody targeting OX40 and CD137, activates T cells in vitro and induces FcyR-independent anti-tumour activity. SITC 2018. Nov. 7, 2018. Poster. 10 pages.
Gaspar, FS120 mAb2, a dual agonist bispecific antibody targeting OX40 and CD137. SITC 2018. Nov. 11, 2018. Presentation. 12 pages.
Geuijen et al., Abstract 541: an unbiased screen identifies a CD137×PD-L1 bispecific IgG1 antibody with unique T cell activation and binding properties. Cancer Res. 2019;79(13_Supplement):541. Poster

(56) References Cited

OTHER PUBLICATIONS

Presentation AACR Conference 2019. Jul. 1, 2019. doi: 10.1158/1538-7445.AM2019-541. 4 pages.

Glisson et al., Phase 1 study of MEDI0562, a humanized OX40 agonist monoclonal antibody (mAb), in adult patients (pts) with advanced solid tumors. Annals Onocol. Oct. 1, 2016;27(6):vi361. doi: 10.1093/annonc/mdw378.07.

Gunde et al., Abstract 1532: a novel, monovalent tri-specific antibody-based molecule that simultaneously modulates PD-L1 and 4-1BB exhibits potent anti-tumoral activity in vivo. Cancer Res. 2019;79(13_Supplement):1532. AACR Conference 2019. Jul. 1, 2019. doi: 10.1158/1538-7445.AM2019-1532. 4 pages.

Hebb et al., Administration of low-dose combination anti-CTLA4, anti-CD137, and anti-OX40 into murine tumor or proximal to the tumor draining lymph node induces systemic tumor regression. Cancer Immunol Immunother. Jan. 2018;67(1):47-60. doi: 10.1007/s00262-017-2059-y. Epub Sep. 13, 2017. Author Manuscript. 20 pages.

Kunik et al., Structural consensus among antibodies defines the antigen binding site. PLoS Comput Biol. 2012;8(2):e1002388. doi: 10.1371/journal.pcbi.1002388. Epub Feb. 23, 2012. 12 pages.

Kvarnhammar et al., The CTLA-4 × OX40 bispecific antibody ATOR-1015 induces anti-tumor effects through tumor-directed immune activation. J Immunother Cancer. Apr. 11, 2019;7(1):103. doi: 10.1186/s40425-019-0570-8.

Lakins et al., FS222 mAb2, a bispecific conditional agonist antibody targeting CD137 and PD-L1, induces potent lymphocyte activation and has a favourable safety profile. F-star, Cambridge, UK. Poster Presentation. AACR Annual Meeting Mar. 29-Apr. 3, 2019. Atlanta, GA. Poster No. 1540. 1 page.

Lakins et al., Optimising TNFRSF agonism and checkpoint blockade with a novel CD137/PD-L1 bispecific antibody. Abstracts Therapeutic Development. Dec. 1, 2018;29(Supplement 10):X30. doi: 10.1093/annonc/mdy487.014. 1 page.

Mayes et al., Abstract 539: a bispecific Fc-silenced IgG1 antibody (MCLA-145) requires PD-L1 binding to activate CD137. Cancer Res. 2019;79(13_Supplement):539. AACR Presentation 2019. Jul. 1, 2019. doi: 10.1158/1538-7445.AM2019-539. 4 pages.

Melero et al., Clinical development of immunostimulatory monoclonal antibodies and opportunities for combination. Clin Cancer Res. Mar. 1, 2013;19(5):997-1008. doi: 10.1158/1078-0432.CCR-12-2214.

Perez-Ruiz et al., Anti-CD137 and PD-1/PD-L1 Antibodies En Route toward Clinical Synergy. Clin Cancer Res. Sep. 15, 2017;23(18):5326-5328. doi: 10.1158/1078-0432.CCR-17-1799. Epub Aug. 8, 2017.

Poon et al., Dual agonist bispecific antibody targeting OX40 and DC137 mediates anti-tumour immunity and synergises with PD-1/PD-L1 blockade to improve survival in a syngeneic mouse model. AACR 2019. Mar. 29, 2019. Poster. 9 pages.

Ryan et al., A novel biologic platform elicits profound T cell costimulatory activity and antitumor immunity in mice. Cancer Immunol Immunother. Apr. 2018;67(4):605-613. doi: 10.1007/s00262-018-2116-1. Epub Jan. 11, 2018.

Tuna, Delivering the next immuno-oncology breakthrough. PEGS Europe 2018. Nov. 11, 2018. Presentation. 24 pages.

\* cited by examiner

A

B

A

B

A

B

C

D

E

F

A

B

A

B

C

D

| Treatments | Vehicle | FS1-60 | FI | FI + FS1-60 | FI/FS1-60 | RI/FS1-60 |
|---|---|---|---|---|---|---|
| Vehicle | | ns | *** | *** | *** | *** |
| FS1-60 | | | *** | *** | *** | *** |
| Ficlatuzumab (FI) | | | | ns | ** | * |
| FI + FS1-60 | | | | | * | ns |
| FI/FS1-60 | | | | | | ns |
| RI/FS1-60 | | | | | | |

\* = $p < 0.05$;  = $p < 0.01$; * = $p < 0.001$ ns = not significant

Figure 14

| Treatments | Vehicle | FS1-65 | Ficlatuzumab (FI) | FI + FS1-65 | FI/FS1-60 | FI/FS1-65 |
|---|---|---|---|---|---|---|
| Vehicle | | * | ** | * | *** | *** |
| FS1-65 | | | ** | ns | *** | *** |
| Ficlatuzumab (FI) | | | | ns | * | ns |
| FI + FS1-65 | | | | | * | ns |
| FI/FS1-60 | | | | | | * |
| FI/FS1-65 | | | | | | |

\* = $p < 0.05$;  = $p < 0.01$; * = $p < 0.001$ ns = not significant

Figure 15 ically to cell. HGF is secreted by mesenchymal cells and acts as a

SEQUENCE LISTING

<160> NUMBER OF SEQ ID NOS: 72

<210> SEQ ID NO 1
<211> LENGTH: 6
<212> TYPE: PRT
<213> ORGANISM: Artificial Sequence
<220> FEATURE:
<223> OTHER INFORMATION: Fcab FS1-60 CH3 domain AB loop

```
<400> SEQUENCE: 1

Leu Asp Glu Gly Gly Pro
1               5

<210> SEQ ID NO 2
<211> LENGTH: 3
<212> TYPE: PRT
<213> ORGANISM: Artificial Sequence
<220> FEATURE:
<223> OTHER INFORMATION: Fcab FS1-60 CH3 domain CD loop

<400> SEQUENCE: 2

Thr Tyr Gly
1

<210> SEQ ID NO 3
<211> LENGTH: 7
<212> TYPE: PRT
<213> ORGANISM: Artificial Sequence
<220> FEATURE:
<223> OTHER INFORMATION: Fcab FS1-60 CH3 domain EF loop

<400> SEQUENCE: 3

Ser His Trp Arg Trp Tyr Ser
1               5

<210> SEQ ID NO 4
<211> LENGTH: 107
<212> TYPE: PRT
<213> ORGANISM: Artificial Sequence
<220> FEATURE:
<223> OTHER INFORMATION: Fcab FS1-60 CH3 domain

<400> SEQUENCE: 4

Gly Gln Pro Arg Glu Pro Gln Val Tyr Thr Leu Pro Pro Ser Arg Asp
1               5                   10                  15

Glu Leu Asp Glu Gly Gly Pro Val Ser Leu Thr Cys Leu Val Lys Gly
            20                  25                  30

Phe Tyr Pro Ser Asp Ile Ala Val Glu Trp Glu Ser Thr Tyr Gly Pro
        35                  40                  45

Glu Asn Asn Tyr Lys Thr Thr Pro Pro Val Leu Asp Ser Asp Gly Ser
    50                  55                  60

Phe Phe Leu Tyr Ser Arg Leu Thr Val Ser His Trp Arg Trp Tyr Ser
65                  70                  75                  80

Gly Asn Val Phe Ser Cys Ser Val Met His Glu Ala Leu His Asn His
                85                  90                  95

Tyr Thr Gln Lys Ser Leu Ser Leu Ser Pro Gly
            100                 105

<210> SEQ ID NO 5
<211> LENGTH: 321
<212> TYPE: DNA
<213> ORGANISM: Artificial Sequence
<220> FEATURE:
<223> OTHER INFORMATION: Fcab FS1-60 CH3 domain

<400> SEQUENCE: 5
ggccagcctc gagaaccaca ggtgtacacc ctgcccccat cccgggatga gttggatgag     60
gggggtcctg tcagcctgac ctgcctggtc aaaggcttct atcccagcga catcgccgtg    120
gagtgggaga gcacttatgg gccggagaac aactacaaga ccacgcctcc cgtgctggac    180
tccgacggct ccttcttcct ctacagcagg ctcaccgtgt ctcattggag gtggtactct    240
```

```
gggaacgtct tctcatgctc cgtgatgcat gaggctctgc acaaccacta cacacagaag    300
agcctctccc tgtctccggg t                                               321
```

<210> SEQ ID NO 6
<211> LENGTH: 217
<212> TYPE: PRT
<213> ORGANISM: Artificial Sequence
<220> FEATURE:
<223> OTHER INFORMATION: CH2 adn CH3 domains of Fcab FS1-60

<400> SEQUENCE: 6

```
Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Asp Glu Gly Gly Pro Val Ser Leu Thr Cys Leu Val Lys Gly Phe Tyr
    130                 135                 140

Pro Ser Asp Ile Ala Val Glu Trp Glu Ser Thr Tyr Gly Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Ser His Trp Arg Trp Tyr Ser Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly
    210                 215
```

<210> SEQ ID NO 7
<211> LENGTH: 651
<212> TYPE: DNA
<213> ORGANISM: Artificial Sequence
<220> FEATURE:
<223> OTHER INFORMATION: CH2 and CH3 domains of Fcab FS1-60

<400> SEQUENCE: 7

```
gcccccgagc tgctgggagg cccttccgtg tttctgttcc ccccaaagcc caaggacacc    60
ctgatgatct cccggacccc cgaagtgacc tgcgtggtgg tggatgtgtc ccacgaggac   120
cctgaagtga agttcaattg gtacgtggac ggcgtggaag tgcacaacgc caagaccaag   180
cccagagagg aacagtacaa ctccacctac cgggtggtgt ccgtgctgac cgtgctgcac   240
caggattggc tgaacggcaa agagtacaag tgcaaggtgt ccaacaaggc cctgcctgcc   300
cccatcgaaa agaccatctc caaggccaag ggccagcccc gggaacccca ggtgtacaca   360
```

```
ctgcccccta gcagggacga gctggatgaa ggcggacctg tgtccctgac ctgtctcgtg    420
aagggcttct accectccga tatcgccgtg aatgggagt ccacctacgg ccccgagaac    480
aactacaaga ccaccccccc tgtgctggac tccgacggct ccttctttct gtactcccgc    540
ctgaccgtgt cccactggcg gtggtactct ggcaacgtgt tctcctgcag cgtgatgcac    600
gaggccctgc acaaccacta cacccagaag tccctgtccc tgagccccgg c            651
```

<210> SEQ ID NO 8
<211> LENGTH: 7
<212> TYPE: PRT
<213> ORGANISM: Artificial Sequence
<220> FEATURE:
<223> OTHER INFORMATION: Fcab FS1-65 CH3 domain EF loop

<400> SEQUENCE: 8

Ser Tyr Trp Arg Trp Val Lys
1               5

<210> SEQ ID NO 9
<211> LENGTH: 107
<212> TYPE: PRT
<213> ORGANISM: Artificial Sequence
<220> FEATURE:
<223> OTHER INFORMATION: Fcab FS1-65 CH3 domain

<400> SEQUENCE: 9

Gly Gln Pro Arg Glu Pro Gln Val Tyr Thr Leu Pro Pro Ser Arg Asp
1               5                   10                  15

Glu Leu Asp Glu Gly Gly Pro Val Ser Leu Thr Cys Leu Val Lys Gly
            20                  25                  30

Phe Tyr Pro Ser Asp Ile Ala Val Glu Trp Glu Ser Thr Tyr Gly Pro
        35                  40                  45

Glu Asn Asn Tyr Lys Thr Thr Pro Pro Val Leu Asp Ser Asp Gly Ser
    50                  55                  60

Phe Phe Leu Tyr Ser Lys Leu Thr Val Ser Tyr Trp Arg Trp Val Lys
65                  70                  75                  80

Gly Asn Val Phe Ser Cys Ser Val Met His Glu Ala Leu His Asn His
                85                  90                  95

Tyr Thr Gln Lys Ser Leu Ser Leu Ser Pro Gly
            100                 105

<210> SEQ ID NO 10
<211> LENGTH: 321
<212> TYPE: DNA
<213> ORGANISM: Artificial Sequence
<220> FEATURE:
<223> OTHER INFORMATION: Fcab FS1-65 CH3 domain

<400> SEQUENCE: 10

```
ggccagcctc gagaaccaca ggtgtacacc ctgcccccat cccgggatga gttggatgag    60
gggggtcctg tcagcctgac ctgcctggtc aaaggcttct atcccagcga catcgccgtg    120
gagtgggaga gcacttatgg gccggagaac aactacaaga ccacgcctcc cgtgctggac    180
tccgacggct ccttcttcct ctacagcaag ctcaccgtgt cttactggag gtgggttaaa    240
gggaacgtct tctcatgctc cgtgatgcat gaggctctgc acaaccacta cacacagaag    300
agcctctccc tgtctccggg t                                              321
```

<210> SEQ ID NO 11
<211> LENGTH: 217

<212> TYPE: PRT
<213> ORGANISM: Artificial Sequence
<220> FEATURE:
<223> OTHER INFORMATION: CH2 and CH3 domains of Fcab FS1-65

<400> SEQUENCE: 11

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Asp Glu Gly Gly Pro Val Ser Leu Thr Cys Leu Val Lys Gly Phe Tyr
    130                 135                 140

Pro Ser Asp Ile Ala Val Glu Trp Glu Ser Thr Tyr Gly Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Ser Tyr Trp Arg Trp Val Lys Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly
    210                 215

<210> SEQ ID NO 12
<211> LENGTH: 651
<212> TYPE: DNA
<213> ORGANISM: Artificial Sequence
<220> FEATURE:
<223> OTHER INFORMATION: CH2 and CH3 domains of Fcab FS1-65

<400> SEQUENCE: 12
gcccccgagc tgctgggagg cccttccgtg tttctgttcc ccccaaagcc caaggacacc      60
ctgatgatct cccggacccc cgaagtgacc tgcgtggtgg tggatgtgtc ccacgaggac     120
cctgaagtga agttcaattg gtacgtggac ggcgtggaag tgcacaacgc caagaccaag     180
cccagagagg aacagtacaa ctccacctac cgggtggtgt ccgtgctgac cgtgctgcac     240
caggattggc tgaacggcaa agagtacaag tgcaaggtgt ccaacaaggc cctgcctgcc     300
cccatcgaaa agaccatctc caaggccaag ggccagcctc gagaaccaca ggtgtacacc     360
ctgcccccat cccgggatga gttggatgag ggggtcctg tcagcctgac ctgcctggtc      420
aaaggcttct atcccagcga catcgccgtg gagtgggaga gcacttatgg ccggagaac      480 aactacaaga ccacgcctcc cgtgctggac tccgacggct ccttcttcct ctacagcaag     540
ctcaccgtgt cttactggag gtgggttaaa gggaacgtct tctcatgctc cgtgatgcat     600
gaggctctgc acaaccacta cacacagaag agcctctccc tgtctccggg t    651

<210> SEQ ID NO 13
<211> LENGTH: 5
<212> TYPE: PRT
<213> ORGANISM: Artificial Sequence
<220> FEATURE:
<223> OTHER INFORMATION: Fcab FS1-67 CH3 AB loop

<400> SEQUENCE: 13

Thr Asp Asp Gly Pro
1               5

<210> SEQ ID NO 14
<211> LENGTH: 7
<212> TYPE: PRT
<213> ORGANISM: Artificial Sequence
<220> FEATURE:
<223> OTHER INFORMATION: Fcab FS1-67 CH3 EF loop

<400> SEQUENCE: 14

Ser Tyr Trp Arg Trp Tyr Lys
1               5

<210> SEQ ID NO 15
<211> LENGTH: 106
<212> TYPE: PRT
<213> ORGANISM: Artificial Sequence
<220> FEATURE:
<223> OTHER INFORMATION: Fcab FS1-67 CH3 domain

<400> SEQUENCE: 15

Gly Gln Pro Arg Glu Pro Gln Val Tyr Thr Leu Pro Pro Ser Arg Asp
1               5                   10                  15

Glu Thr Asp Asp Gly Pro Val Ser Leu Thr Cys Leu Val Lys Gly Phe
            20                  25                  30

Tyr Pro Ser Asp Ile Ala Val Glu Trp Glu Ser Thr Tyr Gly Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Ser Tyr Trp Arg Trp Tyr Lys Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 16
<211> LENGTH: 318
<212> TYPE: DNA
<213> ORGANISM: Artificial Sequence
<220> FEATURE:
<223> OTHER INFORMATION: Fcab FS1-67 CH3 domain

<400> SEQUENCE: 16
ggccagcctc gagaaccaca ggtgtacacc ctgcccccat cccgggatga gactgacgac    60
ggtccggtca gcctgacctg cctggtcaaa ggcttctatc cagcgacat cgccgtggag    120 tgggagagca cttatggccc ggagaacaac tacaagacca cgcctcccgt gctggactcc    180
gacggatcct tcttcctcta cagcaagctc accgtgtctt actggaggtg gtacaaaggg    240
aacgtcttct catgctccgt gatgcatgag gctctgcaca accactacac acagaagagc    300
ctctccctgt ctccgggt                                                    318

<210> SEQ ID NO 17
<211> LENGTH: 216
<212> TYPE: PRT
<213> ORGANISM: Artificial Sequence
<220> FEATURE:
<223> OTHER INFORMATION: CH2 and CH3 domains of Fcab FS1-67

<400> SEQUENCE: 17

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Thr
        115                 120                 125

Asp Asp Gly Pro Val Ser Leu Thr Cys Leu Val Lys Gly Phe Tyr Pro
    130                 135                 140

Ser Asp Ile Ala Val Glu Trp Glu Ser Thr Tyr Gly Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Tyr Trp Arg Trp Tyr Lys Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 18
<211> LENGTH: 648
<212> TYPE: DNA
<213> ORGANISM: Artificial Sequence
<220> FEATURE:
<223> OTHER INFORMATION: CH2 and CH3 domains of Fcab FS1-67

<400> SEQUENCE: 18
gcccccgagc tgctgggagg cccttccgtg tttctgttcc cccaaagcc caaggacacc       60 ctgatgatct cccggacccc cgaagtgacc tgcgtggtgg tggatgtgtc ccacgaggac      120
cctgaagtga agttcaattg gtacgtggac ggcgtggaag tgcacaacgc caagaccaag      180
cccagagagg aacagtacaa ctccacctac cgggtggtgt ccgtgctgac cgtgctgcac      240
caggattggc tgaacggcaa agagtacaag tgcaaggtgt ccaacaaggc cctgcctgcc      300
cccatcgaaa agaccatctc caaggccaag ggccagcctc gagaaccaca ggtgtacacc      360
ctgcccccat cccgggatga gactgacgac ggtccggtca gctgacctg cctggtcaaa      420 ggcttctatc ccagcgacat cgccgtggag tgggagagca cttatgggcc ggagaacaac      480

```
tacaagacca cgcctcccgt gctggactcc gacggatcct tcttcctcta cagcaagctc    540
accgtgtctt actggaggtg gtacaaaggg aacgtcttct catgctccgt gatgcatgag    600
gctctgcaca accactacac acagaagagc ctctccctgt ctccgggt                 648
```

```
<210> SEQ ID NO 19
<211> LENGTH: 110
<212> TYPE: PRT
<213> ORGANISM: Artificial Sequence
<220> FEATURE:
<223> OTHER INFORMATION: Fcab FS1-60, Fcab FS1-65 and Fcab FS1-67 CH2
      domain

<400> SEQUENCE: 19
```

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

```
<210> SEQ ID NO 20
<211> LENGTH: 330
<212> TYPE: DNA
<213> ORGANISM: Artificial Sequence
<220> FEATURE:
<223> OTHER INFORMATION: Fcab FS1-60, Fcab FS1-65 and Fcab FS1-67 CH2
      domain

<400> SEQUENCE: 20
gcccccgagc tgctgggagg cccttccgtg tttctgttcc cccaaagcc caaggacacc      60 ctgatgatct cccggacccc cgaagtgacc tgcgtggtgg tggatgtgtc ccacgaggac    120
cctgaagtga agttcaattg gtacgtggac ggcgtggaag tgcacaacgc caagaccaag    180
cccagagagg aacagtacaa ctccacctac cgggtggtgt ccgtgctgac cgtgctgcac    240
caggattggc tgaacggcaa agagtacaag tgcaaggtgt ccaacaaggc cctgcctgcc    300
cccatcgaaa agaccatctc caaggccaag                                     330
```

```
<210> SEQ ID NO 21
<211> LENGTH: 5
<212> TYPE: PRT
<213> ORGANISM: Artificial Sequence
<220> FEATURE:
<223> OTHER INFORMATION: RI CDR1 VH

<400> SEQUENCE: 21
```

Ile Tyr Tyr Trp Ser
1               5

```
<210> SEQ ID NO 22
<211> LENGTH: 16
<212> TYPE: PRT
```

```
<213> ORGANISM: Artificial Sequence
<220> FEATURE:
<223> OTHER INFORMATION: RI CDR2 VH

<400> SEQUENCE: 22

Tyr Val Tyr Tyr Ser Gly Ser Thr Asn Tyr Asn Pro Ser Leu Lys Ser
 1               5                  10                  15

<210> SEQ ID NO 23
<211> LENGTH: 12
<212> TYPE: PRT
<213> ORGANISM: Artificial Sequence
<220> FEATURE:
<223> OTHER INFORMATION: RI CDR3 VH

<400> SEQUENCE: 23

Gly Gly Tyr Asp Phe Trp Ser Gly Tyr Phe Asp Tyr
 1               5                  10

<210> SEQ ID NO 24
<211> LENGTH: 11
<212> TYPE: PRT
<213> ORGANISM: Artificial Sequence
<220> FEATURE:
<223> OTHER INFORMATION: RI CDR1 VL

<400> SEQUENCE: 24

Arg Ala Ser Gln Ser Val Asp Ser Asn Leu Ala
 1               5                  10

<210> SEQ ID NO 25
<211> LENGTH: 7
<212> TYPE: PRT
<213> ORGANISM: Artificial Sequence
<220> FEATURE:
<223> OTHER INFORMATION: RI CDR2 VL

<400> SEQUENCE: 25

Gly Ala Ser Thr Arg Ala Thr
 1               5

<210> SEQ ID NO 26
<211> LENGTH: 10
<212> TYPE: PRT
<213> ORGANISM: Artificial Sequence
<220> FEATURE:
<223> OTHER INFORMATION: RI CDR3 VL

<400> SEQUENCE: 26

Gln Gln Tyr Ile Asn Trp Pro Pro Ile Thr
 1               5                  10

<210> SEQ ID NO 27
<211> LENGTH: 445
<212> TYPE: PRT
<213> ORGANISM: Artificial Sequence
<220> FEATURE:
<223> OTHER INFORMATION: RI heavy chain

<400> SEQUENCE: 27

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ile Tyr
                20                  25                  30

Tyr Trp Ser Trp Ile Arg Gln Pro Pro Gly Lys Gly Leu Glu Trp Ile
            35                  40                  45
```

Gly Tyr Val Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Asn Ser Val Thr Ala Ala Asp Thr Ala Val Tyr Tyr Cys Ala
                 85                  90                  95

Arg Gly Gly Tyr Asp Phe Trp Ser Gly Tyr Phe Asp Tyr Trp Gly Gln
                 100                 105                 110

Gly Thr Leu Val Thr Val Ser Ser Ala Ser Thr Lys Gly Pro Ser Val
             115                 120                 125

Phe Pro Leu Ala Pro Cys Ser Arg Ser Thr Ser Glu Ser Thr Ala Ala
 130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
                 180                 185                 190

Ser Ser Asn Phe Gly Thr Gln Thr Tyr Thr Cys Asn Val Asp His Lys
             195                 200                 205

Pro Ser Asn Thr Lys Val Asp Lys Thr Val Glu Arg Lys Cys Cys Val
 210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                 245                 250                 255

Glu Val Thr Cys Val Val Val Asp Val Ser His Glu Asp Pro Glu Val
                 260                 265                 270

Gln Phe Asn Trp Tyr Val Asp Gly Val Glu Val His Asn Ala Lys Thr
             275                 280                 285

Lys Pro Arg Glu Glu Gln Phe Asn Ser Thr Phe Arg Val Val Ser Val
 290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                 325                 330                 335

Lys Thr Lys Gly Gln Pro Arg Glu Pro Gln Val Tyr Thr Leu Pro Pro
             340                 345                 350

Ser Arg Glu Glu Met Thr Lys Asn Gln Val Ser Leu Thr Cys Leu Val
             355                 360                 365

Lys Gly Phe Tyr Pro Ser Asp Ile Ala Val Glu Trp Glu Ser Asn Gly
 370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                 405                 410                 415

Gln Gln Gly Asn Val Phe Ser Cys Ser Val Met His Glu Ala Leu His
                 420                 425                 430

Asn His Tyr Thr Gln Lys Ser Leu Ser Leu Ser Pro Gly
             435                 440                 445

<210> SEQ ID NO 28
<211> LENGTH: 215

```
<212> TYPE: PRT
<213> ORGANISM: Artificial Sequence
<220> FEATURE:
<223> OTHER INFORMATION: RI and RI/FS1-60, RI/FS1-65 and RI/FS1-67 light
      chain

<400> SEQUENCE: 28

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asp Ser Asn
            20                  25                  30

Leu Ala Trp Tyr Arg Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ile Asn Trp Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 29
<211> LENGTH: 120
<212> TYPE: PRT
<213> ORGANISM: Artificial Sequence
<220> FEATURE:
<223> OTHER INFORMATION: RI VH domain

<400> SEQUENCE: 29

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ile Tyr
            20                  25                  30

Tyr Trp Ser Trp Ile Arg Gln Pro Pro Gly Lys Gly Leu Glu Trp Ile
        35                  40                  45

Gly Tyr Val Tyr Tyr Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Gly Gly Tyr Asp Phe Trp Ser Gly Tyr Phe Asp Tyr Trp Gly Gln
```

```
                   100                 105                 110

Gly Thr Leu Val Thr Val Ser Ser
            115                 120

<210> SEQ ID NO 30
<211> LENGTH: 109
<212> TYPE: PRT
<213> ORGANISM: Artificial Sequence
<220> FEATURE:
<223> OTHER INFORMATION: RI VL domain

<400> SEQUENCE: 30

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asp Ser Asn
            20                  25                  30

Leu Ala Trp Tyr Arg Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ile Asn Trp Pro Pro
                85                  90                  95

Ile Thr Phe Gly Gln Gly Thr Arg Leu Glu Ile Lys Arg
            100                 105

<210> SEQ ID NO 31
<211> LENGTH: 5
<212> TYPE: PRT
<213> ORGANISM: Artificial Sequence
<220> FEATURE:
<223> OTHER INFORMATION: FI CDR1 VH

<400> SEQUENCE: 31

Thr Tyr Trp Met His
1               5

<210> SEQ ID NO 32
<211> LENGTH: 17
<212> TYPE: PRT
<213> ORGANISM: Artificial Sequence
<220> FEATURE:
<223> OTHER INFORMATION: FI CDR2 VH

<400> SEQUENCE: 32

Glu Ile Asn Pro Thr Asn Gly His Thr Asn Tyr Asn Gln Lys Phe Gln
1               5                   10                  15

Gly

<210> SEQ ID NO 33
<211> LENGTH: 9
<212> TYPE: PRT
<213> ORGANISM: Artificial Sequence
<220> FEATURE:
<223> OTHER INFORMATION: FI CDR3 VH

<400> SEQUENCE: 33

Asn Tyr Val Gly Ser Ile Phe Asp Tyr
1               5

<210> SEQ ID NO 34
```

```
<211> LENGTH: 11
<212> TYPE: PRT
<213> ORGANISM: Artificial Sequence
<220> FEATURE:
<223> OTHER INFORMATION: FI CDR1 VL

<400> SEQUENCE: 34

Lys Ala Ser Glu Asn Val Val Ser Tyr Val Ser
1               5                   10

<210> SEQ ID NO 35
<211> LENGTH: 7
<212> TYPE: PRT
<213> ORGANISM: Artificial Sequence
<220> FEATURE:
<223> OTHER INFORMATION: FI CDR2 VL

<400> SEQUENCE: 35

Gly Ala Ser Asn Arg Glu Ser
1               5

<210> SEQ ID NO 36
<211> LENGTH: 9
<212> TYPE: PRT
<213> ORGANISM: Artificial Sequence
<220> FEATURE:
<223> OTHER INFORMATION: FI CDR3 VL

<400> SEQUENCE: 36

Gly Gln Ser Tyr Asn Tyr Pro Tyr Thr
1               5

<210> SEQ ID NO 37
<211> LENGTH: 447
<212> TYPE: PRT
<213> ORGANISM: Artificial Sequence
<220> FEATURE:
<223> OTHER INFORMATION: FI heavy chain

<400> SEQUENCE: 37

Gln Val Gln Leu Val Gln Pro Gly Ala Glu Val Lys Lys Pro Gly Thr
1               5                   10                  15

Ser Val Lys Leu Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Ile
        35                  40                  45

Gly Glu Ile Asn Pro Thr Asn Gly His Thr Asn Tyr Asn Gln Lys Phe
    50                  55                  60

Gln Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Val Gly Ser Ile Phe Asp Tyr Trp Gly Gln Gly Thr
            100                 105                 110

Leu Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 38
<211> LENGTH: 214
<212> TYPE: PRT
<213> ORGANISM: Artificial Sequence
<220> FEATURE:
<223> OTHER INFORMATION: FI and FI/FS1-60, FI/FS1-65 and FI-FS1-67 light
      chain

<400> SEQUENCE: 38

Asp Ile Val Met Thr Gln Ser Pro Asp Ser Leu Ala Met Ser Leu Gly
1               5                   10                  15

Glu Arg Val Thr Leu Asn Cys Lys Ala Ser Glu Asn Val Val Ser Tyr
            20                  25                  30

Val Ser Trp Tyr Gln Gln Lys Pro Gly Gln Ser Pro Lys Leu Leu Ile
            35                  40                  45

Tyr Gly Ala Ser Asn Arg Glu Ser Gly Val Pro Asp Arg Phe Ser Gly
        50                  55                  60

Ser Gly Ser Ala Thr Asp Phe Thr Leu Thr Ile Ser Ser Val Gln Ala
65                  70                  75                  80

Glu Asp Val Ala Asp Tyr His Cys Gly Gln Ser Tyr Asn Tyr Pro Tyr
```

```
            85                  90                  95
Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 39
<211> LENGTH: 118
<212> TYPE: PRT
<213> ORGANISM: Artificial Sequence
<220> FEATURE:
<223> OTHER INFORMATION: FI VH domain

<400> SEQUENCE: 39

Gln Val Gln Leu Val Gln Pro Gly Ala Glu Val Lys Lys Pro Gly Thr
1               5                   10                  15

Ser Val Lys Leu Ser Cys Lys Ala Ser Gly Tyr Thr Phe Thr Thr Tyr
                20                  25                  30

Trp Met His Trp Val Arg Gln Ala Pro Gly Gln Gly Leu Glu Trp Ile
            35                  40                  45

Gly Glu Ile Asn Pro Thr Asn Gly His Thr Asn Tyr Asn Gln Lys Phe
    50                  55                  60

Gln Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Val Gly Ser Ile Phe Asp Tyr Trp Gly Gln Gly Thr
            100                 105                 110

Leu Leu Thr Val Ser Ser
        115

<210> SEQ ID NO 40
<211> LENGTH: 108
<212> TYPE: PRT
<213> ORGANISM: Artificial Sequence
<220> FEATURE:
<223> OTHER INFORMATION: FI VL domain

<400> SEQUENCE: 40

Asp Ile Val Met Thr Gln Ser Pro Asp Ser Leu Ala Met Ser Leu Gly
1               5                   10                  15

Glu Arg Val Thr Leu Asn Cys Lys Ala Ser Glu Asn Val Val Ser Tyr
                20                  25                  30

Val Ser Trp Tyr Gln Gln Lys Pro Gly Gln Ser Pro Lys Leu Leu Ile
            35                  40                  45
```

```
Tyr Gly Ala Ser Asn Arg Glu Ser Gly Val Pro Asp Arg Phe Ser Gly
         50                  55                  60

Ser Gly Ser Ala Thr Asp Phe Thr Leu Thr Ile Ser Ser Val Gln Ala
 65                  70                  75                  80

Glu Asp Val Ala Asp Tyr His Cys Gly Gln Ser Tyr Asn Tyr Pro Tyr
                 85                  90                  95

Thr Phe Gly Gln Gly Thr Lys Leu Glu Ile Lys Arg
                100                 105

<210> SEQ ID NO 41
<211> LENGTH: 446
<212> TYPE: PRT
<213> ORGANISM: Artificial Sequence
<220> FEATURE:
<223> OTHER INFORMATION: mAb2 RI/FS1-60 heavy chain

<400> SEQUENCE: 41

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ile Tyr
                 20                  25                  30

Tyr Trp Ser Trp Ile Arg Gln Pro Pro Gly Lys Gly Leu Glu Trp Ile
             35                  40                  45

Gly Tyr Val Tyr Tyr Ser Gly Ser Thr Asn Tyr Asn Pro Ser Leu Lys
         50                  55                  60

Ser Arg Val Thr Ile Ser Val Asp Thr Ser Lys Asn Gln Phe Ser Leu
 65                  70                  75                  80

Lys Leu Asn Ser Val Thr Ala Ala Asp Thr Ala Val Tyr Tyr Cys Ala
                 85                  90                  95

Arg Gly Gly Tyr Asp Phe Trp Ser Gly Tyr Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300
```

```
Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Asp Glu Leu Asp Glu Gly Pro Val Ser Leu Thr Cys Leu
        355                 360                 365

Val Lys Gly Phe Tyr Pro Ser Asp Ile Ala Val Glu Trp Glu Ser Thr
    370                 375                 380

Tyr Gly Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Ser His Trp Arg
                405                 410                 415

Trp Tyr Ser Gly Asn Val Phe Ser Cys Ser Val Met His Glu Ala Leu
                420                 425                 430

His Asn His Tyr Thr Gln Lys Ser Leu Ser Leu Ser Pro Gly
            435                 440                 445

<210> SEQ ID NO 42
<211> LENGTH: 448
<212> TYPE: PRT
<213> ORGANISM: Artificial Sequence
<220> FEATURE:
<223> OTHER INFORMATION: mAb2 FI/FS1-60 heavy chain

<400> SEQUENCE: 42

Gln Val Gln Leu Val Gln Pro Gly Ala Glu Val Lys Lys Pro Gly Thr
1               5                   10                  15

Ser Val Lys Leu Ser Cys Lys Ala Ser Gly Tyr Thr Phe Thr Thr Tyr
                20                  25                  30

Trp Met His Trp Val Arg Gln Ala Pro Gly Gln Gly Leu Glu Trp Ile
            35                  40                  45

Gly Glu Ile Asn Pro Thr Asn Gly His Thr Asn Tyr Asn Gln Lys Phe
    50                  55                  60

Gln Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Val Gly Ser Ile Phe Asp Tyr Trp Gly Gln Gly Thr
                100                 105                 110

Leu Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220
```

```
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Asp Glu Gly Gly Pro Val Ser Leu Thr
            355                 360                 365

Cys Leu Val Lys Gly Phe Tyr Pro Ser Asp Ile Ala Val Glu Trp Glu
370                 375                 380

Ser Thr Tyr Gly Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Ser His
                405                 410                 415

Trp Arg Trp Tyr Ser Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 43
<211> LENGTH: 446
<212> TYPE: PRT
<213> ORGANISM: Artificial Sequence
<220> FEATURE:
<223> OTHER INFORMATION: mAb2 RI/FS1-65 heavy chain

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ile Tyr
            20                  25                  30

Tyr Trp Ser Trp Ile Arg Gln Pro Pro Gly Lys Gly Leu Glu Trp Ile
        35                  40                  45

Gly Tyr Val Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Gly Gly Tyr Asp Phe Trp Ser Gly Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140
```

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Asp Glu Leu Asp Glu Gly Pro Val Ser Leu Thr Cys Leu
        355                 360                 365

Val Lys Gly Phe Tyr Pro Ser Asp Ile Ala Val Glu Trp Glu Ser Thr
370                 375                 380

Tyr Gly Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Ser Tyr Trp Arg
                405                 410                 415

Trp Val Lys Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 44
<211> LENGTH: 448
<212> TYPE: PRT
<213> ORGANISM: Artificial Sequence
<220> FEATURE:
<223> OTHER INFORMATION: mAb2 FI/FS1-65 heavy chain

<400> SEQUENCE: 44

Gln Val Gln Leu Val Gln Pro Gly Ala Glu Val Lys Lys Pro Gly Thr
1               5                   10                  15

Ser Val Lys Leu Ser Cys Lys Ala Ser Gly Tyr Thr Phe Thr Thr Tyr
                20                  25                  30

Trp Met His Trp Val Arg Gln Ala Pro Gly Gln Gly Leu Glu Trp Ile
            35                  40                  45

Gly Glu Ile Asn Pro Thr Asn Gly His Thr Asn Tyr Asn Gln Lys Phe
        50                  55                  60

Gln Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Val Gly Ser Ile Phe Asp Tyr Trp Gly Gln Gly Thr
            100                 105                 110

Leu Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Asp Glu Gly Gly Pro Val Ser Leu Thr
        355                 360                 365

Cys Leu Val Lys Gly Phe Tyr Pro Ser Asp Ile Ala Val Glu Trp Glu
    370                 375                 380

Ser Thr Tyr Gly Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Ser Tyr
                405                 410                 415

Trp Arg Trp Val Lys Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 45
<211> LENGTH: 445
<212> TYPE: PRT
<213> ORGANISM: Artificial Sequence
<220> FEATURE:
<223> OTHER INFORMATION: mAb2 RI/FS1-67 heavy chain

<400> SEQUENCE: 45

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ile Tyr
            20                  25                  30

Tyr Trp Ser Trp Ile Arg Gln Pro Pro Gly Lys Gly Leu Glu Trp Ile
        35                  40                  45

Gly Tyr Val Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Gly Gly Tyr Asp Phe Trp Ser Gly Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Asp Glu Thr Asp Gly Pro Val Ser Leu Thr Cys Leu Val
        355                 360                 365

Lys Gly Phe Tyr Pro Ser Asp Ile Ala Val Glu Trp Glu Ser Thr Tyr
    370                 375                 380

Gly Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Ser Tyr Trp Arg Trp
```

```
                    405                 410                 415
Tyr Lys Gly Asn Val Phe Ser Cys Ser Val Met His Glu Ala Leu His
                420                 425                 430

Asn His Tyr Thr Gln Lys Ser Leu Ser Leu Ser Pro Gly
            435                 440                 445

<210> SEQ ID NO 46
<211> LENGTH: 447
<212> TYPE: PRT
<213> ORGANISM: Artificial Sequence
<220> FEATURE:
<223> OTHER INFORMATION: mAb2 FI/FS1-67 heavy chain

<400> SEQUENCE: 46

Gln Val Gln Leu Val Gln Pro Gly Ala Glu Val Lys Lys Pro Gly Thr
1               5                   10                  15

Ser Val Lys Leu Ser Cys Lys Ala Ser Gly Tyr Thr Phe Thr Thr Tyr
                20                  25                  30

Trp Met His Trp Val Arg Gln Ala Pro Gly Gln Gly Leu Glu Trp Ile
            35                  40                  45

Gly Glu Ile Asn Pro Thr Asn Gly His Thr Asn Tyr Asn Gln Lys Phe
        50                  55                  60

Gln Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Val Gly Ser Ile Phe Asp Tyr Trp Gly Gln Gly Thr
            100                 105                 110

Leu Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
```

```
                325                 330                 335
Ile Ser Lys Ala Lys Gly Gln Pro Arg Glu Pro Gln Val Tyr Thr Leu
            340                 345                 350

Pro Pro Ser Arg Asp Glu Thr Asp Asp Gly Pro Val Ser Leu Thr Cys
            355                 360                 365

Leu Val Lys Gly Phe Tyr Pro Ser Asp Ile Ala Val Glu Trp Glu Ser
            370                 375                 380

Thr Tyr Gly Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Ser Tyr Trp
                405                 410                 415

Arg Trp Tyr Lys Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 47
<211> LENGTH: 222
<212> TYPE: PRT
<213> ORGANISM: Artificial Sequence
<220> FEATURE:
<223> OTHER INFORMATION: human IgG1 Fc fragment (wildtpe [WT] Fcab)

<400> SEQUENCE: 47

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly
    210                 215                 220

<210> SEQ ID NO 48
<211> LENGTH: 15
<212> TYPE: PRT
```

<213> ORGANISM: Artificial Sequence
<220> FEATURE:
<223> OTHER INFORMATION: human IgG1 hinge region

<400> SEQUENCE: 48

Glu Pro Lys Ser Cys Asp Lys Thr His Thr Cys Pro Pro Cys Pro
1               5                   10                  15

<210> SEQ ID NO 49
<211> LENGTH: 6
<212> TYPE: PRT
<213> ORGANISM: Artificial Sequence
<220> FEATURE:
<223> OTHER INFORMATION: truncated human IgG1 hinge region

<400> SEQUENCE: 49

Thr Cys Pro Pro Cys Pro
1               5

<210> SEQ ID NO 50
<211> LENGTH: 219
<212> TYPE: PRT
<213> ORGANISM: Artificial Sequence
<220> FEATURE:
<223> OTHER INFORMATION: 9D9 light chain

<400> SEQUENCE: 50

Asp Ile Val Met Thr Gln Thr Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 51
<211> LENGTH: 657
<212> TYPE: DNA
<213> ORGANISM: Artificial Sequence

```
<220> FEATURE:
<223> OTHER INFORMATION: 9D9 light chain

<400> SEQUENCE: 51
gacatcgtga tgacccagac caccctgagc ctgcccgtga gcctgggcga ccaggccagc      60
atcagctgca gaagcagcca gagcatcgtg cacagcaacg gcaacaccta cctggagtgg     120
tacctgcaga gcccggcca gagccccaag ctgctgatct acaaggtgag caacagattc      180
agcggcgtgc ccgacagatt cagcggcagc ggcagcggca ccgacttcac cctgaagatc     240
agcagagtgg aggccgagga cctgggcgtg tactactgct ccagggcag ccacgtgccc      300 tacaccttcg gcggcggcac caagctggag atcaagagag ccgacgccgc ccccaccgtg     360
agcatcttcc cccccagcag cgagcagctg accagcggcg gcgccagcgt ggtgtgcttc     420
ctgaacaact ctacccccaa ggacatcaac gtgaagtgga gatcgacgg cagcgagaga      480 cagaacggcg tgctgaacag ctggaccgac caggacagca aggacagcac ctacagcatg     540
agcagcaccc tgaccctgac caaggacgag tacgagagac acaacagcta cctgcgag      600 gccacccaca gaccagcac cagccccatc gtgaagagct tcaacagaaa cgagtgc        657

<210> SEQ ID NO 52
<211> LENGTH: 447
<212> TYPE: PRT
<213> ORGANISM: Artificial Sequence
<220> FEATURE:
<223> OTHER INFORMATION: 9D9m2a heavy chain

<400> SEQUENCE: 52

Glu Ile Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Asp Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Tyr Gly Ser Trp Phe Ala Tyr Trp Gly Gln Gly Thr Leu
            100                 105                 110

Ile Thr Val Ser Thr Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220
```

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
            245                 250                 255

Pro Ile Val Thr Cys Val Val Val Asp Val Ser Glu Asp Asp Pro Asp
        260                 265                 270

Val Gln Ile Ser Trp Phe Val Asn Asn Val Glu Val His Thr Ala Gln
    275                 280                 285

Thr Gln Thr His Arg Glu Asp Tyr Asn Ser Thr Leu Arg Val Val Ser
290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
            325                 330                 335

Ser Lys Pro Lys Gly Ser Val Arg Ala Pro Gln Val Tyr Val Leu Pro
        340                 345                 350

Pro Pro Glu Glu Glu Met Thr Lys Lys Gln Val Thr Leu Thr Cys Met
    355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
            405                 410                 415

Trp Val Glu Arg Asn Ser Tyr Ser Cys Ser Val Val His Glu Gly Leu
        420                 425                 430

His Asn His His Thr Thr Lys Ser Phe Ser Arg Thr Pro Gly Lys
    435                 440                 445

<210> SEQ ID NO 53
<211> LENGTH: 1341
<212> TYPE: DNA
<213> ORGANISM: Artificial Sequence
<220> FEATURE:
<223> OTHER INFORMATION: 9D9m2a heavy chain

<400> SEQUENCE: 53
gagatccagc tgcagcagag cggcccccgtg ctggtgaagc cggcgccag cgtgaagatg     60 agctgcaagg ccagcggcta caccttcacc gactactaca tgaactgggt gaagcagagc    120
cacggcaaga gcctggagtg gatcggcgtg atcaaccccct acaacggcga caccagctac    180
aaccagaagt tcaagggcaa ggccaccctg accgtggaca gagcagcag caccgcctac    240 atggagctga cagcctgac cagcgaggac agcgccgtgt actactgcgc cagatactac    300
ggcagctggt tcgcctactg gggccagggc accctgatca ccgtgagcac cgccaagacc    360
accgccccca gcgtgtaccc cctggccccc gtgtgcggcg acaccaccgg cagcagcgtg    420
accctgggct gcctggtgaa gggctacttc cccgagcccg tgaccctgac ctggaacagc    480
ggcagcctga gcagcggcgt gcacaccttc cccgccgtgc tgcagagcga cctgtacacc    540
ctgagcagca gcgtgaccgt gaccagcagc acctggccca gcagagcat cacctgcaac    600 gtggcccacc ccgccagcag caccaaggtg gacaagaaga tcgagcccag gcccccacc    660 atcaagccct gcccccctg caagtgcccc gccccaacc tgctggggcgg cccagcgtg    720 ttcatcttcc cccccaagat caaggacgtg ctgatgatca gcctgagccc catcgtgacc    780
tgcgtggtgg tggacgtgag cgaggacgac cccgacgtgc agatcagctg gttcgtgaac    840

-continued

```
aacgtggagg tgcacaccgc ccagacccag acccacagag aggactacaa cagcaccctg    900
agagtggtga gcgccctgcc catccagcac caggactgga tgagcggcaa ggagttcaag    960
tgcaaggtga acaacaagga cctgcccgcc cccatcgaga gaaccatcag caagcccaag   1020
ggcagcgtga gaccccccca ggtgtacgtg ctgccccccc ccgaggagga tgaccaag     1080 aagcaggtga ccctgacctg catggtgacc gacttcatgc ccgaggacat ctacgtggag   1140
tggaccaaca acggcaagac cgagctgaac tacaagaaca ccgagcccgt gctggacagc   1200
gacggcagct acttcatgta cagcaagctg agagtggaga agaagaactg ggtggagaga   1260
aacagctaca gctgcagcgt ggtgcacgag ggcctgcaca accaccacac caccaagagc   1320
ttcagcagaa ccccggcaa g                                              1341
```

<210> SEQ ID NO 54
<211> LENGTH: 445
<212> TYPE: PRT
<213> ORGANISM: Artificial Sequence
<220> FEATURE:
<223> OTHER INFORMATION: 9D9h1 heavy chain

<400> SEQUENCE: 54

```
Glu Ile Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Asp Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Tyr Gly Ser Trp Phe Ala Tyr Trp Gly Gln Gly Thr Leu
            100                 105                 110

Ile Thr Val Ser Thr Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 55
<211> LENGTH: 1338
<212> TYPE: DNA
<213> ORGANISM: Artificial Sequence
<220> FEATURE:
<223> OTHER INFORMATION: 9D9h1 heavy chain

<400> SEQUENCE: 55

```
gagatccagc tgcagcagag cggccccgtg ctggtgaagc ccggcgccag cgtgaagatg      60
agctgcaagg ccagcggcta caccttcacc gactactaca tgaactgggt gaagcagagc     120
cacggcaaga gcctggagtg gatcggcgtg atcaaccccc tacaacggcga caccagctac     180 aaccagaagt tcaagggcaa ggccaccctg accgtggaca gagcagcag caccgcctac      240 atggagctga cagcctgac cagcgaggac agcgccgtgt actactgcgc cagatactac      300
ggcagctggt tcgcctactg gggccagggc accctgatca ccgtgagcac cgccaagacc     360
accgccccca gcgtgtaccc cctggccccc gtgtgcggcg acaccaccgg cagcagcgtg     420
accctgggct gcctggtgaa gggctacttc cccgagcccg tgaccctgac ctggaacagc     480
ggcagcctga gcagcggcgt gcacaccttc cccgccgtgc tgcagagcga cctgtacacc     540
ctgagcagca gcgtgaccgt gaccagcagc acctggccca gccagagcat cacctgcaac     600
gtggcccacc ccgccagcag caccaaggtg acaagaaga tcgagcccaa gagctgcgac     660
aagacccaca cctgcccccc ctgccccgcc ccgagctgc tgggcggccc cagcgtgttc     720
ctgttccccc caagcccaa ggacaccctg atgatcagca gaaccccga ggtgacctgc      780 gtggtggtgg acgtgagcca cgaggacccc gaggtgaagt tcaactggta cgtggacggc     840
gtggaggtgc acaacgccaa gaccaagccc agagaggagc agtacaacag cacctacaga     900
gtggtgagcg tgctgaccgt gctgcaccag gactggctga acggcaagga gtacaagtgc     960
aaggtgagca caaggccct gccgccccc atcgagaaga ccatcagcaa ggccaagggc     1020
cagcccagag agccccaggt gtacaccctg ccccccagca gagacgagct gaccaagaac    1080
```
caggtgagcc tgacctgcct ggtgaagggc ttctacccca gcgacatcgc cgtggagtgg        1140
gagagcaacg gccagcccga gaacaactac aagaccaccc ccccgtgct ggacagcgac        1200 ggcagcttct tcctgtacag caagctgacc gtggacaaga gcagatggca gcagggcaac        1260
gtgttcagct gcagcgtgat gcacgaggcc ctgcacaacc actacaccca gaagagcctg        1320
agcctgagcc ccggcaag                                                      1338

```
<210> SEQ ID NO 56
<211> LENGTH: 445
<212> TYPE: PRT
<213> ORGANISM: Artificial Sequence
<220> FEATURE:
<223> OTHER INFORMATION: 9D9/FS1-67 heavy chain

<400> SEQUENCE: 56
```

Glu Ile Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Tyr Gly Ser Trp Phe Ala Tyr Trp Gly Gln Gly Thr Leu
            100                 105                 110

Ile Thr Val Ser Thr Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys

```
             305                 310                 315                 320
Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Thr Asp Asp Gly Pro Val Ser Leu Thr Cys Leu Val
                355                 360                 365

Lys Gly Phe Tyr Pro Ser Asp Ile Ala Val Glu Trp Glu Ser Thr Tyr
            370                 375                 380

Gly Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Ser Tyr Trp Arg Trp
                405                 410                 415

Tyr Lys Gly Asn Val Phe Ser Cys Ser Val Met His Glu Ala Leu His
                420                 425                 430

Asn His Tyr Thr Gln Lys Ser Leu Ser Leu Ser Pro Gly
            435                 440                 445
```

<210> SEQ ID NO 57
<211> LENGTH: 1335
<212> TYPE: DNA
<213> ORGANISM: Artificial Sequence
<220> FEATURE:
<223> OTHER INFORMATION: 9D9/FS1-67 heavy chain

<400> SEQUENCE: 57

```
gagatccagc tgcagcagag cggccccgtg ctggtgaagc ccggcgccag cgtgaagatg      60
agctgcaagg ccagcggcta caccttcacc gactactaca tgaactgggt gaagcagagc     120
cacggcaaga gcctggagtg gatcggcgtg atcaaccct acaacggcga caccagctac      180
aaccagaagt tcaagggcaa ggccaccctg accgtggaca gagcagcag caccgcctac      240
atggagctga cagcctgac cagcgaggac agcgccgtgt actactgcgc cagatactac      300
ggcagctggt tcgcctactg gggccagggc accctgatca ccgtgagcac cgccaagacc     360
accgccccca gcgtgtaccc cctggccccc gtgtgcggcg acaccaccgg cagcagcgtg     420
accctgggct gcctggtgaa gggctacttc cccgagcccg tgaccctgac ctggaacagc     480
ggcagcctga gcgcggcgt gcacaccttc cccgccgtgc tgcagagcga cctgtacacc     540
ctgagcagca gcgtgaccgt gaccagcagc acctggccca gcagagcat acctgcaac      600
gtggcccacc ccgccagcag caccaaggtg gacaagaaga tcgagcccaa gagctgcgac     660
aagacccaca cctgcccccc ctgccccgcc ccgagctgc tgggcggccc cagcgtgttc     720
ctgttcccc ccaagcccaa ggacaccctg atgatcagca gaacccccga ggtgacctgc      780
gtggtggtgg acgtgagcca cgaggacccc gaggtgaagt tcaactggta cgtggacggc     840
gtggaggtgc acaacgccaa gaccaagccc agagaggagc agtacaacag cacctacaga     900
gtggtgagcg tgctgaccgt gctgcaccag gactggctga acggcaagga gtacaagtgc     960
aaggtgagca acaaggccct gcccgccccc atcgagaaga ccatcagcaa ggccaagggc    1020
cagcccagag agccccaggt gtacaccctg cccccagca gagacgagac cgacgacggc      1080
cccgtgagcc tgacctgcct ggtgaagggc ttctacccca gcgacatcgc cgtggagtgg    1140
gagagcacct acggccccga gaacaactac aagaccaccc ccccgtgct ggacagcgac      1200
ggcagcttct tcctgtacag caagctgacc gtgagctact ggagatggta caagggcaac    1260
gtgttcagct gcagcgtgat gcacgaggcc ctgcacaacc actacaccca gaagagcctg    1320
```

```
agcctgagcc ccggc                                                       1335
```

<210> SEQ ID NO 58
<211> LENGTH: 215
<212> TYPE: PRT
<213> ORGANISM: Artificial Sequence
<220> FEATURE:
<223> OTHER INFORMATION: Ipilimumab light chain

<400> SEQUENCE: 58

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 59
<211> LENGTH: 645
<212> TYPE: DNA
<213> ORGANISM: Artificial Sequence
<220> FEATURE:
<223> OTHER INFORMATION: Ipilimumab light chain

<400> SEQUENCE: 59

```
gacatccaga tgacccagag ccccggcacc ctgagcctga gccccggcga gagagccacc    60
ctgagctgca gagccagcca gagcgtgggc agcagctacc tggcctggta ccagcagaag   120
cccggccagg cccccagact gctgatctac ggcgccttca gcagagccac cggcatcccc   180
gacagattca gcggcagcgg cagcggcacc gacttcaccc tgaccatcag cagactggag   240
cccgaggact tcgccgtgta ctactgccag cagtacggca gcagcccctg gaccttcggc   300
cagggcacca aggtggagat caagagaacc gtggccgccc ccagcgtgtt catcttcccc   360
cccagcgacg agcagctgaa gagcggcacc gccagcgtgg tgtgcctgct gaacaacttc   420
```

-continued

```
taccccagag aggccaaggt gcagtggaag gtggacaacg ccctgcagag cggcaacagc      480
caggagagcg tgaccgagca ggacagcaag gacagcacct acagcctgag cagcaccctg      540
accctgagca aggccgacta cgagaagcac aaggtgtacg cctgcgaggt gacccaccag      600
ggcctgagca gccccgtgac caagagcttc aacagaggcg agtgc                      645
```

<210> SEQ ID NO 60
<211> LENGTH: 443
<212> TYPE: PRT
<213> ORGANISM: Artificial Sequence
<220> FEATURE:
<223> OTHER INFORMATION: Ipilimumab heavy chain

<400> SEQUENCE: 60

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
```

```
                        325                 330                 335
Lys Gly Gln Pro Arg Glu Pro Gln Val Tyr Thr Leu Pro Pro Ser Arg
                340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 61
<211> LENGTH: 1332
<212> TYPE: DNA
<213> ORGANISM: Artificial Sequence
<220> FEATURE:
<223> OTHER INFORMATION: Ipilimumab heavy chain

<400> SEQUENCE: 61
caggtgcagc tggtggagag cggcggcggc gtggtgcagc ccggcagaag cctgagactg      60
agctgcgccg ccagcggctt caccttcagc agctacacca tgcactgggt gagacaggcc    120
cccggcaagg gcctggagtg ggtgaccttc atcagctacg acggcaacaa caagtactac    180
gccgacagcg tgaagggcag attcaccatc agcagagaca cagcaagaa caccctgtac    240 ctgcagatga cagcctgag agccgaggac accgccatct actactgcgc cagaaccggc    300
tggctgggcc ccttcgacta ctggggccag ggcaccctgg tgaccgtgag cagcgccagc    360
accaagggcc ccagcgtgtt ccccctggcc ccagcagca gagcaccag cggcggcacc    420 gccgccctgg gctgcctggt gaaggactac ttccccgagc ccgtgaccgt gagctggaac    480
agcggcgccc tgaccagcgg cgtgcacacc ttccccgccg tgctgcagag cagcggcctg    540
tacagcctga gcagcgtggt gaccgtgccc agcagcagcc tgggcaccca gacctacatc    600
tgcaacgtga accacaagcc cagcaacacc aaggtggaca gaaaggtgga gagaaagtgc    660
tgcgtggagt gccccccctg ccccgccccc ccgtggccg gccccagcgt gttcctgttc    720 cccccaagc caaggacac cctgatgatc agcagaaccc ccgaggtgac ctgcgtggtg    780
gtggacgtga gccacgagga ccccgaggtg aagttcaact ggtacgtgga cggcgtggag    840
gtgcacaacg ccaagaccaa gcccagagag gagcagtaca acagcaccta cagagtggtg    900
agcgtgctga ccgtgctgca ccaggactgg ctgaacggca aggagtacaa gtgcaaggtg    960
agcaacaagg ccctgcccgc ccccatcgag aagaccatca gcaaggccaa gggccagccc   1020
agagagcccc aggtgtacac cctgcccccc agcagagacg agctgaccaa gaaccaggtg   1080
agcctgacct gcctggtgaa gggcttctac cccagcgaca tcgccgtgga gtgggagagc   1140
aacggccagc ccgagaacaa ctacaagacc accccccccg tgctggacag cgacggcagc   1200
ttcttcctgt acagcaagct gaccgtggac aagagcagat ggcagcaggg caacgtgttc   1260
agctgcagcg tgatgcacga ggccctgcac aaccactaca cccagaagag cctgagcctg   1320
agccccggca ag                                                      1332
```

```
<210> SEQ ID NO 62
<211> LENGTH: 5
<212> TYPE: PRT
<213> ORGANISM: Artificial Sequence
<220> FEATURE:
<223> OTHER INFORMATION: HuL2G7 CDR1 VH

<400> SEQUENCE: 62

Gly Asn Trp Ile Glu
1               5

<210> SEQ ID NO 63
<211> LENGTH: 17
<212> TYPE: PRT
<213> ORGANISM: Artificial Sequence
<220> FEATURE:
<223> OTHER INFORMATION: HuL2G7 CDR2 VH

<400> SEQUENCE: 63

Glu Ile Leu Pro Gly Ser Asn Thr Asn Tyr Asn Glu Phe Lys Phe Lys
1               5                   10                  15

Gly

<210> SEQ ID NO 64
<211> LENGTH: 11
<212> TYPE: PRT
<213> ORGANISM: Artificial Sequence
<220> FEATURE:
<223> OTHER INFORMATION: HuL2G7 CDR3 VH

<400> SEQUENCE: 64

Gly Gly His Tyr Tyr Gly Ser Ser Trp Asp Tyr
1               5                   10

<210> SEQ ID NO 65
<211> LENGTH: 11
<212> TYPE: PRT
<213> ORGANISM: Artificial Sequence
<220> FEATURE:
<223> OTHER INFORMATION: HuL2G7 CDR1 VL

<400> SEQUENCE: 65

Lys Ala Ser Glu Asn Val Val Thr Tyr Val Ser
1               5                   10

<210> SEQ ID NO 66
<211> LENGTH: 7
<212> TYPE: PRT
<213> ORGANISM: Artificial Sequence
<220> FEATURE:
<223> OTHER INFORMATION: HuL2G7 CDR2 VL

<400> SEQUENCE: 66

Gly Ala Ser Asn Arg Tyr Thr
1               5

<210> SEQ ID NO 67
<211> LENGTH: 9
<212> TYPE: PRT
<213> ORGANISM: Artificial Sequence
<220> FEATURE:
<223> OTHER INFORMATION: HuL2G7 CDR3 VL

<400> SEQUENCE: 67

Gly Gln Gly Tyr Ser Tyr Pro Tyr Thr
1               5
```

<210> SEQ ID NO 68
<211> LENGTH: 108
<212> TYPE: PRT
<213> ORGANISM: Artificial Sequence
<220> FEATURE:
<223> OTHER INFORMATION: Fcab FS1-60 CH3 domain comprising a C-terminal
      lysine

<400> SEQUENCE: 68

Gly Gln Pro Arg Glu Pro Gln Val Tyr Thr Leu Pro Pro Ser Arg Asp
1               5                   10                  15

Glu Leu Asp Glu Gly Gly Pro Val Ser Leu Thr Cys Leu Val Lys Gly
            20                  25                  30

Phe Tyr Pro Ser Asp Ile Ala Val Glu Trp Glu Ser Thr Tyr Gly Pro
        35                  40                  45

Glu Asn Asn Tyr Lys Thr Thr Pro Pro Val Leu Asp Ser Asp Gly Ser
    50                  55                  60

Phe Phe Leu Tyr Ser Arg Leu Thr Val Ser His Trp Arg Trp Tyr Ser
65                  70                  75                  80

Gly Asn Val Phe Ser Cys Ser Val Met His Glu Ala Leu His Asn His
                85                  90                  95

Tyr Thr Gln Lys Ser Leu Ser Leu Ser Pro Gly Lys
            100                 105

<210> SEQ ID NO 69
<211> LENGTH: 41
<212> TYPE: DNA
<213> ORGANISM: Artificial Sequence
<220> FEATURE:
<223> OTHER INFORMATION: Primer 07 CH3 new

<400> SEQUENCE: 69
cacagtgcac agcctcgaga accacaggtg tacaccctgc c                    41

<210> SEQ ID NO 70
<211> LENGTH: 23
<212> TYPE: DNA
<213> ORGANISM: Artificial Sequence
<220> FEATURE:
<223> OTHER INFORMATION: Primer Shuff Rev 3

<400> SEQUENCE: 70
gagcttgctg tagaggaaga agg                                        23

<210> SEQ ID NO 71
<211> LENGTH: 34
<212> TYPE: DNA
<213> ORGANISM: Artificial Sequence
<220> FEATURE:
<223> OTHER INFORMATION: Primer 03 CH3 new

<400> SEQUENCE: 71
gcttgcggcc gctttacccg gagacaggga gagg                            34

<210> SEQ ID NO 72
<211> LENGTH: 22
<212> TYPE: DNA
<213> ORGANISM: Artificial Sequence
<220> FEATURE:
<223> OTHER INFORMATION: Primer Shuff For1

<400> SEQUENCE: 72
gcctggtcaa aggcttctat cc                                             22

EGFR BINDING MOLECULES

CROSS REFERENCE TO RELATED APPLICATIONS

This is the U.S. National Stage of International Application No. PCT/EP2017/068261, filed Jul. 19, 2017, which was published in English under PCT Article 21(2), which in turn claims priority from GB 1612520.5, filed on Jul. 19, 2016, which is hereby incorporated by reference in its entirety.

FIELD OF THE INVENTION

The present invention relates to specific binding members which bind the human epidermal growth factor receptor (EGFR). The specific binding members preferably comprise an EGFR antigen-binding site which may be located in two or more structural loops of a CH3 domain of the specific binding member. The specific binding members of the invention are useful in the treatment of cancers expressing EGFR.

BACKGROUND TO THE INVENTION

Epidermal growth factor receptor (EGFR; also referred to as ErbB-1 and HER1) is the cell-surface receptor for members of the epidermal growth factor family (EGF-family) of extracellular protein ligands. EGFR is a large, monomeric glycoprotein with a single transmembrane region and a cytoplasmic tyrosine kinase domain flanked by noncatalytic regulatory regions. Sequence analyses have shown that the ectodomain contains four sub-domains, termed L1, CR1, L2 and CR2, where L and CR are acronyms for large and Cys-rich respectively. The L1 and L2 domains have also been referred to as domains I and III, respectively. The CR domains have been previously referred to as domains II and IV, or as S1.1-S1.3 and S2.1-S2.3 where S is an abbreviation for small.

Cancers which are known to express EGFR include lung cancer (for example, non-small cell lung cancer [NSCLC]) (Pao et al, 2010; Amman et al, 2005), glioblastoma multiforme (Taylor et al, 2102), skin cancer (for example, cutaneous squamous cell carcinoma) (Uribe et al, 2011), head and neck cancer (such as head and neck squamous-cell carcinoma [HNSCC]) (Zimmermann et al, 2006; Smilek et al, 2012), breast cancer (Masuda et al, 2013), stomach cancer (gastric cancer) (Terashima et al, 2012), colorectal cancer (CRC) (Spano et al, 2005; Saletti et al, 2015), ovarian cancer (Hudson et al, 2009), pancreatic cancer (Troiani et al, 2012), or endometrial cancer (Scambia et al, 1994).

Monoclonal antibodies to the extra-cellular domain of EGFR have been described. These antibodies disrupt ligand binding to EGFR and subsequent signal transduction.

mAbC225 (ERBITUX*/cetuximab) is a chimeric IgG1 antibody which binds to the extracellular domain of EGFR and competes with EGF for binding to EGFR, thereby inhibiting downstream pathway signaling and blocking proliferation of tumour cells (Voigt et al, 2012). Cetuximab is FDA approved for the treatment of head and neck cancer, specifically locally or regionally advanced squamous cell carcinoma of the head and neck in combination with radiation therapy, recurrent locoregional disease or metastatic squamous cell carcinoma of the head and neck in combination with platinum-based therapy with 5-FU, and recurrent or metastatic squamous cell carcinoma of the head and neck progressing after platinum-based therapy. Cetuximab is also FDA approved for the treatment of KRAS mutation-negative (wild-type) EGFR-expressing, metastatic colorectal cancer as determined by FDA approved tests, in particular as a first-line treatment in combination with FOLFIRI, or in combination with irinotecan in patients who are refractory to irinotecan-based chemotherapy, and for the treatment of patients who have failed oxaliplatin- and irinotecan-based chemotherapy or who are intolerant to irinotecan as a single agent.

ABX-EGF (VECTIBIX®/panitumumab) is a human IgG2 antibody which, like cetuximab, binds to the extracellular domain of EGFR and competes with EGF for binding to EGFR, thereby inhibiting downstream pathway signaling and blocking proliferation of tumour cells (Voigt et al, 2012). Panitumumab is approved by the FDA for the treatment of patients with wild-type KRAS (exon 2 in codons 12 or 13) metastatic colorectal cancer (mCRC) as determined by an FDA-approved test, either as a first-line therapy in combination with FOLFOX or as a monotherapy following disease progression after prior treatment with fluoropyrimidine-, oxaliplatin-, and irinotecan-containing chemotherapy.

Necitumumab (Portrazza™) is another antibody that binds EGFR and was approved by the FDA in 2015 for use in combination with gemcitabine and cisplatin for first-line treatment of patients with metastatic squamous non-small cell lung cancer.

Nimotuzumab (previously known as h-R3) is a humanised IgG1 antibody that binds to the extracellular region of EGFR which is enrolled in clinical trials in a number of countries.

Nimotuzumab has been approved for treatment of squamous cell carcinoma in head and neck in India, Cuba, Argentina, Colombia, Ivory Coast, Gabon, Ukraine, Peru and Sri Lanka; as well as for the treatment of glioma (pediatric and adult) in Cuba, Argentina, Philippines and Ukraine; and for the treatment of nasopharyngeal cancer in China (Ramakrishnan et al, 2009).

Clinical testing of other antibodies targeting EGFR, including zalutuzumab (HuMax-EGFr) and matuzumab (formerly EMD 72000), has been initiated but these antibodies have not been granted regulatory approval and development has since stopped.

A number of small molecule inhibitors of EGFR have also been approved for the treatment of cancer, including erlotinib (TARCEVA®) and gefitinib (IRESSA®).

While there has been some success with single-agent EGFR-targeting therapies in treating cancers, many tumours acquire resistance to the monotherapy following treatment. Cross-talk between EGFR and other molecules on the tumour cell surface has been identified as a potential mechanism by which these tumours become resistant to treatment. For example, EGFR-c-Met cross talk has been found in a number of tumour types, including glioblastoma, NSCLC, colorectal and gastric cancers, resulting in an escape mechanism for tumours to EGFR-targeted single-agent therapies. Since increased HGF/c-Met signalling can limit the effect of EGFR pathway inhibition it has been linked with acquired resistance to EGFR-targeted drugs. Perturbation of both receptors' activity suggests that their signalling is highly and dynamically interconnected (Castoldi et al, 2013).

c-Met (MET receptor, HGFR, c-MET in humans) is a receptor tyrosine kinase (RTK) which is found on the surface of many tumour cells, including those which also express EGFR. Hepatocyte Growth Factor (HGF), also known as scatter factor (SF), is the only known ligand of c-Met. HGF is secreted by mesenchymal cells and acts as a multi-functional cytokine on cells of mainly epithelial origin, through its receptor c-Met on the cell surface. It is secreted as a single inactive polypeptide and is cleaved by serine proteases into a 69 kDa alpha-chain and 34 kDa beta chain linked by disulphide bonds to create a heterodimeric active molecule (Naldini et al, 1992). HGF has a high affinity binding site for c-Met and a low affinity binding site for heparin sulphate proteoglycans.

HGF plays a role in angiogenesis and promotes cell proliferation, survival, motility, scattering differentiation and morphogenesis in numerous cell and tissue types (Organ et al, 2011).

Binding of HGF to its receptor c-Met induces homodimerization and tyrosine phosphorylation of c-Met, resulting in its activation and downstream signalling common to many RTKs. In vivo, the c-Met/HGF signalling pathway plays a role in neural induction, liver regeneration, wound angiogenesis, growth, invasion, morphologic differentiation and normal embryological development. The c-Met/HGF pathway also plays an important role in cancers through the activation of key oncogenic pathways (including RAS, PI3K, STAT-3 and beta catenin). Aberrant signalling via this pathway has been shown to be involved in tumourigenesis, particularly in the development of invasive and metastatic cancer phenotypes. Autocrine stimulation of c-Met is most commonly seen in gliomas, osteosarcoma, pancreatic cancers and gastric cancers (Stone et al, 2014).

Small molecule kinase inhibitors, which affect the c-Met pathway by binding to c-Met as well as other RTKs, have been tested in the clinic. Cobazantinib and crizotinib have been approved by the FDA, while others tested in the clinic include tivatinib and foretinib.

Antibodies which bind to c-Met or HGF have also undergone clinical testing, including onartuzumab (MetMab). Onartuzumab is an anti-c-Met humanized monovalent monoclonal antibody that blocks binding of HGF to c-Met. Anti-HGF antibodies, which block binding of HGF to c-Met, have also been tested in clinical trials, and include rilotumumab, ficlatuzumab and HuL2G7. However, none of these antibodies have been approved for clinical use.

Rilotumumab (formerly known as AMG102) is a fully human IgG2 monoclonal antibody that binds to and neutralizes HGF, blocking its binding to c-Met. Clinical trials of rilotumumab in advanced gastric cancer were halted after a significantly worse overall survival and worse toxicity resulting in an increase in deaths of patients was observed in patients treated with rilotumumab plus chemotherapy (epirubicin, cisplatin and capecitabine (ECX)) compared with patients given chemotherapy alone.

Ficlatuzumab (formerly known as AV-299) is a humanized IgG1 monoclonal antibody that binds to HGF and, like rilotumumab, neutralizes binding to c-Met. Clinical trials are ongoing to evaluate ficlatuzumab in combination with cetuximab in patients with recurrent/metastatic HNSCC. In addition, treatment with ficlatuzumab plus erlotinib in patients with previously untreated metastatic EGFR-mutated non-small cell lung cancer (NSCLC) and BDX004 positive label is also being investigated. Clinical testing of ficlatuzumab in combination with high dose cytarabine in relapsed and refractory acute myeloid leukaemia patients is also underway. Studies evaluating ficlatuzumab, cisplatin and intensity-modulated radiotherapy (IMRT) have been suspended. A randomised phase 2 study of geftinib alone or in combination with ficlatuzumab in Asian patients with previously untreated lung adenocarcinoma (with or without EGFR mutations) failed to demonstrate improved overall survival or progression-free survival.

HuL2G7 (formerly known as TAK-701) is a humanized monoclonal antibody that effectively neutralized HGF and was tested in a phase 1 study in advanced non-haematologic malignancies but does not appear to have progressed into further development.

The preparation of specific binding members comprising an antigen-binding site engineered into one or more structural loops of an antibody domain, such as a constant or variable domain of the antibody is described in WO2006/072620, WO2009/132876, WO2009/000006 and EP2546268.

STATEMENTS OF THE INVENTION

As explained above, the use of EGFR-targeting single-agent therapies in the clinic has been limited due to the development of acquired resistance and subsequent recurrence of tumours, and the fact that no combination therapies targeting both EGFR and HGF have been approved for clinical use to date. There therefore is a need for therapeutic agents which inhibit both the EGFR and c-Met signalling pathways in order to block cross-talk and improve the efficacy of EGFR-targeting therapies.

Through an extensive screening and affinity maturation programme, the present inventors were able to identify three specific binding members comprising a binding site specific for EGFR in the CH3 domain of the molecule. These specific binding members can be advantageously incorporated into antibody molecules with a CDR-based binding site specific for a second tumour-associated antigen, to provide specific binding members with potent anti-tumour effects.

Skin toxicity has been observed with known anti-EGFR therapies resulting in e.g. skin rash and lesions. When incorporated into antibody molecules with a CDR-based binding site specific for a second antigen, in this case CTLA-4 or HGF, the specific binding members were found to advantageously elicit less skin toxicity in mice compared with the skin toxicity observed in mice treated with the specific binding member alone (see Example 18).

Thus, in a first aspect, the present invention provides a specific binding member which binds to EGFR, and comprises an EGFR antigen-binding site located in a CH3 domain of the specific binding member.

The EGFR antigen-binding site preferably comprises or contains the amino acid sequences:

```
(i)
                                          (SEQ ID NO: 1)
LDEGGP
and
                                          (SEQ ID NO: 3)
SHWRWYS;
(ii)
                                          (SEQ ID NO: 1)
LDEGGP
and
                                          (SEQ ID NO: 8)
SYWRWVK;
or
(iii)
                                          (SEQ ID NO: 13)
TDDGP
and
                                          (SEQ ID NO: 14)
SYWRWYK.
```

For example, the EGFR antigen-binding site may be located in a structural loop region of a CH3 domain of the specific binding member, wherein the structural loop region preferably comprises two or more structural loops, and wherein the EGFR antigen-binding site preferably comprises the amino acid sequences:

(i)
LDEGGP (SEQ ID NO: 1)
and
SHWRWYS; (SEQ ID NO: 3)

(ii)
LDEGGP (SEQ ID NO: 1)
and
SYWRWVK; (SEQ ID NO: 8)
or (iii)
TDDGP (SEQ ID NO: 13)
and
SYWRWYK. (SEQ ID NO: 14)

As a further example, the EGFR antigen-binding site may be engineered into two or more structural loops of a CH3 domain of the specific binding member, wherein the EGFR antigen-binding site preferably comprises the amino acid sequences:

(i)
LDEGGP (SEQ ID NO: 1)
and
SHWRWYS; (SEQ ID NO: 3)

(ii)
LDEGGP (SEQ ID NO: 1)
and
SYWRWVK; (SEQ ID NO: 8)
or (iii)
TDDGP (SEQ ID NO: 13)
and
SYWRWYK. (SEQ ID NO: 14)

The amino acid sequences set forth in a SEQ ID NOs 1 and 13 are preferably located in a first structural loop of the CH3 domain of the specific binding member, and the amino acid sequences set forth in SEQ ID NOs 3, 8 and 14 are preferably located in a second structural loop of the CH3 domain.

As mentioned above, the sequences of the EGFR antigen-binding site are preferably located in two or more structural loops of the CH3 domain of the specific binding member. In a preferred embodiment the EGFR antigen-binding site contains or comprises:

(i) the amino acid sequence set forth in SEQ ID NO: 1 in the AB loop, and/or the amino acid sequence set forth in SEQ ID NO: 3 in the EF loop of the CH3 domain;
(ii) the amino acid sequence set forth in SEQ ID NO: 1 in the AB loop, and/or the amino acid sequence set forth in SEQ ID NO: 8 in the EF loop of the CH3 domain; or
(iii) the amino acid sequence set forth in SEQ ID NO: 13 in the AB loop, and/or the amino acid sequence set forth in SEQ ID NO: 14 in the EF loop of the CH3 domain. More preferably, the EGFR antigen-binding site comprises the amino acid sequence set forth in SEQ ID NO: 1 in the AB loop, and the amino acid sequence set forth in SEQ ID NO: 3, or SEQ ID NO: 8 in the EF loop of the CH3 domain.

The EGFR antigen-binding site preferably further comprise the amino acid sequence TYG (SEQ ID NO: 2). This sequence is preferably located in a third structural loop of the CH3 domain, more preferably the CD loop of the CH3 domain.

The amino acid sequence set forth in SEQ ID NO: 1 is preferably located at residues (positions) 13.A to 18 of the CH3 domain; the amino acid sequence set forth in SEQ ID NO: 3 is preferably located at residues (positions) 92 to 98 of the CH3 domain of the specific binding member; the amino acid sequence set forth in SEQ ID NO: 8 is preferably located at residues (positions) 92 to 98 of the CH3 domain of the specific binding member; the amino acid sequence set forth in SEQ ID NO: 13 is preferably located at residues (positions) 14 to 18 of the CH3 domain, and the amino acid sequence set forth in SEQ ID NO: 14 is preferably located at residues (positions) 92 to 98 of the CH3 domain. The amino acid sequence set forth in SEQ ID NO: 2 is preferably located at residues (positions) 44 to 45.1 of the CH3 domain of the specific binding member. The residues of the specific binding members are numbered herein according to the IMGT (ImMunoGeneTics) numbering scheme.

In addition to the amino acid sequence set forth in SEQ ID NO: 1, and the amino acid sequence set forth in SEQ ID NO: 3, the specific binding member preferably comprises an arginine at residue (position) 88 of the CH3 domain.

The sequence of the CH3 domain of the specific binding member, other than the sequences of the EGFR antigen-binding site, is not particularly limited. Preferably, CH3 domain is a human immunoglobulin G domain, such as a human IgG1, IgG2, IgG3, or IgG4 CH3 domain, most preferably a human IgG1 CH3 domain. The sequences of human IgG1, IgG2, IgG3, or IgG4 CH3 domains are known in the art.

In a preferred embodiment, the specific binding member according to the present invention comprises the CH3 domain of SEQ ID NO: 4, SEQ ID NO: 9, or SEQ ID NO: 15. More preferably, a specific binding member of the invention comprises the CH3 domain of SEQ ID NO: 4 or 9.

The specific binding member may further comprise a CH2 domain. The CH2 domain is preferably located at the N-terminus of the CH3 domain of the specific binding member, as is the case in a human IgG molecule. The CH2 domain of the specific binding member is preferably the CH2 domain of human IgG1, IgG2, IgG3, or IgG4, more preferably the CH2 domain of human IgG1. The sequences of human IgG domains are known in the art. In a preferred embodiment, the specific binding member comprises an IgG CH2 domain with the sequence set forth in SEQ ID NO: 19.

A specific binding member of the invention preferably comprises the CH2 and CH3 domain sequence set forth in SEQ ID NO: 6, SEQ ID NO: 11, or SEQ ID NO: 17. More preferably, a specific binding of the invention comprises the CH2 and CH3 domain sequence set forth in SEQ ID NO: 6 or 11.

Preferably, the specific binding member comprises an immunoglobulin hinge region, or part thereof, at the N-terminus of the CH2 domain. The immunoglobulin hinge region preferably has the sequence set forth in SEQ ID NO: 48, or a fragment thereof, more preferably the sequence set forth in SEQ ID NO: 49.

A specific binding member of the invention may be a dimer consisting of two polypeptides, wherein each polypeptide has or comprises the CH2 and CH3 domain sequence set forth in SEQ ID NO: 6, SEQ ID NO: 11, or SEQ ID NO: 17, preferably SEQ ID NO: 6 or 11, and wherein each polypeptide further comprises an immunoglobulin hinge region, or part thereof, at the N-terminus of the CH2 domain, preferably the immunoglobulin hinge region set forth in SEQ ID NO: 49. These specific binding members are also referred to as FS1-60, FS1-65, and FS1-67, respectively, herein.

In addition to the EGFR antigen-binding site in the CH3 domain, the specific binding member of the invention may further comprise one or more additional antigen-binding sites to create a bi- or multi-specific molecule. Preferably, the specific binding member comprises a CDR-based antigen-binding site. CDR-based antigen binding sites are found in the variable regions of naturally-occurring immunoglobulin molecules and their structure is well-known in the art. Where the specific binding member comprises a CDR-based antigen binding site, the specific binding member is preferably an antibody molecule. The antibody molecule is not particularly limited, provided that it comprises a CH3 domain, as herein defined, and a CDR-based antigen-binding site. In a preferred embodiment, the antibody molecule is a human immunoglobulin G molecule, such as a human IgG1, IgG2, IgG3 or IgG4 molecule, more preferably a human IgG1 molecule. The sequences of human immunoglobulin G molecules are known in the art and introducing a CH3 domain or CH3 domain sequence as disclosed herein into such a molecule would not present any difficulty to the skilled person.

Where the specific binding member comprises one or more CDR-based antigen binding sites, the CDR-based antigen binding site preferably binds to a molecule which is a tumour-associated antigen. The tumour-associated antigen is preferably a tumour-associated antigen expressed by an EGFR expressing cancer. In a preferred embodiment, the tumour-associated antigen is preferably a ligand for a receptor tyrosine kinase, or a receptor tyrosine kinase. The receptor tyrosine kinase ligand is preferably a ligand of human c-Met (hepatocyte growth factor receptor [HGFR]), most preferably the c-Met ligand hepatocyte growth factor (HGF). The receptor tyrosine kinase is preferably human c-Met. Where the specific binding member of the invention further comprises one or more CDR-based antigen binding sites, as described herein, such as a CDR-based antigen binding site which binds to HGF, the specific binding member may elicit less skin toxicity, such as skin rashes and lesions, when administered to a (human) patient, than the specific binding member not comprising the, or any, CDR-based antigen binding site(s).

In a preferred embodiment, the specific binding member comprises a second antigen-binding site specific for HGF, wherein the binding site comprises the complementarity determining regions (CDRs) of antibody rilotumumab (RI) set forth in SEQ ID NOs 21-26, or the CDRs of antibody ficlatuzumab (FI) set forth in SEQ ID NOs 31-36. More preferably, the specific binding member comprises the VH and/or VL domains of antibody rilotumumab set forth in SEQ ID NOs 29 and 30, or the VH and/or VL domains of antibody ficlatuzumab set forth in SEQ ID NOs 39 and 40. Such a specific binding member may comprise the light chain sequence of SEQ ID NO: 28, or the light chain sequence of SEQ ID NO: 38.

The specific binding member of the present invention may comprise the light chain sequence of RI set forth in SEQ ID NO: 28 and/or the heavy chain sequence of the RI/FS1-60, RI/FS1-65, or RI-FS1-67 mAb$^2$ set forth in SEQ ID NOs 41, 43 and 45, respectively. Preferably, the specific binding member of the present invention comprises the light chain sequence of RI set forth in SEQ ID NO: 28 and the heavy chain sequence of the RI/FS1-60, RI/FS1-65, or RI-FS1-67 mAb$^2$ set forth in SEQ ID NOs 41, 43 and 45, respectively.

The specific binding member of the present invention may comprise the light chain sequence of FI set forth in SEQ ID NO: 38 and/or the heavy chain sequence of the FI/FS1-60, FI/FS1-65, or FI-FS1-67 mAb$^2$ set forth in SEQ ID NOs 42, 44 and 46, respectively. Preferably, the specific binding member of the present invention comprises the light chain sequence of FI set forth in SEQ ID NO: 38 and the heavy chain sequence of the FI/FS1-60, FI/FS1-65, or FI/FS1-67 mAb$^2$ set forth in SEQ ID NOs 42, 44 and 46, respectively.

Alternatively, where the specific binding member comprises a second antigen-binding site specific for HGF, the binding site may comprise the complementarity determining regions (CDRs) of antibody HuL2G7 described in U.S. Pat. No. 7,632,926. The CDRs of this HuL2G7 are set forth in SEQ ID NOs 62-67.

The specific binding member may further be conjugated to an immune system modulator, cytotoxic molecule, radioisotope, or detectable label. The immune system modulator may be cytotoxic molecule is a cytokine.

The present invention also provides a nucleic acid encoding a specific binding member or antibody molecule of the invention, as well as a vector comprising such a nucleic acid.

A recombinant host cell comprising a nucleic acid or the vector of the invention is also provided. Such a recombinant host cell may be used to produce a specific binding member of the invention. Thus, also provided is a method of producing a specific binding member or antibody molecule of the invention, the method comprising culturing the recombinant host cell under conditions for production of the specific binding member or antibody molecule.

The method may further comprise a step of isolating and/or purifying the specific binding member or antibody molecule.

The specific binding members and antibodies of the present invention are expected to find application in therapeutic applications, in particular therapeutic applications in humans, such as cancer treatment. Thus, also provided is a pharmaceutical composition comprising a specific binding member or antibody molecule according to the invention and a pharmaceutically acceptable excipient.

The present invention also provides a specific binding member or antibody molecule of the invention, for use in a method of treating cancer in a patient. Also provided is a method of treating cancer in a patient, wherein the method comprises administering to the patient a therapeutically effective amount of a specific binding member or antibody molecule according to the invention. Further provided is the use of a specific binding member or antibody molecule according to the invention for use in the manufacture of a medicament for the treatment of cancer in a patient.

BRIEF DESCRIPTION OF THE FIGURES

FIG. 9A shows a concentration dependent reduction in cell proliferation in the presence of FI/FS1-60 and RI/FS1-60 after 4 days, but not with ficlatuzumab (FI), rilotumumab (RI) or FS1-60 monotherapy, or treatment with a combination of FI+FS1-60 or RI+FS1-60. Concentration of treatment is plotted against percentage viable cell count (normalised against PBS control). FIG. 9B shows a repeat of the same assay with FI/FS1-65 and again, the $mAb^2$ showed a concentration dependent reduction in cell proliferation not observed with the monotherapies or a combination of FI+FS1-65. FIG. 9C shows that FI/FS1-65, RI/FS1-65 and the FI+FS1-65 combination also inhibited cell proliferation induced by HGF and EGF in a concentration dependent manner in NCI-H596 cells, whereas the ficlatuzumab monotherapy did not. Concentration of treatment is plotted against % growth due to EGF and HGF stimulation. Percentage of growth due to stimulation by EGF and HGF is indicated by a dotted line as is the percentage of growth where there was no ligand stimulation. FIG. 9D shows that FI/FS1-65 also reduced cell proliferation in a concentration dependent manner in NCI-H1975 cells stimulated with HGF whereas ficlatuzumab or FS1-65 monotherapies, or a combination of FI+FS1-65 did not. Concentration of treatment is plotted against percentage viable cell count (normalised against cells stimulated with HGF). FIG. 9E shows that FI/FS1-60, FI/FS1-65, RI/FS1-65 and the combination of FI+FS1-65 reduced cell proliferation in a concentration dependent manner in KP4 cells. FI also inhibited cell proliferation, but to a lesser extent. FS1-65, WT Fcab and IgG showed very little effect. Concentration of treatment is plotted against percentage viable cell count (normalised against PBS control). FIG. 9F shows that FI/FS1-65 (300 nM) reduced cell proliferation induced by HGF whereas erlotinib, FI or FI+erlotinib treatments did not in NCI-H1975 cells. Average cell number counted on each imaging site is plotted. FIG. 9G shows that the presence of HGF confers resistance to erlotinib in HCC827 cells. The effect of this resistance could be reduced by combining erlotinib with FI, but erlotinib+FI/FS1-65 combination could further reduce the dose required to inhibit cell proliferation. Concentration of erlotinib treatment is plotted against average cell number counted on each imaging site.

FIG. 14 shows the comparison of different treatments by Logrank test.

FIG. 15 shows the comparison of different treatments by Logrank test.

DETAILED DESCRIPTION

Figure 1:
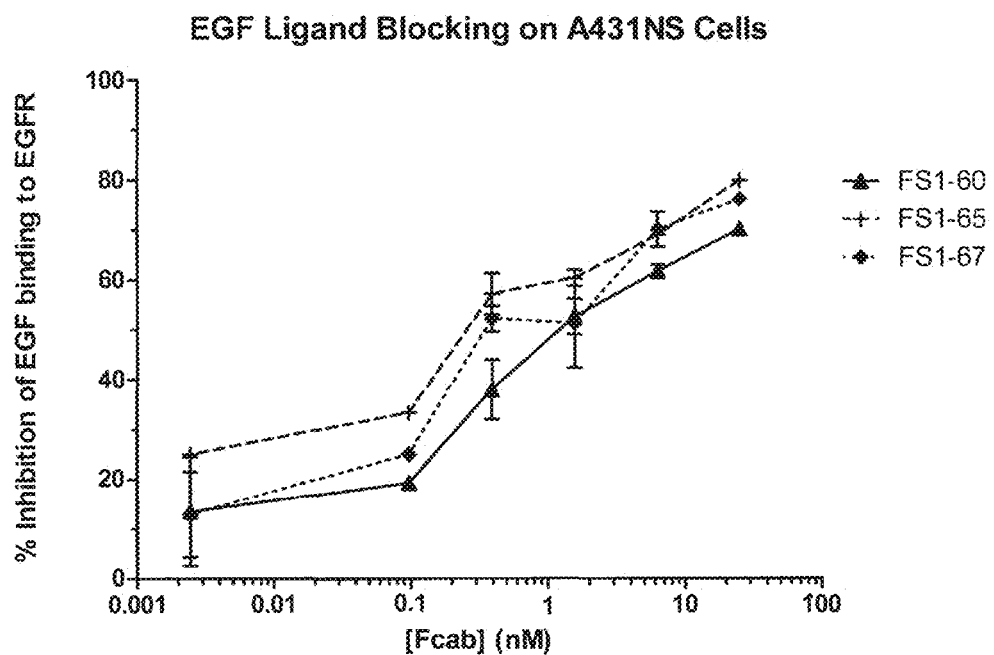
FIG. 1A shows that anti-EGFR Fcabs FS1-60, FS1-65 and FS1-67 block binding of the EGF ligand to EGFR on A431 NS (human epidermoid adenocarcinoma cells that overexpress EGFR). Percentage inhibition of EGF binding to EGFR is normalised to the PBS control, where PBS results in 0% inhibition.
FIG. 1B shows that FS1-60, FS1-65 and FS1-67 block binding of the TGFα ligand to recombinant EGFR/Fc. Percentage inhibition of TGFα binding to EGFR is normalised to the PBS control, where PBS results in 0% inhibition.
Figure 1:
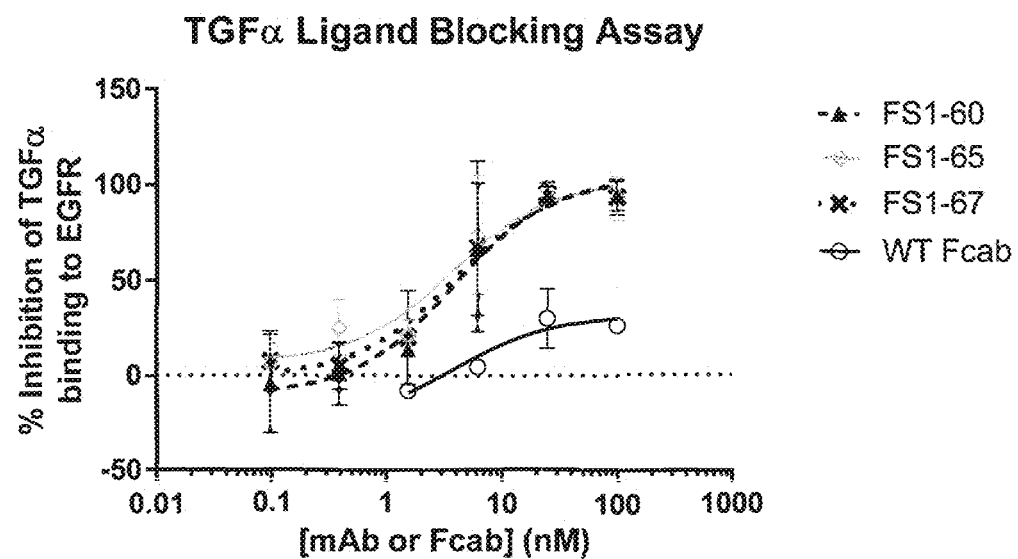

The present invention relates to specific binding members which bind to EGFR. The specific binding members of the present invention comprise an EGFR antigen-binding site located in a constant domain of the specific binding member. The term "EGFR" may refer to human EGFR and/or murine EGFR (such as mouse EGFR) unless the context requires otherwise. Preferably the term "EGFR" refers to human EGFR.

The term "specific binding member" describes an immunoglobulin, or fragment thereof, comprising a constant domain, preferably a CH3 domain, comprising an EGFR antigen-binding site. Preferably, the specific binding member comprises a CH2 and CH3 domain, wherein the CH2 or CH3 domain, preferably the CH3 domain, comprises an EGFR antigen-binding site. In a preferred embodiment, the specific binding member further comprises an immunoglobulin hinge region, or part thereof, at the N-terminus of the CH2 domain. Such a molecule is also referred to as an antigen-binding Fc fragment, or Fcab™, herein. The specific binding member may be partly or wholly synthetically produced.

The term "specific binding member", as used herein, thus includes fragments, provided said fragments comprise an EGFR antigen-binding site located in a constant domain, such as a CH1, CH2, or CH3 domain, preferably a CH3 domain, of the specific binding member. Unless the context requires otherwise, the term "specific binding member", as used herein, is thus equivalent to "specific binding member or fragment thereof".

In a preferred embodiment, the specific binding member is an antibody molecule. The term "antibody molecule" encompasses fragments of antibody molecules, provided such fragments comprise a constant domain, such as a CH1, CH2, or CH3 domain, preferably a CH3 domain, comprising an EGFR antigen-binding site. Unless the context requires otherwise, the term "antibody molecule", as used herein, is thus equivalent to "antibody molecule or fragment thereof". The antibody molecule may be human or humanised. The antibody molecule is preferably a monoclonal antibody molecule. Examples of antibody molecules are the immunoglobulin isotypes, such as immunoglobulin G, and their isotypic subclasses, such as IgG1, IgG2, IgG3 and IgG4, as well as fragments thereof.

It is possible to take monoclonal and other antibodies and use techniques of recombinant DNA technology to produce other antibodies or chimeric molecules which retain the specificity of the original antibody. Such techniques may involve introducing the CDRs, or variable regions, into a different immunoglobulin. Introduction of the CDRs of one immunoglobulin into another immunoglobulin is described for example in EP-A-184187, GB 2188638A or EP-A-239400. Similar techniques can be employed to introduce the relevant constant domain sequences, or structural loop sequences, providing the EGFR antigen-binding site into a different specific binding member. Alternatively, a hybridoma or other cell producing a specific binding member may be subject to genetic mutation or other changes, which may or may not alter the binding specificity of specific binding member produced.

As antibodies can be modified in a number of ways, the term "specific binding member" should be construed as covering antibody fragments, derivatives, functional equivalents and homologues of antibodies, whether natural or wholly or partially synthetic. An example of an antibody fragment comprising a CH3 domain is an Fc domain of an antibody. An example of an antibody fragment comprising both CDRs and a CH3 domain is a minibody, which comprises an scFv joined to a CH3 domain (Hu et al. (1996), Cancer Res., 56(13):3055-61).

The specific binding member of the present invention binds to EGFR. Binding in this context may refer to specific binding. The term "specific" may refer to the situation in which the specific binding member will not show any significant binding to molecules other than its specific binding partner(s), here EGFR. For example, the specific binding member may not bind to HER2, HER3, and/or HER4. The term "specific" is also applicable where the specific binding member is specific for particular epitopes, such as epitopes on EGFR, that are carried by a number of antigens in which case the specific binding member will be able to bind to the various antigens carrying the epitope.

A specific binding member of the invention preferably comprises an EGFR antigen-binding site. The EGFR antigen-binding site is located in a constant domain of the specific binding member, such as a CH1, CH2, CH3 or CH4 domain. Preferably, the EGFR antigen-binding site is located in the CH3 domain of the specific binding member. The EGFR binding site may comprise the amino acid sequences LDEGGP (SEQ ID NO: 1) and SHWRWYS (SEQ ID NO: 3). Alternatively, the EGFR binding site may comprise the amino acid sequences LDEGGP (SEQ ID NO: 1) and SYWRWVK (SEQ ID NO: 8). As a further alternative, the EGFR binding site may comprise the amino acid sequences TDDGP (SEQ ID NO: 13) and SYWRWYK (SEQ ID NO: 14). Preferably, the EGFR binding site comprises the amino acid sequences (i) LDEGGP (SEQ ID NO: 1) and SHWRWYS (SEQ ID NO: 3); or (ii) LDEGGP (SEQ ID NO: 1) and SYWRWVK (SEQ ID NO: 8).

The amino acid sequences set forth in SEQ ID NOs 1, 3, 8, 13 and 14 are preferably located in structural loops of the constant domain of the specific binding member. The introduction of sequences into the structural loop regions of antibody constant domains to create new antigen-binding sites is described, for example, in WO2006/072620 and WO2009/132876.

The structural loops of constant domains include the AB, CD and EF loops. In the CH3 domain, the AB, CD, and EF loops are located at residues 11-18, 43-78 and 92-101 of the CH3 domain, where the amino acid residue numbering is according to the ImMunoGeneTics (IMGT) numbering scheme. The amino acid sequences set forth in SEQ ID NOs 1 and 13 are preferably located in the AB loop of the constant domain. The amino acid sequences set forth in SEQ ID NOs 3, 8 and 14 are preferably located in the EF loop of the constant domain. More preferably, the amino acid sequence set forth in SEQ ID NO: 1 is located at residues 13.A to 18 of the CH3 domain, the amino acid sequence set forth in SEQ ID NO: 13 is located at residues 14 to 18 of the CH3 domain, and/or the amino acid sequences set forth in SEQ ID NOs 3, 8 and 14 are located at residues 92 to 98 of the CH3 domain, wherein the amino acid residue numbering is according to the IMGT numbering scheme.

In addition, the specific binding member preferably comprises the amino acid sequence set forth in SEQ ID NO: 2, in a structural loop of a constant domain of the specific binding member. The structural loop is preferably the CD loop and the constant domain is preferably the CH3 domain. The amino acid sequence set forth in SEQ ID NO: 2 is preferably located at residues 44 to 45.1 of the CH3 domain, wherein the amino acid residue numbering is according to the IMGT numbering scheme.

A specific binding member of the invention may further comprise an arginine residue (R) at position 88 of the CH3 domain, wherein the amino acid residue numbering is according to the IMGT numbering scheme. In particular, a specific binding member which comprises SEQ ID NO: 3 in the EF structural loop preferably further comprises an arginine residue (R) at position 88 of the CH3 domain.

The specific binding member of the present invention preferably comprises a CH3 domain from human IgG1, IgG2, IgG3, or IgG4, more preferably a human IgG1 CH3 domain, with one or more of the structural loop sequences set out above to provide an EGFR antigen-binding site.

In a preferred embodiment, the specific binding member of the invention comprises a CH3 domain which comprises, has, or consists of the sequence set forth in SEQ ID NO: 4, 9 or 15, preferably a CH3 domain which comprises, has, or consists of the sequence set forth in SEQ ID NO: 4 or 9.

The specific binding member of the invention may comprise a CH3 domain which comprises, has, or consists of the sequence set forth in SEQ ID NO: 4, 9 or 15, wherein the CH3 domain sequence further comprises a lysine residue (K) at the immediate C-terminus of the sequence shown in SEQ ID NO: 4, 9 or 15. Thus, for example, the specific binding member of the invention may comprise a CH3 domain which comprises, has, or consists of the sequence set forth in SEQ ID NO: 4 with a lysine residue at the C-terminus of the sequence shown in SEQ ID NO: 4. The sequence of such a CH3 domain would then be as follows:

(SEQ ID NO: 68)
GQPREPQVYTLPPSRDELDEGGPVSLTCLVKGFYPSDIAVEWESTYGP

ENNYKTTPPVLDSDGSFFLYSRLTVSHWRWYSGNVFSCSVMHEALHNH

YTQKSLSLSPGK

In addition, the specific binding member of the invention may comprise a CH2 domain of an immunoglobulin G molecule, such as a CH2 domain of an IgG1, IgG2, IgG3, or IgG4 molecule. Preferably the specific binding member of the invention comprises a CH2 domain of an IgG1 molecule. The CH2 domain may have the sequence set forth in SEQ ID NO: 19.

The CH2 domain of the specific binding member may comprise a mutation to reduce or abrogate binding of the CH2 domain to one or more Fc γ receptors, such as FcγRI, FcγRIIa, FcγRIIb, FcγRIII and/or to complement. CH2 domains of human IgG domains normally bind to Fc γ receptors and complement and the inventors postulate that reduced binding to Fc γ receptors will reduce the antibody-dependent cell-mediated cytotoxicity (ADCC) and reduced binding to complement will reduce the complement-dependent cytotoxicity (CDC) activity of the specific binding member. Mutations for reduce or abrogate binding of the CH2 domain to one or more Fc γ receptors and complement are known and include the "LALA mutation" described in Bruhns, et al. (2009) and Xu et al. (2000). Thus, the specific binding member may comprise a CH2 domain, wherein the CH2 domain comprises alanine residues at positions 4 and 5 of the CH2 domain, wherein the numbering is according to the IMGT numbering scheme.

In a preferred embodiment, the specific binding member of the present invention comprises the sequence set forth in SEQ ID NO: 6, 11, or 17, more preferably the sequence set forth in SEQ ID NO: 6, or 11.

Preferably, the specific binding member comprises an immunoglobulin hinge region, or part thereof, at the N-terminus of the CH2 domain. The immunoglobulin hinge region allows the two CH2-CH3 domain sequences to associate and form a dimer. Preferably, the hinge region, or part thereof, is a human IgG1, IgG2, IgG3 or IgG4 hinge region, or part thereof. More preferably, the hinge region, or part thereof, is an IgG1 hinge region, or part thereof. The sequence of the human IgG1 hinge region is shown in SEQ ID NO: 48. A suitable truncated hinge region which may form part of specific binding member is shown in SEQ ID NO: 49. This hinge region was present in the Fcab molecules tested in the Examples, whereas a full length IgG1 hinge region was present in mAb$^2$ molecules. Thus, the specific binding member preferably comprises an immunoglobulin hinge region, or part thereof, at the N-terminus of the CH2 domain, wherein the hinge region has the sequence set forth in SEQ ID NO: 48 or SEQ ID NO: 49, or wherein the hinge region has an amino acid sequence which has at least 70%, at least 75%, at least 80%, at least 85%, at least 90%, at least 95%, at least 96%, at least 97%, at least 98%, or at least 99% sequence identity to the sequence set forth in SEQ ID NO: 48 or 49. Alternatively, the specific binding member may comprises an immunoglobulin hinge region, or part thereof, at the N-terminus of the CH2 domain, wherein the hinge region comprises the sequence set forth in SEQ ID NO: 48, or a fragment thereof, wherein said fragment comprises at least five, at least six, at least seven, at least eight, at least nine, at least ten, at least eleven, at least twelve, at least thirteen, or at least fourteen of the amino acid residues of SEQ ID NO: 48.

A specific binding member according to the present invention may comprise a second antigen-binding site, preferably a CDR-based antigen-binding site. The term "CDR-based antigen-binding site" refers to the antigen-binding site of a specific binding member variable region which is composed of six CDR residues.

The second antigen-binding site preferably binds to, or is specific for, a tumour-associated antigen. Preferably, the tumour-associated antigen is a receptor tyrosine kinase ligand or receptor tyrosine kinase. In a preferred embodiment, the receptor tyrosine kinase ligand is HGF, and the receptor tyrosine kinase is c-Met. Most preferably, the second antigen-binding site binds to HGF. A specific binding member according to the present invention may thus inhibit the HGF/c-Met signalling pathway. Methods for determining inhibition of the HGF/c-Met signalling pathway are known in the art. For example, a suitable method is described in Spiess, et al. (2013).

The antibody molecules against a given antigen, such as a tumour antigen, and determination of the CDR sequences of such an antibody molecule, is well within the capabilities of the skilled person and many suitable techniques are known in the art. Furthermore, antibodies, including the CDR sequences, against various receptor tyrosine kinase ligands and receptor tyrosine kinases are known in the art. Thus, the skilled person would have no difficulty in preparing a specific binding member comprising in addition to an EGFR antigen-binding site as described herein a CDR-based antigen-binding site for a second antigen, such as a receptor tyrosine kinase ligand or receptor tyrosine kinase.

Preferably, the specific binding member of the invention comprises the HCDR3 of antibody rilotumumab or ficlatuzumab. The HCDR3 is known to play a role in determining the specificity of an antibody molecule (Segal et al., (1974), PNAS, 71:4298-4302; Amit et al., (1986), Science, 233:747-753; Chothia et al., (1987), J. Mol. Biol., 196:901-917; Chothia et al., (1989), Nature, 342:877-883; Caton et al., (1990), J. Immunol., 144:1965-1968; Sharon et al., (1990a), PNAS, 87:4814-4817; Sharon et al., (1990b), J. Immunol., 144:4863-4869; Kabat et al., (1991b), J. Immunol., 147:1709-1719).

The specific binding member may further comprise the HCDR1, HCDR2, LCDR1, LCDR2 and/or LCDR3 of antibody rilotumumab or ficlatuzumab. The skilled person would have no difficulty in determining the sequences of the CDRs from the VH and VL domain sequences of antibody rilotumumab or ficlatuzumab shown in SEQ ID NOs 29 and 30, and 39 and 40, respectively. The CDR sequences may, for example, be determined according to Kabat (Kabat, E. A. et al., (1991)) or the IMGT numbering scheme.

The sequences of the HCDR1, HCDR2, HCDR3, LCDR1, LCDR2 and LCDR3 of antibody rilotumumab, according to the Kabat numbering scheme, are set out in SEQ ID NOs 21, 22, 23, 24, 25, and 26, respectively.

The sequences of the HCDR1, HCDR2, HCDR3, LCDR1, LCDR2 and LCDR3 of antibody ficlatuzumab, according to the Kabat numbering scheme, are set out in SEQ ID NOs 31, 32, 33, 34, 35, and 36, respectively.

The antibody may also comprise the VH and/or VL domain of antibody rilotumumab or ficlatuzumab. The VH and VL domain sequences of antibody rilotumumab or ficlatuzumab are shown in SEQ ID NOs 29 and 30, and 39 and 40, respectively.

In a preferred embodiment, the specific binding member of the invention comprises (i) a CDR-based antigen binding site for HGF comprising the HCDR1, HCDR2, HCDR3, LCDR1, LCDR2 and LCDR3 sequences of antibody rilotumumab or ficlatuzumab, and (ii) an EGFR antigen binding site located in a CH3 domain of the specific binding member, wherein the EGFR binding site comprises the amino acid sequences set forth in SEQ ID NOs 1, 2 and 3, SEQ ID NOs 1, 2 and 8, or SEQ ID NOs 13, 2 and 14.

More preferably, the specific binding member of the invention comprises (i) a CDR-based antigen binding site for HGF comprising the HCDR1, HCDR2, HCDR3, LCDR1, LCDR2 and LCDR3 sequences of antibody rilotumumab or ficlatuzumab, and (ii) an EGFR antigen binding site located in a CH3 domain of the specific binding member, wherein the EGFR binding site comprises the amino acid sequences set forth in SEQ ID NOs 1, 2 and 3, or SEQ ID NOs 1, 2 and 8.

In a preferred embodiment, the specific binding member of the invention comprises a VH domain and a VL domain which comprises, has, or consists of the sequence set forth in SEQ ID NOs 29 and 30, or SEQ ID NOs 39 and 40, respectively, and a CH3 domain which comprises, has, or consists of the sequence set forth in SEQ ID NO: 4, 9, or 15, preferably a CH3 which comprises, has, or consists of the sequence set forth in SEQ ID NO: 4 or 9.

In a further preferred embodiment, the specific binding member comprises a heavy chain which comprises, has, or consists of the sequence set forth in SEQ ID NO: 41, 43, or 45 and a light chain which comprises, has, or consists of the sequence set forth in SEQ ID NO: 28. More preferably, the specific binding member comprises a heavy chain which comprises, has, or consists of the sequence set forth in SEQ ID NO: 41 or 43 and a light chain which comprises, has, or consists of the sequence set forth in SEQ ID NO: 28.

In an alternative preferred embodiment, the specific binding member comprises a heavy chain which comprises, has, or consists of the sequence set forth in SEQ ID NO: 42, 44, or 46 and a light chain which comprises, has, or consists of the sequence set forth in SEQ ID NO: 38. More preferably, the specific binding member comprises a heavy chain which comprises, has, or consists of the sequence set forth in SEQ ID NO: 42 or 44 and a light chain which comprises, has, or consists of the sequence set forth in SEQ ID NO: 38.

The specific binding members of the present invention may also comprise variants of the structural loop, CH3 domain, CH2 domain, CH2 and CH3 domain, CDR, VH domain, VL domain, light chain or heavy chain sequences disclosed herein. Suitable variants can be obtained by means of methods of sequence alteration, or mutation, and screening. In a preferred embodiment, a specific binding member comprising one or more variant sequences retains one or more of the functional characteristics of the parent specific binding member, such as binding specificity and/or binding affinity for EGFR, and/or a second antigen such as HGF. For example, a specific binding member comprising one or more variant sequences preferably binds to EGFR, and/or a second antigen such as HGF, with the same affinity, or a higher affinity, than the (parent) specific binding member. The parent specific binding member is a specific binding member which does not comprise the amino acid substitution(s), deletion(s), and/or insertion(s) which have been incorporated into the variant specific binding member.

For example, a specific binding member of the invention may comprise a structural loop, CH3 domain, CH2 domain, CH2 and CH3 domain, CDR, VH domain, VL domain, light chain or heavy chain sequence which has at least 70%, at least 75%, at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to a structural loop, CH3 domain, CH2 domain, CH2 and CH3 domain, CDR, VH domain, VL domain, light chain or heavy chain sequence disclosed herein.

In a preferred embodiment, the specific binding member of the invention comprises a CH3 domain sequence which has at least 70%, at least 75%, at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the CH3 domain sequence set forth in SEQ ID NO: 4, 9, or 15, more preferably SEQ ID NO: 4 or 9.

In a further preferred embodiment, the specific binding member of the invention comprises a CH3 and CH2 domain sequence, which has at least 70%, at least 75%, at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the CH2 and CH3 domain sequence set forth in SEQ ID NO: 6, 11, or 17, more preferably SEQ ID NO: 6 or 11.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), or the TBLASTN program, of Altschul et al. (1990) supra, generally employing default parameters. In particular, the psi-Blast algorithm (Nucl. Acids Res. (1997) 25 3389-3402) may be used.

A specific binding member of the invention may also comprise a structural loop, CH3 domain, CH2 domain, CH2 and CH3 domain, CDR, VH domain, VL domain, light chain or heavy chain sequence which has one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with a structural loop, CH3 domain, CH2 domain, CH2 and CH3 domain, CDR, VH domain, VL domain, light chain or heavy chain sequence disclosed herein. In particular, alterations may be made in one or more framework regions of the specific binding member.

In a preferred embodiment, the specific binding member of the invention may comprise a CH3 domain sequence with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH3 domain sequence set forth in SEQ ID NO: 4, 9, or 15, more preferably SEQ ID NO: 4 or 9.

In a further preferred embodiment, the specific binding member of the invention comprises a CH3 and CH2 domain sequence, with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH2 and CH3 domain sequence set forth in SEQ ID NO: 6, 11, or 17, more preferably SEQ ID NO: 6 or 11.

Also contemplated is a specific binding member which competes with a specific binding member of the invention for binding to EGFR, or which binds to the same epitope on EGFR as a specific binding member of the invention, wherein the specific binding member preferably comprises an EGFR antigen-binding site located in a CH3 domain of the specific binding member. Methods for determining competition for an antigen by two specific binding members are known in the art. For example, competition of binding to an antigen by two specific binding members can be determined using surface plasmon resonance, e.g. BIAcore. Methods for mapping the epitope bound by an antibody are similarly known in the art, and can be employed to map the epitope or epitopes bound by a specific binding member of the invention.

The specific binding member of the invention preferably binds to EGFR with an affinity ($K_D$) of 4.5 nM or an affinity which is greater. For example, the specific binding member of the invention may bind to EGFR with an affinity ($K_D$) of 4.5 nM, 4 nM, 3.6 nM, 3.5 nM, 2.6 nM, 2.5 nM, 2 nM, 1.8 nM, 1.6 nM, 1.5 nM, 1.3 nM, 1 nM, 0.7 nM, or an affinity which is greater.

The binding affinity of a specific binding member to a cognate antigen, such as EGFR can be determined by surface plasmon resonance (SPR), for example. The binding affinity of a specific binding member to a cognate antigen, such as EGFR, expressed on a cell surface can be determined by flow cytometry.

The specific binding member of the present invention is preferably capable of binding to EGFR expressed on the surface of a cell. The cell is preferably a cancer cell.

Where the specific binding member comprises a second antigen-binding site, such as CDR-based antigen-binding site, specific for a second antigen, the specific binding member is preferably capable of simultaneously binding to EGFR and the second antigen. Preferably, the specific binding member is capable of simultaneously binding to EGFR and the second antigen.

The specific binding member of the invention may bind to human EGFR, and/or murine EGFR (such as mouse EGFR). Preferably, the specific binding member of the invention binds to human EGFR.

The specific binding member of the present invention may be conjugated to a therapeutic agent or detectable label. In this case, the specific binding member may be referred to as a conjugate. For example, the specific binding member may be conjugated to an immune system modulator, cytotoxic molecule, radioisotope, or detectable label. The immune system modulator or cytotoxic molecule may be a cytokine. The detectable label may be a radioisotope, e.g. a non-therapeutic radioisotope.

The specific binding member may be conjugated to the therapeutic agent or detectable label, by means of a peptide bond or linker, i.e. within a fusion polypeptide comprising said therapeutic agent or detectable label and the specific binding member or a polypeptide chain component thereof. Other means for conjugation include chemical conjugation, especially cross-linking using a bifunctional reagent (e.g. employing DOUBLE-REAGENTS™ Cross-linking Reagents Selection Guide, Pierce).

The specific binding member and the therapeutic agent or detectable label may thus be connected to each other directly, for example through any suitable chemical bond or through a linker, for example a peptide linker.

The peptide linker may be a short (2-20, preferably 2-15, residue stretch of amino acids). Suitable examples of peptide linker sequences are known in the art. One or more different linkers may be used. The linker may be about 5 amino acids in length.

The chemical bond may be, for example, a covalent or ionic bond. Examples of covalent bonds include peptide bonds (amide bonds) and disulphide bonds. For example the specific binding member and therapeutic or diagnostic agent may be covalently linked, for example by peptide bonds (amide bonds). Thus, the specific binding member and therapeutic or diagnostic agent may be produced (secreted) as a single chain polypeptide.

The invention also provides isolated nucleic acids encoding the specific binding members of the invention. The skilled person would have no difficulty in preparing such nucleic acids using methods well-known in the art. An isolated nucleic acid may be used to express the specific binding member of the invention, for example, by expression in a bacterial, yeast, insect or mammalian host cell. A preferred host cell is a mammalian cell such as a CHO, HEK or NS0 cell. The nucleic acid will generally be provided in the form of a recombinant vector for expression.

The isolated nucleic acid may, for example, comprise the sequence set forth in SEQ ID NO: 5, 7, 10, 12, 16, or 18.

In vitro host cells comprising such nucleic acids and vectors are part of the invention, as is their use for expressing the specific binding members of the invention, which may subsequently be purified from cell culture and optionally formulated into a pharmaceutical composition. The present invention thus further provides a method of producing the specific binding member of the invention, comprising culturing the recombinant host cell of the invention under conditions for production of the specific binding member. Methods for culturing suitable host cells as mentioned above are well-known in the art. The method may further comprise isolating and/or purifying the specific binding member. The method may also comprise formulating the specific binding member into a pharmaceutical composition, optionally with a pharmaceutically acceptable excipient or other substance as described below.

As mentioned above, many cancers have been shown to express EGFR on their cell surface. The present inventors have shown that specific binding members comprising an EGFR antigen-binding site, i.e. an antigen-binding site which binds EGFR, in the CH3 domain of the specific binding member have anti-tumour properties, including the ability to block binding of epidermal growth factor (EFG) to EGFR, which is known to stimulate cell growth, proliferation and differentiation. Incorporation of the EGFR antigen-binding sites into antibodies with known anti-tumour effects resulted in specific binding members with more potent anti-tumour properties, including more potent inhibition of tumour cell proliferation, than that of the parental antibodies. In addition, specific binding members comprising an EGFR antigen-binding site in the CH3 domain were shown to be internalized by the tumour cells. Internalization of the specific binding members by the tumour cells may provide a number advantages. For example, it is thought that EGFR was internalized along with the specific binding members. Without wishing to be bound by theory, internalisation of EGFR is thought to lead to degradation of EGFR, thereby decreasing activation of the receptor, as its ligand(s) will no longer be able to bind to the receptor. In addition, any anti-tumour molecules conjugated to the specific binding member would be internalized along with the specific binding member, which is expected to reduce non-specific toxicity of the anti-tumour molecules, for example. Furthermore, any soluble ligands bound to a second, CDR-based, antigen-binding site of the specific binding member, such as HGF, are also expected to be internalized along with the specific binding member and consequently sequestered from the environment. Rapid internalisation of the specific binding member may also result in a more rapid initial response to treatment, thereby making it possible to determine whether patients respond to the treatment at an early stage.

Thus, the present invention provides a specific binding member of the invention for use in a method of treating cancer in a patient, wherein cells of said cancer express EGFR. Also provided is the use of a specific binding member of the invention in the manufacture of a medicament for treating cancer in a patient, wherein cells of said cancer express EGFR, as well as a method of treating cancer in a patient, wherein cells of said cancer express EGFR, and wherein the method comprises administering to the patient a therapeutically effective amount of a specific binding member of the invention.

Where the specific binding member comprises a second antigen-binding site which binds to HGF or c-Met, the cells of the cancer to be treated with the specific binding member preferably further secrete HGF and/or express c-Met.

The patient is preferably a human patient.

Cells of the cancer to be treated using the specific binding member of the invention express EGFR, e.g. on their cell surface. In one embodiment, cells of the cancer to be treated may have been determined to express EGFR, e.g. on their cell surface. Methods for determining the expression of an antigen on a cell surface are known in the art and include, for example, flow cytometry.

A cancer to be treated using a specific binding member of the invention may be selected from the group consisting of: lung cancer (for example, non-small cell lung cancer), glioblastoma multiforme, pancreatic cancer, skin cancer (for example cutaneous squamous cell carcinoma), head and neck cancer (for example squamous cell carcinoma of the head and neck), breast cancer, colorectal cancer, ovarian cancer, gastric cancer, and endometrial cancer. Gastric cancer, as referred to herein, includes oesophageal cancer, such as gastroesophageal cancer.

All of the cancers mentioned above have been shown to express EGFR. An EGFR expressing cancer may be referred to as EGFR positive (EGFR+) or as overexpressing EGFR. Thus, a cancer, as referred to herein, may be EGFR positive. In addition, or alternatively, a cancer as referred to herein may overexpress EGFR. Whether a cancer is EGFR positive or overexpresses EGFR may be determined using immunohistochemistry (IHC), for example.

Preferably, the cancer is lung cancer, glioblastoma multiforme, pancreatic cancer, skin cancer, head and neck cancer, colorectal cancer, gastric cancer, or breast cancer.

More preferably, the cancer is lung cancer, glioblastoma multiforme, pancreatic cancer, head and neck cancer, or gastric cancer.

Most preferably, the cancer is lung cancer, glioblastoma multiforme, or pancreatic cancer.

Where the specific binding member is a specific binding member comprising a second antigen-binding site specific for HGF, said binding site comprising the complementarity determining regions (CDRs) of antibody rilotumumab set forth in SEQ ID NOs 21-26, the cancer is preferably gastric cancer, wherein cells of said cancer express EGFR. Rilotumumab has been tested for the treatment of gastric cancer in the clinic.

Where the specific binding member is a specific binding member comprising a second antigen-binding site is specific for HGF, said binding site comprising the complementarity determining regions (CDRs) of antibody ficlatuzumab set forth in SEQ ID NOs 31-36, the cancer is preferably lung cancer, most preferably non-small cell lung cancer, wherein cells of said cancer express EGFR. Ficlatuzumab has been shown to be suitable for the treatment of lung cancer, in particular non-small cell lung cancer, in the clinic.

Where the application refers to a particular type of cancer, such as lung cancer, this refers to a malignant transformation of the relevant tissue, in this case a lung tissue. A cancer which originates from malignant transformation of a different tissue, e.g. breast tissue, may result in metastatic lesions in another location in the body, such as the lung, but is not thereby a lung cancer as referred to herein but a breast cancer.

The cancer may be a primary or secondary cancer. Thus, the specific binding member of the present invention may be for use in a method of treating cancer in a patient, wherein the cancer is a primary tumour and/or a tumour metastasis.

The specific binding members of the invention are designed to be used in methods of treatment of patients, preferably human patients. Specific binding members will usually be administered in the form of a pharmaceutical composition, which may comprise at least one component in addition to the specific binding member, such as a pharmaceutically acceptable excipient. For example, a pharmaceutical composition of the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be by injection, e.g. intravenous or subcutaneous. The specific binding member may be administered intravenously, or subcutaneously.

Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the specific binding member, or pharmaceutical composition comprising the specific binding member, is preferably in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be employed, as required. Many methods for the preparation of pharmaceutical formulations are known to those skilled in the art. See e.g. Robinson ed., Sustained and Controlled Release Drug Delivery Systems, Marcel Dekker, Inc., New York, 1978.

A composition comprising a specific binding members according to the present invention may be administered alone or in combination with other treatments, concurrently or sequentially or as a combined preparation with another therapeutic agent or agents, dependent upon the condition to be treated. For example, a specific binding member of the invention may be administered in combination with an existing therapeutic agent for the disease to be treated, e.g. a cancer as mentioned above. For example, a specific binding member of the present invention may be administered to the patient in combination with a second anti-cancer therapy, such as chemotherapy, radiotherapy, immunotherapy, or hormone therapy. In particular, a specific binding member of the present invention may be administered to the patient in combination with, or be for administration in combination with, an EGFR inhibitor, such as erlotinib or cetuximab, preferably erlotinib. Alternatively, a specific binding member of the present invention may be administered to the patient in combination with, or be for administration in combination with, an antibody molecule which binds to HGF, such as ficlatuzumab or rilotumumab.

A method of treating cancer in a patient may thus comprise administering to the patient a therapeutically effective amount of a specific binding member according to the present invention in combination with a chemotherapeutic agent, radionuclide, immunotherapeutic agent, or agent for hormone therapy. The chemotherapeutic agent, radionuclide, immunotherapeutic agent, or agent for hormone therapy is preferably a chemotherapeutic agent, radionuclide, immunotherapeutic agent, or agent for hormone therapy for the cancer in question, i.e. a chemotherapeutic agent, radionuclide, immunotherapeutic agent, or agent for hormone therapy which has been shown to be effective in the treatment of the cancer in question. The selection of a suitable chemotherapeutic agent, radionuclide, immunotherapeutic agent, or agent for hormone therapy which has been shown to be effective for the cancer in question is well within the capabilities of the skilled practitioner.

Administration may be in a "therapeutically effective amount", this being sufficient to show benefit to a patient. Such benefit may be at least amelioration of at least one symptom. Thus "treatment" of a specified disease refers to amelioration of at least one symptom. The actual amount administered, and rate and time-course of administration, will depend on the nature and severity of what is being treated, the particular patient being treated, the clinical condition of the individual patient, the cause of the disorder, the site of delivery of the composition, the type of specific binding member, the method of administration, the scheduling of administration and other factors known to medical practitioners. Prescription of treatment, e.g. decisions on dosage etc., is within the responsibility of general practitioners and other medical doctors, and may depend on the severity of the symptoms and/or progression of a disease being treated. Appropriate doses of specific binding members are well known in the art (Ledermann et al. (1991) Int. J. Cancer 47: 659-664; and Bagshawe et al. (1991) Antibody, Immunoconjugates and Radiopharmaceuticals 4: 915-922). Specific dosages indicated herein, or in the Physician's Desk Reference (2003) as appropriate for a specific binding member being administered, may be used. A therapeutically effective amount or suitable dose of a specific binding member can be determined by comparing its in vitro activity and in vivo activity in an animal model. Methods for extrapolation of effective dosages in mice and other test animals to humans are known. The precise dose will depend upon a number of factors, including whether the size and location of the area to be treated, and the precise nature of the specific binding member. Treatments may be repeated at daily, twice-weekly, weekly or monthly intervals, at the discretion of the physician. Treatment may be given before, and/or after surgery, and may be administered or applied directly at the anatomical site of surgical treatment.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXAMPLES

Example 1—Preparation of Anti-EGFR Antigen-Binding Fcs (Fcabs)

EGFR specific Fcabs were selected by Fluorescence Activated Cell Sorting (FACS) from a yeast display Fcab library and by magnetic bead capture from a phage display Fcab library as described below.

Naïve selection of anti-EGFR Fcabs from a yeast library using FACS The method used to select antigen specific Fcabs from yeast display Fcab libraries by FACS is described in WO 2009/132876. Libraries expressing Fcab clones on the yeast cell surface were incubated with 300 nM of biotinylated EGFR extracellular domain. The cells were then stained with streptavidin-allophycocyanin (APC) (BD Bioscience, 349024) for isolation of antigen-binding yeast cells by fluorescent signal using a high speed cell sorter (BD Bioscience, FACSAria™). This selection procedure was repeated several times to enrich for a sufficiently pure antigen-binding yeast cell population. Streptavidin-APC and anti-Biotin-APC (Miltenyi Biotec, 130-090-856) were used in alternating rounds for staining to avoid non-specific selection. Individual clones from enriched populations were screened for antigen binding and the most promising clones were cloned into a *Pichia* expression vector pPICZalphaA for expression of soluble proteins following the supplier's protocol (Invitrogen, K1740-01) and characterization.

Naïve Selection of Anti-EGFR Fcabs from a Phage Display Fcab Library

EGFR specific Fcabs from phage display Fcab libraries were selected through capturing on magnetic beads. A phage display library containing approximately $1 \times 10^{10}$ phage and 200 µl of streptavidin-coated magnetic beads (Invitrogen, Dynabeads©) were blocked separately in 1.5 ml tubes with 2% milk/PBST at room temperature (RT) with rotation for 1 hr. The blocked phage display libraries were incubated with 1-100 nM biotinylated EGFR in 2% milk/PBST at RT for 1 hr for binding selection. The blocked streptavidin-coated magnetic beads were captured by holding the 1.5 ml tube in a magnetic rack (DynaMag™, Invitrogen) while removing the supernatant, followed by resuspension in the biotinylated EGFR/phage mixture and incubated for 5 min. The bead/EGFR/phage compounds were captured by the magnet and eluted using 1 mg/ml trypsin for 10 min. The eluted phage were used to infect *E. coli* TG1 competent cells (Lucigen) and were incubated for 30 min at 37° C. The phage infected TG1 cells were plated on 2×YT agar and then grown for amplification in 100 ml 2×YT medium overnight at 37° C. After removal of the TG1 cells by centrifugation, the medium supernatant was mixed with PEG/NaCl at a ratio of 4:1 and incubated on ice for 1 hr to precipitate the enriched phage. The phage were pelleted by centrifugation at 4400 rpm for 30 min at 4° C. and resuspended in PBS. This enriched population of phage displayed EGFR specific Fcab clones was used for further enrichment by repeating the selection process several times. Individual clones were screened by ELISA and clones with strong binding to EGFR were cloned into *Pichia* and expressed as described above.

Affinity Maturation of Selected Fcabs

For affinity maturation, sequence diversity was introduced into the Fcabs selected from the yeast and phage display libraries by loop shuffling. The AB_CD loop region was amplified using primers 1 and 2, and the CD_EF loop region was amplified using primers 3 and 4 by PCR. The primer sequences are listed in Table 1 below.

TABLE 1

| Primer ID | Name | Sequence |
|---|---|---|
| 1 | 07 CH3 new | 5'CACAGTGCACAGCCTCGAGAACC ACAGGTGTACACCCTGCC |
| 2 | Shuff Rev3 | 5'GAGCTTGCTGTAGAGGAAGAAGG |
| 3 | 03 CH3 new | 5'GCTTGCGGCCGCTTTACCCGGAG ACAGGGAGAGG |
| 4 | Shuff For1 | 5'GCCTGGTCAAAGGCTTCTATCC |

(From top-bottom SEQ ID NOs: 69-72)

The AB_CD and CD_EF loop regions were mixed and assembled to generate new sequence combinations by pull-through PCR. The shuffled PCR products were ligated into the phage display vector FdMyc and transformed into TB1 *E. coli* cells by electroporation. This loop shuffled library was used for phage selection as described above to screen for improved binders. Decreasing antigen concentrations from 100 nM to 10 and 1 nM were used in subsequent selection and screening strategies to identify high affinity binders.

Individual affinity matured EGFR specific Fcabs with improved binding affinity were expressed in *Pichia* and HEK cells for characterisation. The Fcabs identified using this selection strategy included FS1-60 (SEQ ID NO: 6), FS1-65 (SEQ ID NO: 11) and FS1-67 (SEQ ID NO: 17). These Fcabs comprised the CH2 and CH3 domain sequences set forth in SEQ ID NOs 6, 11 and 17, respectively, and the truncated hinge region set forth in SEQ ID NO: 49 at the N-terminus of the CH2 domain.

Example 2—EGFR Specific Fcabs Bind Specifically to EGFR

An enzyme-linked immunosorbent assay (ELISA) was used to determine if the anti-EGFR Fcabs, FS1-60, FS1-65 and FS1-67 specifically bind to EGFR in the HER receptor family.

Antigens including EGFR (produced in house), HER2 His Tag (Sino Biological, 10004-H08H), HER3 His Tag (Sino Biological, 10201-H08H) and HER4 His Tag (Sino Biological, 10363-H08H) were biotinylated using the Lightning-Link™ Biotin kit (Innova Biosciences, 704-0030) following the supplier's protocol. The biotinylated antigens were coated in different wells on MaxiSorp™ plate (Nunc) at 1 μg/ml in PBS overnight at 4° C. and excess unbound antigens were washed off with PBS. The antigen-coated plate was blocked with 1% TWEEN® in PBS (PBST) for 1 hour at room temperature. After removing PBST, the anti-EGFR Fcabs (1 μM) and relevant positive and IgG negative antibody controls (1 μM) in 0.1% PBST were incubated for 1 hour to bind the coated antigens followed by washing. The bound Fcabs or antibodies were detected by Protein A-HRP (ThermoFisher 101023) or anti-mouse IgG-horseradish peroxidase (HRP) (Sigma A9044) for the HER4 positive control. Tetramethylbenzidine (TMB) (eBioscience 00-4201-56) was used as the substrate to interact with HRP enzyme for colorimetric detection. 1 M Sulphuric acid was added to stop the enzyme-substrate reaction. The plate was read at an absorbance of 450 nm subtracted by 630 nm as background.

Positive controls trastuzumab (Roche) and pertuzumab (Genentech) for HER2, antibody MM121 (Merrimack) for HER3 and an anti-HER4 antibody for HER4 (R&D Systems, MAB11311) bound to their corresponding antigens. The anti-EGFR Fcabs FS1-60, FS1-65 and FS1-67 showed binding to EGFR but not to HER2, HER3 or HER4, demonstrating their specificity for EGFR.

Example 3—EGFR Specific Fcabs Bind to a Different Epitope on EGFR than Cetuximab Surface Plasmon Resonance (SPR) was used to determine if the EGFR specific Fcabs FS1-60, FS1-65 and FS1-67 compete with the known anti-EGFR antibody, cetuximab (Merck), for binding to EGFR.

A BIAcore™ 3000 (GE healthcare) was used to determine if EGFR specific Fcabs FS1-60, FS1-65 and FS1-67 could bind to a human EGFR coated chip that was saturated with cetuximab (CX) and vice versa.

A streptavidin chip (SA chip) (GE Healthcare BR-1000-32) was coated with 200 RU of extracellular domain (ECD) of biotinylated human EGFR. Experiments were carried out using a flow rate of 20 μl/min in HBS-P buffer (GE Healthcare), and the EGFR surface was regenerated by flowing over 50 mM NaOH at 50 μl/min for 12 sec three times. The first EGFR binding compound (EGFR specific Fcabs or cetuximab) was injected at 20 μl/min for 4 min and then the second EGFR binding compound (cetuximab or EGFR specific Fcabs) was injected for 4 min (the second injection was performed in a mixture with the first compound in order to eliminate the dissociation of the first compound during the second injection) followed by dissociation in HBS-P buffer. In the case where the first and second injections were performed using the same compound (cetuximab followed by cetuximab), little or no additional response was observed at the second injection, showing that the EGFR binding surface was saturated.

TABLE 2

Biacore binding responses of Fcabs to immobilised EGFR in competition with cetuximab

| Injection 1 | Response (RU) | Injection 2 | Additional Response (RU) |
|---|---|---|---|
| Cetuximab (1 μM) | 38.6 | Cetuximab (1 μM) | −2.7 |
| Cetuximab (1 μM) | 39.0 | FS1-60 (1 μM) + Cetuximab (1 μM) | 22.2 |
| Cetuximab (1 μM) | 40.5 | FS1-65 (1 μM) + Cetuximab (1 μM) | 26.0 |
| Cetuximab (1 μM) | 40.4 | FS1-67 (1 μM) + Cetuximab (1 μM) | 27.4 |
| FS1-60 (1 μM) | 36.3 | Cetuximab (1 μM) + FS1-60 (1 μM) | 31.7 |
| FS1-65 (1 μM) | 50.5 | Cetuximab (1 μM) + FS1-65 (1 μM) | 35.4 |
| FS1-67 (1 μM) | 54.2 | Cetuximab (1 μM) + FS1-67 (1 μM) | 31.0 |

Table 2 shows that there was a small reduction in the binding response of EGFR specific Fcabs on an EGFR-coated chip saturated with cetuximab (22.2-27.4 RU) compared to that of EGFR specific Fcabs binding to a naked EGFR surface (36.3-54.2 RU), indicating that the EGFR specific Fcabs bind to epitopes on EGFR that are different but partially overlapping with the cetuximab epitope. The same effect was also observed when the injection series was reversed: the binding response of cetuximab on an Fcab-saturated surface (31.0-35.4 RU) reduced slightly compared to that of cetuximab binding to a naked EGFR surface (39.0-40.5 RU).

Example 4—Binding Affinities of EGFR Specific Fcabs to Human and Mouse EGFR

The binding affinities of EGFR specific Fcabs to human and mouse EGFR were determined using SPR. For affinity measurements, a BIAcore 3000 instrument (GE healthcare) was used and an SA chip was coated with 200 or 1000 RU of biotinylated human (in house) or mouse (Sino Biological) EGFR extracellular domain. Concentration ranges of Fcabs (1-1000 nM) were injected in HBS-P buffer (GE Healthcare) at 20 μl/min for 2.5 min to measure the on-rate. HBS-P buffer was then injected for 15 min to determine the dissociation rate. The EGFR surface was regenerated using 50 mM NaOH at 50 μl/min for 10 seconds two times. The binding affinity ($K_D$) was derived from 1:1 (Langmuir) fitting model using the BIAevaluation software version 3.2 RC1 (GE Healthcare). The results showed that the EGFR specific Fcabs bind to human and mouse EGFR with binding affinities between 0.7-6.0 nM (see Table 3).

TABLE 3

Binding affinity ($K_D$) of EGFR specific Fcabs to human and mouse EGFR

| Fcab | Human EGFR $K_D$ (nM) | Mouse EGFR $K_D$ (nM) |
|---|---|---|
| FS1-60 | 2.6 | 6.0 |
| FS1-65 | 0.7 | 0.8 |
| FS1-67 | 1.3 | 2.5 |

Example 5—Ligand Blocking Activity of Anti-EGFR Fcabs

Anti-EGFR Fcabs FS1-60, FS1-65 and FS1-67 were tested for the ability to block binding of the ligand EGF to EGFR-expressing human epidermoid adenocarcinoma cell line A431 NS (ATCC CRL-2592).

A431NS cells were dissociated with Cell Dissociation Buffer (GIBCO, 13151-014) for 20 min to avoid damage to the cell surface EGFR receptor. Cells were suspended in PBS with 2% Foetal Bovine Serum (FBS) (Life Technologies, 10270) (flow buffer). $2 \times 10^5$ cells were plated in 100 μl in a 96 well plate and then incubated for 15 min with Fcabs at various concentrations (0.002-25 nM) using PBS as negative control. These cells were then incubated with biotinylated EGF (Invitrogen, EB477) at 40 ng/ml for 1 hour at 4° C. to compete with Fcabs for binding to EGFR. Unbound Fcabs or biotinylated EGF were washed off from the cells with flow buffer. Biotinylated EGF that bound to the cells was detected by Streptavidin-PE after a 45 min incubation on ice (Invitrogen, SA10041) and the signal was read on a flow cytometer (BD Accuri™ C6). FIG. 1A shows the percentage inhibition of EGF binding to EGFR normalised to the PBS control, where PBS results in 0% inhibition. The results demonstrate that anti-EGFR Fcabs blocked EGF binding to EGFR with an $IC_{50}$ in the range of 0.46 to 0.61 nM (see Table 4). These results therefore demonstrate that FS1-60, FS1-65 and FS1-67 block binding of EGF to cell surface EGFR.

Anti-EGFR Fcabs FS1-60, FS1-65 and FS1-67 were also tested for the ability to block binding of the ligand TGFα to recombinant EGFR/Fc (Sino Biological) by ELISA.

TGFα was immobilised on MaxiSorp plate (Nunc) in bicarbonate buffer pH 9.2 at 4 or 37° C. overnight and excess TGFα was washed off with PBS. The TGFα coated plate was blocked with 1% BSA in 1% TWEEN® in PBS (PBST) for 2 hours at room temperature before incubation with the Fcab (0.1-100 nM) and EGFR/Fc (2 μg/ml) mixture (pre-mixed for 1 hour) for 1 hour at 37° C. EGFR/Fc that bound to the Fcabs was washed off whereas EGFR/Fc that bound to TGFα was detected with anti-human IgG-HRP (Sigma). TMB (eBioscience) was used as the substrate to interact with HRP enzyme for colorimetric detection and the reaction was stopped by 1 M sulphuric acid. FIG. 1B shows the percentage blocking of TGFα binding to EGFR/Fc by anti-EGFR Fcabs normalised to TGFα binding to EGFR/Fc without Fcabs as 0% blocking. The results show that anti-EGFR Fcabs blocked TGFα binding to EGFR/Fc with an $IC_{50}$ in the range of 3.7-4.0 nM (Table 4).

TABLE 4

| Fcab | Blocking of EGF binding ($IC_{50}$ [nM]) | Blocking of TGFα binding ($IC_{50}$ [nM]) |
|---|---|---|
| FS1-60 | 0.606 | 3.8 |
| FS1-65 | 0.465 | 3.7 |
| FS1-67 | 0.475 | 4.0 |

Example 6—Flow Cytometry to Assess Antigen Binding

Figure 2:
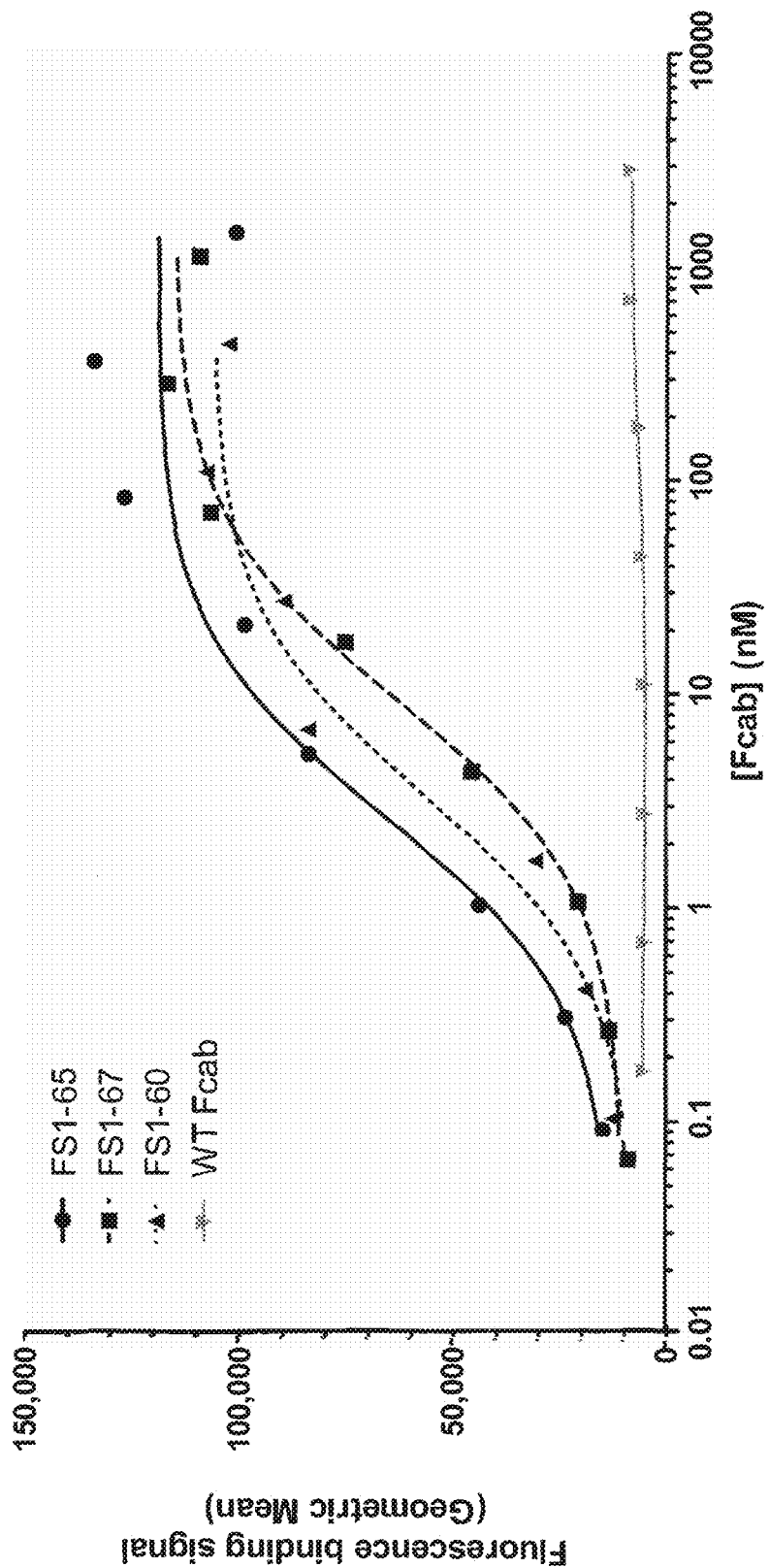
FIG. 2 shows that anti-EGFR Fcabs FS1-60, FS1-65, and FS1-67 bound to EGFR on A431NS cells as measured by flow cytometry. Geometric Mean Fluorescence binding signal was plotted against the Fcab concentration. Fcabs bound to A431 NS cells in a concentration dependent manner whereas WT Fcab did not.

Anti-EGFR Fcabs were tested for binding to cell surface EGFR on A431 NS cells by flow cytometry. Binding of FS1-60, FS1-65 and FS1-67 was assessed by incubating the A431 NS cells with the anti-EGFR Fcabs in flow buffer for 1 hour on ice. Wild type (WT) Fcab (SEQ ID NO: 47) was used as a control. Cells were washed and Fcab binding was detected with an Alexa-Fluo-647®-labelled anti-human IgG secondary antibody (Invitrogen, #A21445) incubated on ice in the dark for 45 minutes. Excess secondary antibody was washed off and the signals were analysed by flow cytometry using an Accuri™ C6 Flow Cytometer (BD Biosciences). Geometric mean fluorescence signal was plotted against Fcab concentration to determine the $EC_{50}$ for each Fcab (FIG. 2). All three anti-EGFR Fcabs bound to A431NS cells in a concentration dependent manner whereas the WT Fcab did not, demonstrating the specificity of these Fcabs for EGFR. The binding affinities of the anti-EGFR Fcabs are summarised in Table 5.

TABLE 5

Binding affinity of anti-EGFR Fcabs to A431NS cells by flow cytometry

| Fcab | Cell binding ($EC_{50}$ [nM]) |
|---|---|
| FS1-60 | 3.3 |
| FS1-65 | 2.6 |
| FS1-67 | 8.9 |

Example 7—Anti-EGFR Fcab-Mediated Antibody-Dependent Cell-Mediated Cytotoxicity (ADCC)

When the Fc effector portion of a target-bound antibody or Fcab simultaneously binds to an FcγRIIIa receptor on the cell surface of an effector cell, it causes cross-linking of the two cells, thereby activating the ADCC pathway, leading to activation of the nuclear factor of activated T-cells (NFAT) pathway and finally controlled cell death of targeted cells.

Anti-EGFR Fcabs were tested for binding to FcγRIIIa receptors using SPR. A BIAcore 3000 instrument (GE healthcare) was used and a CM5 chip was coated with 2000 RU of FcγRIIIa (Sino Biological). Concentration ranges of Fcabs (62-1000 nM) were injected in HBS-P buffer (GE Healthcare) at 20 μl/min for 3 min for association followed by 5 min of dissociation flowing with HBS-P buffer. The FcγRIIIa coated chip was regenerated using 10 mM NaOH at 20 μl/min for 15 seconds. The binding affinity ($K_D$) was derived from steady state fit using the BIAevaluation software version 3.2 RC1 (GE Healthcare). The results showed that the anti-EGFR Fcabs bind FcγRIIIa with binding affinities between 277-289 nM (see Table 6).

To determine whether the anti-EGFR Fcabs elicit ADCC, the ADCC Reporter Bioassay was performed (Promega, G7018). The ADCC Reporter Bioassay uses as effector cells engineered Jurkat cells stably expressing the FcγRIIIa receptor and an NFAT response element driving expression of luciferase. ADCC activity is quantified by luciferase production as a result of NFAT activation. The assay was carried out according to the manufacturer's instructions. Briefly, MDA-MB-468 cells (ATCC, HTB-132) expressing EGFR were incubated with increasing concentrations of anti-EGFR Fcabs. Subsequently, ADCC bioassay effector cells were added and incubated for 6 hours at 37° C. in 5% $CO_2$. Finally, the luciferase reagent was added and relative luminescence quantified. The results showed that the anti-EGFR Fcabs mediated ADCC activity with $EC_{50}$ values in the nM range (Table 6), suggesting that ADCC could be one of the mechanisms of action through which these Fcabs exert anti-tumour activity.

TABLE 6

Binding of anti-EGFR Fcabs to FcγRIIIa and the ADCC Reporter Bioassay response of anti-EGFR Fcabs

| Fcab | FcγRIIIa binding (kD) (nM) | ADCC ($EC_{50}$ nM) |
| --- | --- | --- |
| FS1-60 | 286 | 34.1 |
| FS1-65 | 277 | 9.3 |
| FS1-67 | 289 | 13.7 |

Example 8—Biophysical Characterisation of Anti-EGFR Fcabs by Size Exclusion Chromatography Compared to WT Fcab, FS1-60, FS1-65 and FS1-67 have mutations in the AB, CD, and EF loops which allow for target binding. To assess the effects of these mutations on Fcab structure, biophysical characterisation of the anti-EGFR Fcabs was performed. Duplicate Fcab samples were analysed by size-exclusion high performance liquid chromatography (SE-HPLC) on an Agilent 1200 series HPLC system, using a Zorbex GF-250 9.4 mm ID×25 cm column (Agilent). 80 µl aliquots of 1 mg/ml samples were injected and run in 50 mM sodium phosphate, 150 mM sodium chloride, 500 mM l-arginine, pH 6.0 at 1 ml/min for 15 minutes. Soluble aggregate levels were analysed using Chemstation software (Agilent). The Fcabs exhibited symmetrical single peak SE-HPLC profiles, with a column retention time similar to that of WT Fcab (Table 7). These results demonstrated that the mutations in FS1-60, FS1-65 and FS1-67 had minimal effect on Fcab structure, and that these Fcabs are monomeric and do not form soluble aggregates.

TABLE 7

Biophysical characterisation by SE-HPLC

| Fcab | SE-HPLC (monomer %) | Retention time (minutes) |
| --- | --- | --- |
| FS1-60 | 99.2 | 9.963 |
| FS1-65 | 100 | 10.225 |
| FS1-67 | 100 | 10.112 |
| WT | 99.5 | 9.964 |

Example 9—Effect of Anti-EGFR Fcabs on Cell Proliferation

EGFR expressing rhesus lung epithelial cell line 4MBr-5 (ATCC, CCL-208) was employed to investigate the effect of FS1-60, FS1-65 and FS1-67 on cell proliferation. Cell proliferation was quantified using a Cell Proliferation ELISA BrdU (colorimetric) immunoassay (Roche, 11647229001), performed according to manufacturer's instructions (Version November 2004). 4MBr-5 cells were incubated with various concentrations of anti-EGFR Fcabs in the presence of BrdU in Ham's F-12K medium (ThermoFisher 21127022) containing 1% heat inactivated foetal bovine serum (FBS) (ThermoFisher, 10270) and 1 ng/ml recombinant human epidermal growth factor (EGF) (R&D Systems, 236-EG) for 3 days at 37° C. PBS only, WT Fcab, IgG isotype control, and cetuximab (Merck) were included as controls.

Figure 3:
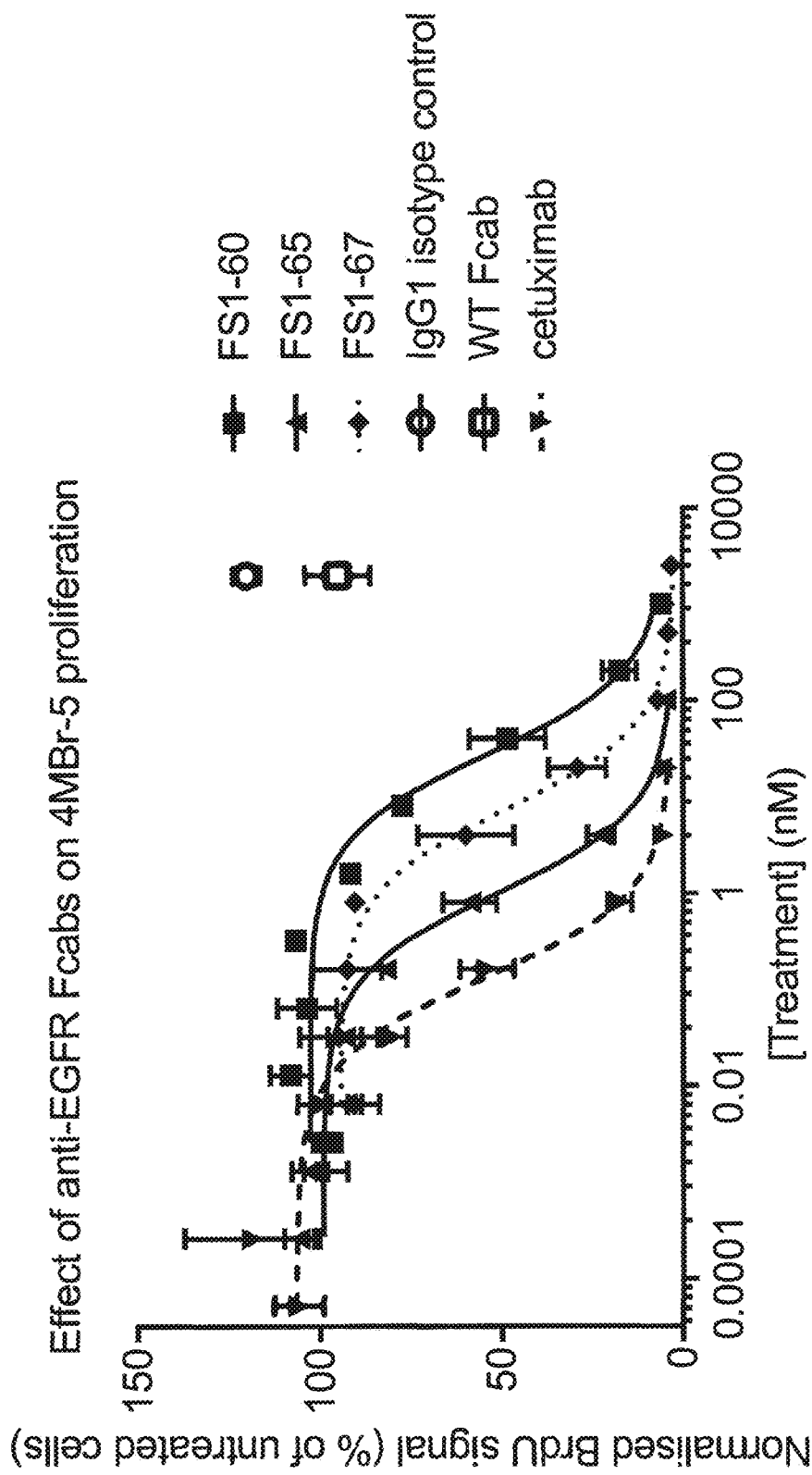
FIG. 3 shows the effect of anti-EGFR Fcabs (FS1-60, FS1-65 and FS1-67), an IgG1 isotype control, WT Fcab and cetuximab on 4MBr-5 cell proliferation. Reduced proliferation of 4MBr-5 cells was observed when cells were treated with increasing concentrations of anti-EGFR Fcabs (FS1-60, FS1-65 and FS1-67), normalised to the PBS control. Treatment with WT Fcab or the IgG1 isotype control did not cause any changes in proliferation of the cells. The BrdU signal in FIG. 3 is the normalised mean and SEM with respect to Fcab concentration. The $IC_{50}$ as determined from the data shown in FIG. 3 was 27.41, 0.99, 7.53, and 0.13 nM for FS1-60, FS1-65, FS1-67, and cetuximab, respectively.

During the 3-day incubation period, BrdU was incorporated into the cells during DNA synthesis. The level of DNA synthesis, due to cell proliferation, was detected by anti-BrdU-peroxidase in an ELISA assay. The results are shown in FIG. 3. FIG. 3 shows that decreased BrdU was detected when cells were treated with increasing concentrations of the anti-EGFR Fcabs or cetuximab. The results were normalised to the PBS control. Treatment of cells with WT Fcab or the IgG1 isotype control (2000 nM) did not result in any changes in BrdU incorporation compared to the PBS control. The $IC_{50}$ for the anti-EGFR Fcabs and cetuximab is shown in Table 8. These data demonstrate that reduced cell proliferation was observed when 4MBr-5 cells were treated with increasing concentrations of anti-EGFR Fcabs.

TABLE 8

Anti-proliferative activities of anti-EGFR Fcabs ($IC_{50}$) on 4MBr-5 cells.

| Fcabs | Anti-cell proliferation ($IC_{50}$) (nM) |
| --- | --- |
| FS1-60 | 27.41 |
| FS1-65 | 0.99 |
| FS1-67 | 7.53 |
| Cetuximab | 0.13 |

Example 10—In Vivo Efficacy Studies: Anti-EGFR Fcab Treatment in the EGFR-Driven Human Patient-Derived Lung Adenocarcinoma Xenograft Model LXFA 677

The in vivo efficacy of anti-EGFR Fcabs was evaluated using mice bearing human patient-derived xenograft (PDX) tumours. Immunodeficient NMRI nude mice (Charles River) were implanted with tumours at approximately 5-7 weeks old. The LXFA 677 PDX (Oncotest), expressing EGFR, was derived from a primary lung adenocarcinoma from a 62 year old male patient. Tumour fragments (3-4 mm edge length) were used for unilateral or bilateral subcutaneous implantation in the flank of the mice. At day 0, tumour-bearing animals were randomily assigned to experimental groups to give mean group tumour volumes of 100-120 mm³ at the beginning of the dosing schedule.

Groups of seven mice were treated with the following: FS1-60, FS1-65, FS1-67, WT Fcab, cetuximab, or PBS (as a vehicle control). The Fcabs and cetuximab were dosed at 20 mg/kg and the vehicle was dosed at 10 ml/kg. Seven doses of each treatment were administered intravenously over two weeks. Tumour volumes were monitored twice weekly until day 87 using a caliper to measure the tumours two-dimensionally (diameter×height). Tumour volumes were calculated according to the formula: (diameter× $height^2$)×0.5. Animals were sacrificed if the tumour volume exceeded 2000 $mm^3$.

Figure 4:
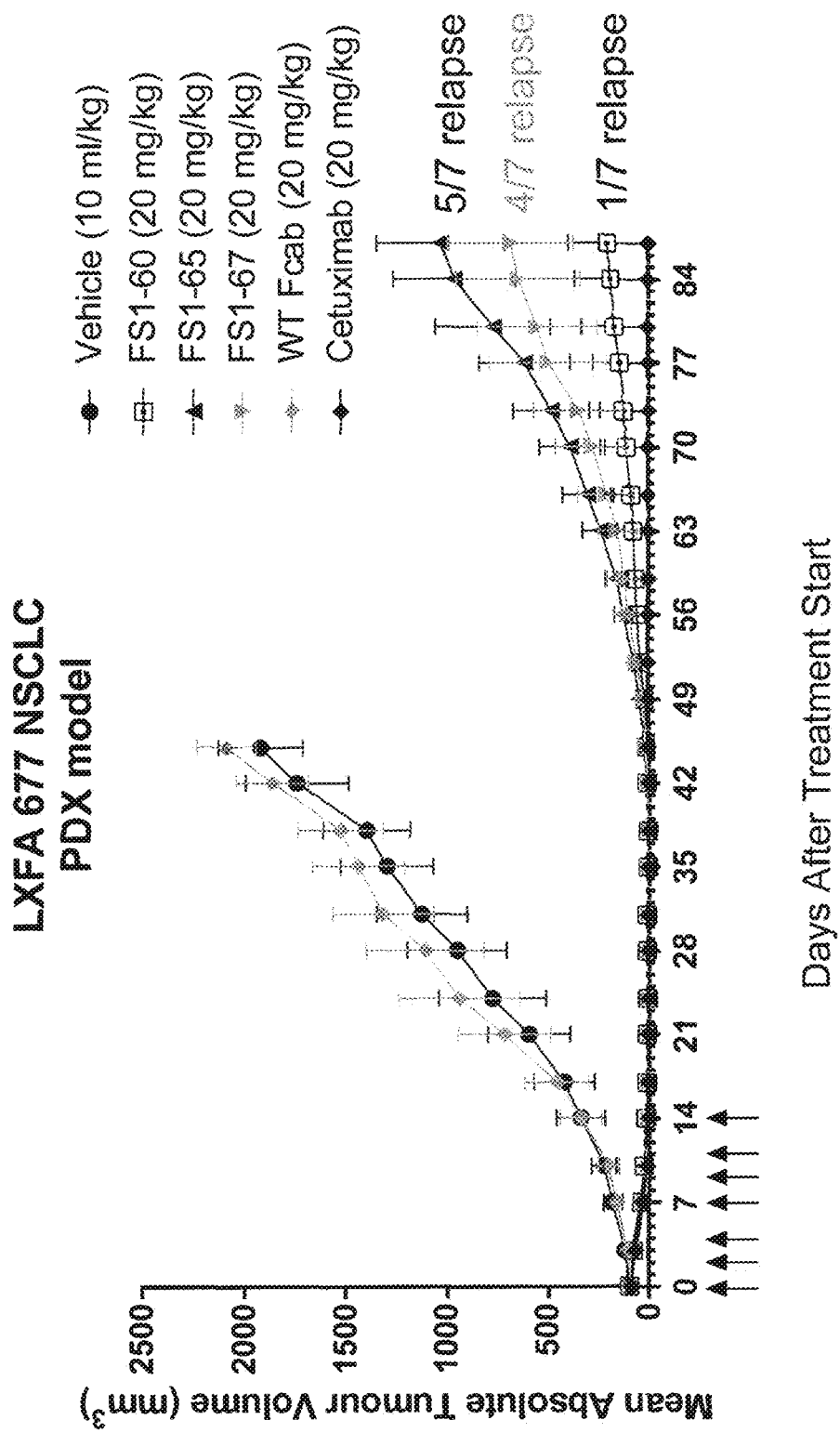
FIG. 4 shows the anti-tumour efficacy of FS1-60, FS1-65, FS1-67, cetuximab and WT Fcab in mice bearing human patient derived xenograft (PDX) tumours. Mice were dosed on days 0, 2, 4, 7, 9, 11 and 14, as indicated by arrows in FIG. 4. The mean absolute tumour volumes over time in mice subjected to each treatment are shown. Tumour measurements were taken twice a week. All mice treated with anti-EGFR Fcabs and cetuximab showed complete tumour regression. The number of mice that had tumour relapse is indicated on the right of the graph (e.g. 1 out of 7 mice treated with FS1-60 relapsed).

All three anti-EGFR Fcabs, as well as cetuximab, caused complete tumour remission in all treated mice, whereas the WT Fcab did not display any anti-tumour efficacy (FIG. 4). Tumour inhibition by all anti-EGFR Fcabs, as well as cetuximab, relative to the vehicle control and/or the WT Fcab-treated groups was statistically significant (Kruskal-Wallis/Dunn's) (Table 9). Four weeks after the last dose, tumour regrowth was observed in some, but not all, animals treated with the anti-EGFR Fcabs (1 of 7 relapsed after treatment with FS1-60, 4 of 7 after treatment with FS1-67 and 5 of 7 relapsed after treatment with FS1-65). For the tumours which had not regrown, measurement was continued and complete remission continued to the end of the study at day 87. A statistically significant delay in tumour growth of 400% was observed for all Fcab treatments relative to the vehicle control group, as well as the WT Fcab-treated group (Kaplan-Meier). In conclusion, at well-tolerated dose levels, all three Fcabs caused complete remission in the EGFR-dependent PDX model LXFA 677.

TABLE 9

Statistical comparison of Fcabs efficacy in LXFA677 in vivo study

| | Significance relative to | | | |
|---|---|---|---|---|
| | FS1-60 (20 mg/kg) | FS1-65 (20 mg/kg) | FS1-67 (20 mg/kg) | Cetuximab (20 mg/kg) |
| Tumour inhibition - Kruskal-Wallis/Dunn's | | | | |
| Vehicle control | P < 0.05 | P < 0.01 | P < 0.05 | P < 0.05 |
| WT Fcab | P < 0.05 | P < 0.01 | P < 0.05 | Not available |
| Delay in tumour growth - Kaplan-Meier | | | | |
| Vehicle control | P = 0.0001 | P = 0.0001 | P = 0.0001 | P = 0.0001 |
| WT Fcab | P = 0.0002 | P = 0.0002 | P = 0.0002 | Not available |

Example 11—Preparation of mAb$^2$ Molecules

EGFR/HGF mAb$^2$ Preparation

The mAb$^2$ molecules RI/FS1-60 (heavy chain: SEQ ID NO: 41; light chain: SEQ ID NO: 28), FI/FS1-60 (heavy chain: SEQ ID NO: 42; light chain: SEQ ID NO: 38), RI/FS1-65 (heavy chain: SEQ ID NO: 43; light chain: SEQ ID NO: 28) and FI/FS1-65 (heavy chain: SEQ ID NO: 44; light chain: SEQ ID NO: 38) were prepared by replacing the CH3 domains of the monoclonal antibodies rilotumumab (RI) and ficlatuzumab (FI) with the CH3 domains of the EGFR specific Fcabs FS1-60 and FS1-65, respectively. For human IgG1 monoclonal antibody FI, the DNA sequence encoding the entire CH3 domain of the antibody was replaced with the CH3 domain of FS1-60 or FS1-65 Fcab. For human IgG2 monoclonal antibody RI, the same method was used.

The gene sequences encoding the modified CH3 domains of the heavy chains and parental light chains of the monoclonal antibodies RI and FI were synthesized by GeneArt (Life Technologies) with restriction sites HindIII and EcoRI at the 5' and 3' ends respectively for subcloning into GS vector (Lonza). The constructs were transfected into mammalian cells (CHOK1SV GS-KO cells) for soluble protein expression (Lonza). CHOK1SV GS-KO cells were transfected and grown for up to 12 days to allow optimal transient protein expression and secretion. Stable pools were also generated using the CHO GS System™ (Lonza). mAb$^2$ expressed and secreted by the CHOK1 SV GS-KO cells were purified from cell supernatants by Protein A affinity chromatography.

Other mAb$^2$ molecules can be prepared by similarly replacing the CH3 domain sequence of a human antibody, such as FI, RI or HuL2G7 (Galaxy Biotech, see EP 2 016 162 B1), with the CH3 domain sequence of a desired Fcab. Suitable Fcabs, in addition to FS1-60 and FS1-65, include FS1-67.

EGFR/CTLA4 mAb$^2$ Preparation (Used in Example 18)

Figure 5:
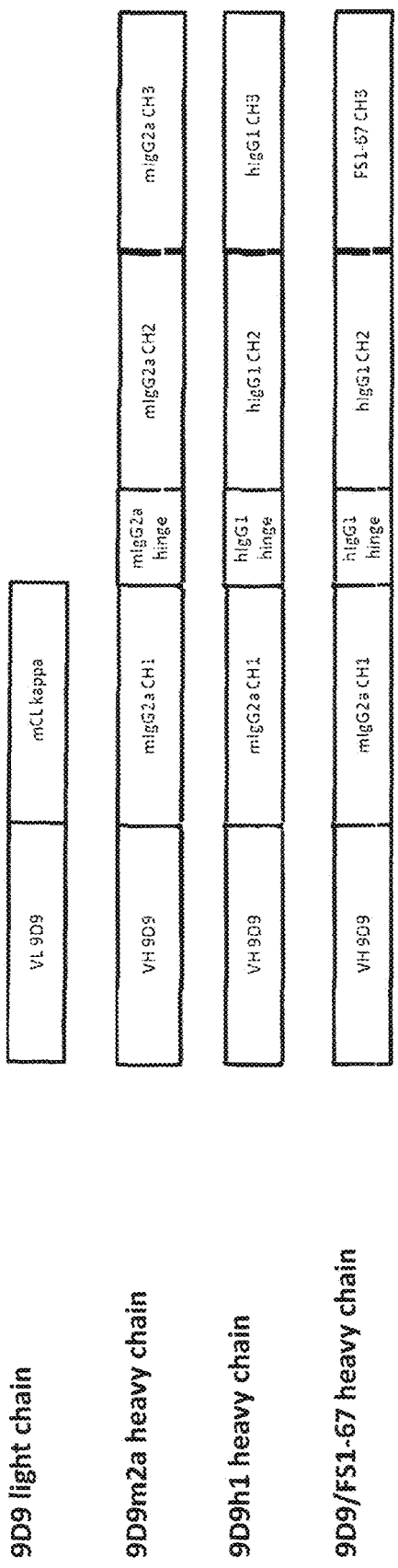
FIG. 5 shows a schematic diagram of the:
1. 9D9 light chain in a mouse kappa light chain backbone (SEQ ID NO: 50)
2. 9D9m2a heavy chain: the 9D9 VH in a mouse IgG2a backbone (CH1-hinge-CH2-CH3) (SEQ ID NO: 52)
3. 9D9h1 heavy chain: the 9D9 VH in a chimeric mouse IgG2a-human IgG1 backbone (mouse IgG2a CH1-human IgG1 hinge-CH2-CH3) (SEQ ID NO: 54)
4. 9D9/FS1-67 heavy chain: the 9D9 VH in a chimeric mouse IgG2a-modified human IgG1 backbone (mouse IgG2a CH1-human IgG1 hinge-CH2-EGFR Fcab FS1-67 CH3) (SEQ ID NO: 56)

The anti-mouse CTLA4 antibody 9D9 variable regions of the heavy (VH) and light chains (VL) were derived from the 9D9 scFv sequence (SEQ ID NO: 48) published in patent application number US2011/0044953A1. The following mAb and mAb$^2$ molecules were designed based on these variable regions and are depicted schematically in FIG. 5.

The gene sequences encoding the 9D9 light chain (SEQ ID NO: 50), 9D9m2a heavy chain (SEQ ID NO: 52), and 9D9/FS1-67 heavy chain (SEQ ID NO: 56) were synthesized by GeneArt (Life Technologies) with restriction sites EcoRI and BamHI at the 5' and 3' ends respectively for cloning into the pTT5 (NRCC) expression vector. The 9D9h1 heavy chain gene sequence (SEQ ID NO: 54) was designed to include an XhoI site between DNA sequence encoding CH2 and CH3 domains to allow for subcloning of different CH3 domains by XhoI/BamHI digestion and DNA ligation. The constructs were transfected into mammalian cells (293-6E cells, NRCC) for transient soluble protein expression (in-house). 293-6E cells were transfected and grown for up to 5 days to allow optimal protein expression and secretion. The encoded mAb$^2$ expressed and secreted by the 293-6E cells were purified from cell supernatants by Protein A affinity chromatography. Stable pools were also generated using the CHO GS System™ (Lonza).

Other mAb$^2$ molecules can be prepared by similarly replacing the CH3 domain sequence of a human antibody, such as ipilimumab (light chain SEQ ID NO: 58 and heavy chain SEQ ID NO: 60) with the CH3 domain sequence of a desired antigen-binding Fc (Fcab). Suitable Fcabs include FS1-67, FS1-65 and FS1-60.

Example 12—Blockade of Phosphorylation of EGFR, c-Met and Signalling Protein by Anti-EGFR/HGF mAb$^2$ Anti-EGFR mAb$^2$ FI/FS1-60 and RI/FS1-60 were tested for the ability to block the phosphorylation of c-Met and EGFR and, subsequently, phosphorylation of the secondary messengers mitogen-activated protein kinase (MAPK) and Akt, stimulated by HGF and EGF.

Preparation of Cell Lysates

Overnight cultures of the glioblastoma cell line U87MG (ATCC HTB-14) were moved from a medium with 10% FBS to a low serum medium with 0.1% FBS to optimise sensitivity to ligand stimulation. The cells were incubated overnight. The next day, treatments including FI/FS1-60, RI/FS1-60, FI, RI, FS1-60, IgG1 kappa, a combination of FI+FS1-60 and a combination of RI+FS1-60 at a final concentration of 200 nM (or 200+200 nM for combination) were added to the cells and incubated at 37° C. for 20 min in the presence of 0.6 nM HGF (PeproTech, 100-39) and 1.6 nM EGF (R&D Sytems, 236-EG) for stimulation. Controls without antibody treatment were included, with and without growth factor stimulation. The treated cells were lysed using lysis buffer (10 mM Tris® pH7.5, 150 mM NaCl, 1 mM EDTA) comprising 1:100 protease inhibitor cocktail (Calbiochem, 539131) and 1:100 Phosphatase inhibitor cocktail (Calbiochem, 524625) and the lysates collected for analysis.

Western Blotting

Lysate samples were subjected to standard western blotting analysis using a 4-12% Bis-Tris® protein gel (ThermoFisher, NP0322BOX) and transferred to a nitrocellulose membrane (ThermoFisher, IB301001). The membrane was blocked with 5% Marvel milk/TBST and then probed for phospho-c-Met using a rabbit monoclonal antibody specific for c-Met phosphorylated at Tyr1234/1235 (Cell Signaling, 3077), phospho-EGFR using a mouse monoclonal antibody specific for EGFR phosphorylated at Tyr1068 (Cell Signaling, 2236), phospho-MAPK using a mouse monoclonal antibody specific for p44/42 MAPK (ERK1/2) phosphorylated at Thr202/Tyr204 (Cell Signaling, 9106), and phospho-Akt using a rabbit monoclonal antibody specific for Akt phosphorylated at Ser473 (Cell Signaling, 9271). The membranes were washed and secondary antibody conjugated to HRP (anti-mouse, Jackson ImmunoResearch, or anti-rabbit Jackson ImmunoResearch) was added before reacting with an enhanced chemiluminescence substrate (ThermoFisher, 34076) for signal detection. GAPDH was probed on the same membrane as a loading control using a mouse monoclonal anti-GAPDH antibody (Sigma-Aldrich, G8795).

Figure 6:
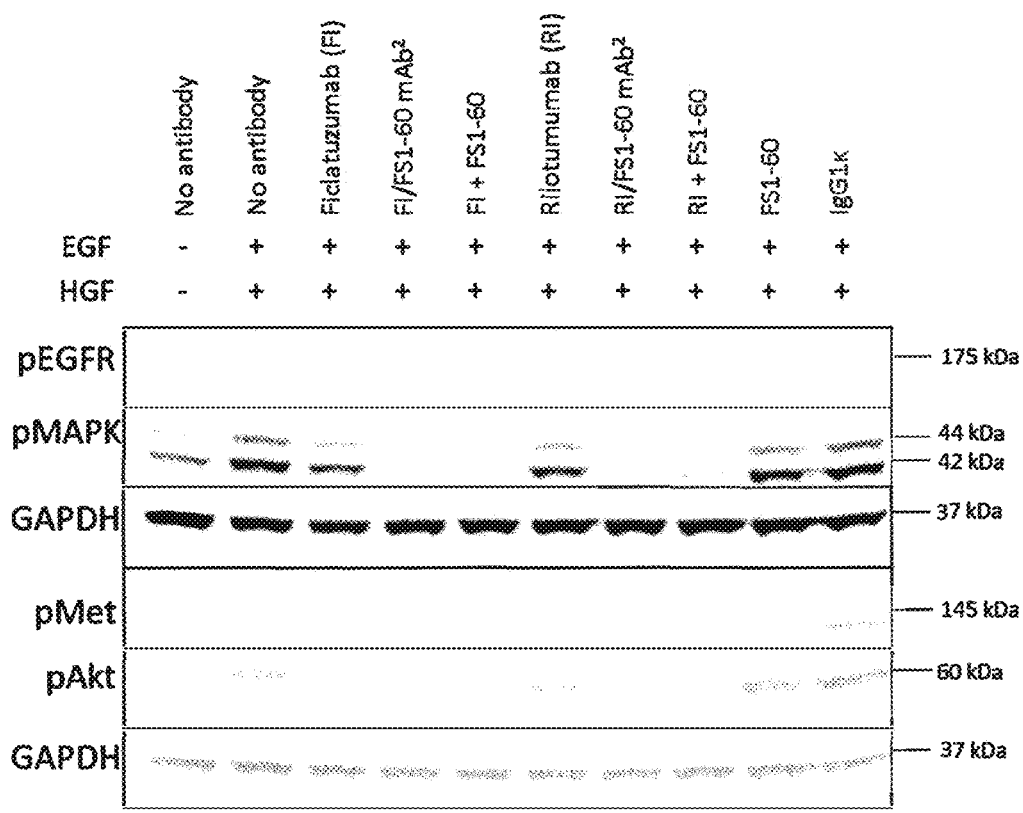
FIG. 6 shows that the FI/FS1-60 $mAb^2$ and the RI/FS1-60 $mAb^2$ inhibit phosphorylation of Met (pMet) and signalling protein MAPK (pMAPK) in U87MG human primary glioblastoma cells. Cells were treated with FI/FS1-60, RI/FS1-60, ficlatuzumab (FI), rilotumumab (RI), FS1-60, a combination of ficlatuzumab and FS1-60 (FI+FS1-60), a combination of rilotumumab and FS1-60 (RI+FS1-60), or isotype control IgG1 kappa (IgG). Addition of HGF or EGF is indicated by "+", absence of HGF or EGF is indicated by "−". GAPDH was used as a loading control. When stimulated by both HGF and EGF, only the $mAb^2$ molecules, and FI or RI in combination with the EGFR-binding Fcab blocked the phosphorylation of down-stream signalling molecules MAPK and Akt. FI/FS1-60 and RI/FS1-60 are able to inhibit the phosphorylation of c-Met and EGFR.

The results are shown in FIG. 6 and demonstrate that HGF stimulates the phosphorylation of c-Met and subsequent phosphorylation of MAPK and Akt. EGF stimulates the phosphorylation of EGFR and also subsequent phosphorylation of MAPK and Akt. Like FI and RI, the mAb$^2$ molecules were able to block the phosphorylation of c-Met by HGF. Blocking of phospho-c-Met leads to blocking of phospho-MAPK and phospho-Akt. However, this can be overcome by stimulation of EGFR by EGF, resulting in phosphorylation of MAPK and Akt. Therefore, FI and RI are unable to block the phosphorylation of MAPK and Akt in the presence of EGF. Likewise, FS1-60 alone is unable to block the phosphorylation of MAPK and Akt in the presence of HGF. When stimulated by both HGF and EGF, only the mAb$^2$ molecules, and FI or RI combination with FS1-60 were able to block the phosphorylation of down-stream signalling molecules MAPK and Akt. These results demonstrated that FI/FS1-60 and RI/FS1-60 are able to inhibit the phosphorylation of c-Met and EGFR, and therefore also down-stream signalling, more efficiently than FI, RI or FS1-60 alone. The blockade of the activation of these receptor tyrosine kinases could is expected to inhibit cell proliferation, cell migration and cell survival.

Example 13—Simultaneous Bi-Specific Binding of mAb$^2$ Molecules

The ability of the mAb$^2$ molecules to simultaneously bind to their two cognate antigens was measured by SPR using a BIAcore 3000 instrument (GE healthcare).

Figure 7:
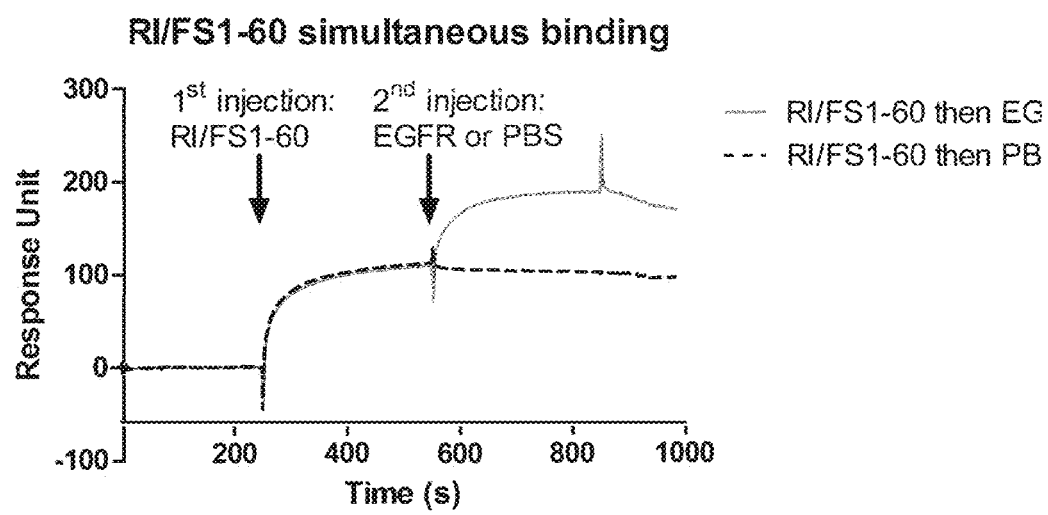
FIG. 7 shows that $mAb^2$ RI/FS1-60 (FIG. 7A) and $mAb^2$ FI/FS1-60 (FIG. 7B) are capable of binding to both of their cognate antigens simultaneously as measured by surface plasmon resonance. $mAb^2$ were flowed over an HGF coated chip and His-tagged EGFR was subsequently injected. The binding response shows that the $mAb^2$ can bind to both HGF and HGFR simultaneously.
Figure 7:
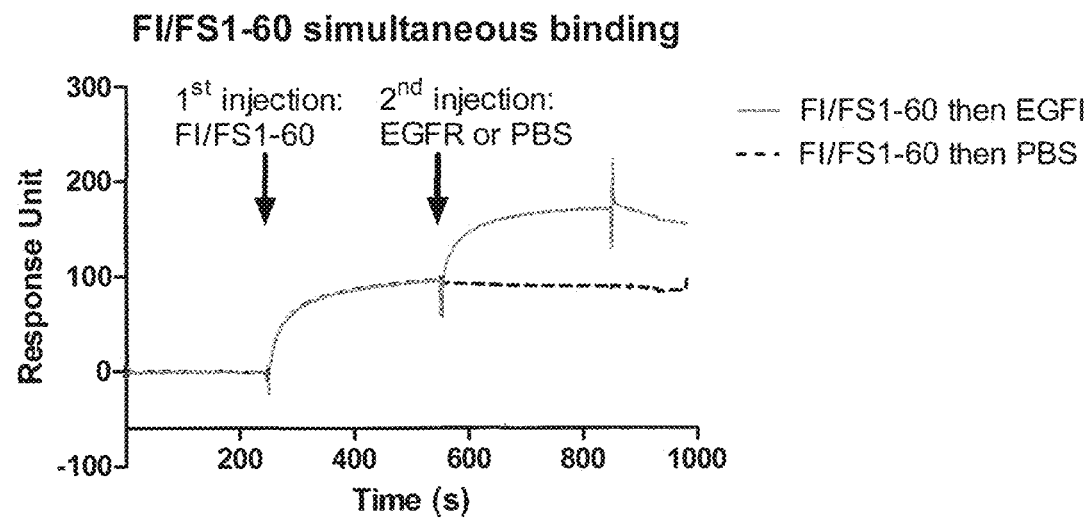

A CM5 chip was coated with 1200 RU of HGF using standard amine coupling. In the first injection step, RI/FS1-60 mAb$^2$ or FI/FS1-60 mAb$^2$ (500 nM) was injected at 20 μl/min for 5 min to allow binding saturation to HGF coated on the chip. In the second injection step, 20 μg/ml His-tagged EGFR was injected at 20 μl/min for 5 min followed by dissociation in HBS-P buffer. The HGF surface was regenerated using 40 mM NaOH at 45 μl/min for 17 sec, repeated three times. The binding response of EGFR in the second injection step on the saturated HGF chip showed that the RI/FS1-60 and FI/FS1-60 mAb$^2$ can bind to HGF and EGFR simultaneously (FIG. 7).

Example 14—Blocking of EGF Binding to EGFR by Anti-EGFR/HGF mAb$^2$

Figure 8:
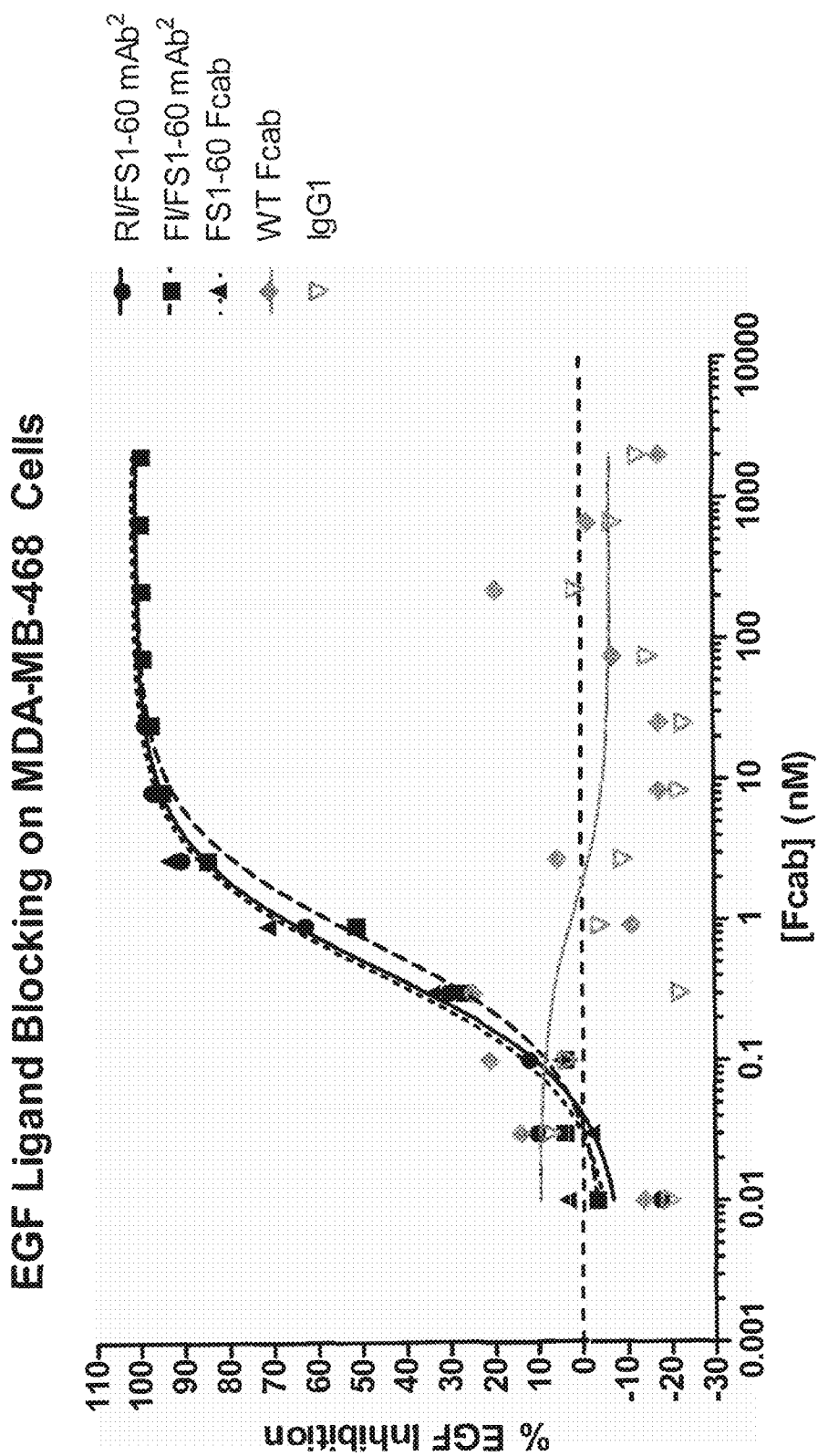
FIG. 8 shows that $mAb^2$ RI/FS1-60 and $mAb^2$ FI/FS1-60, as well as the FS1-60 Fcab block binding of the EGF ligand to EGFR on MDA-MB-468 breast cancer cells that overexpress EGFR. Percentage inhibition of ligand binding to EGFR is shown compared to PBS control, where PBS results in 0% inhibition.

Anti-EGFR/HGF mAb$^2$ FI/FS1-60 and RI/FS1-60 were tested for the ability to block binding of the ligand EGF to EGFR-expressing MDA-MB-468 cells. The same method as described in Example 5 was used but employing MDA-MB-468 cells instead of A431 NS cells. The following were tested: mAb$^2$FI/FS1-60, mAb$^2$ RI/FS1-60, FS1-60 Fcab, human IgG1 (IgG1), or WT Fcab at a various concentrations (25-0.002 nM) with PBS as a control. FIG. 8 shows the percentage inhibition of EGF binding to EGFR normalised to the PBS control, where PBS has 0% inhibitory activity.

The results demonstrate that EGFR mAb$^2$ FI/FS1-60 and RI/FS1-60 blocked EGF binding to EGFR with an IC$_{50}$ between 0.45 to 0.71 nM (Table 10). This is comparable to the IC$_{50}$ of the FS1-60 Fcab. These data show that the EGF blocking activity of the anti-EGFR Fcab was not affected by its insertion into the mAb$^2$ format.

TABLE 10

| mAb$^2$ or Fcab | Blocking of EGF binding to EGFR, IC$_{50}$ (nM) |
| --- | --- |
| RI/FS1-60 | 0.45 |
| FI/FS1-60 | 0.71 |
| FS1-60 | 0.43 |

Example 15—Effect of Anti-EGFR/HGF mAb$^2$ on Cell Proliferation of Cancer Cell Lines Four cancer cell lines were employed to test the effect of anti-EGFR/HGF mAb$^2$ on cell proliferation.

U87MG Cells

Glioblastoma U87MG cells (autocrine production of HGF) were incubated with various concentrations of FI, FI/FS1-60, FI+FS1-60 (1:1 combination), RI, RI/FS1-60, RI+FS1-60 (1:1 combination), FS1-60, human IgG1 kappa (IgG), or PBS for 4 days at 37° C. Viable cell count was used to determine the anti-proliferative effect of the different treatments. After 4 days, Hoechst 33342 at 1 μg/ml (Invitrogen, H3570) and propidium iodide (PI) at 2.5 μg/ml (Sigma, P4864) was added to the cells and the cells incubated in the dark for 25 min at room temperature to stain nuclei for total cell count and for dead cells respectively. Viable cell numbers were determined using an ImageXpress® Micro (IXM) microscope (Molecular Devices) at 4× magnification.

Figure 9:
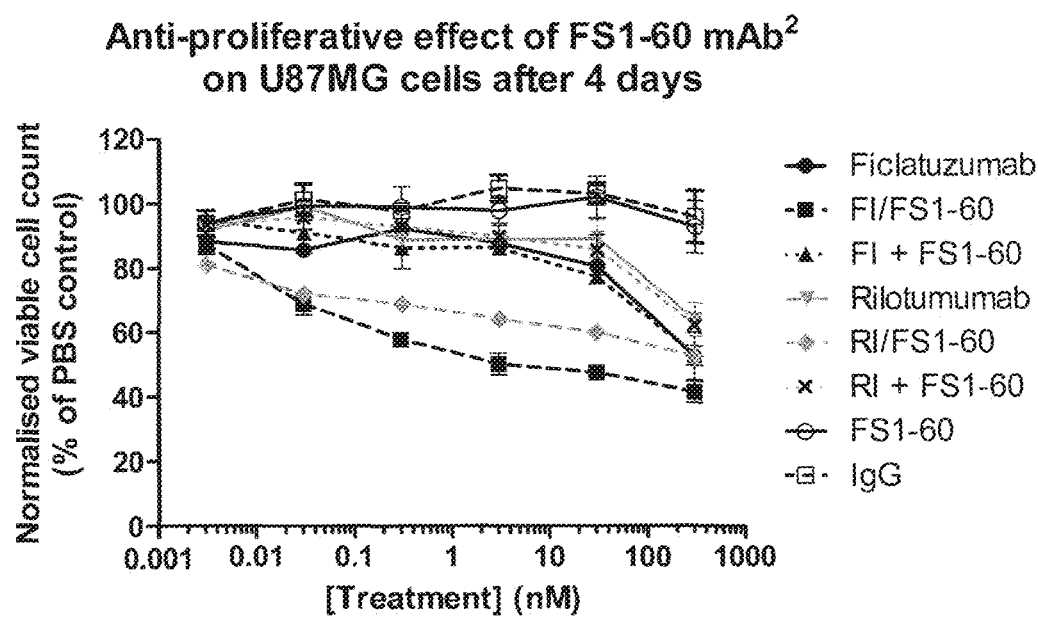
FIG. 9 shows that $mAb^2$ FI/FS1-60, RI/FS1-60, FI/FS1-65 and RI/FS1-65 have anti-proliferative activity in different cell lines.
Figure 9:
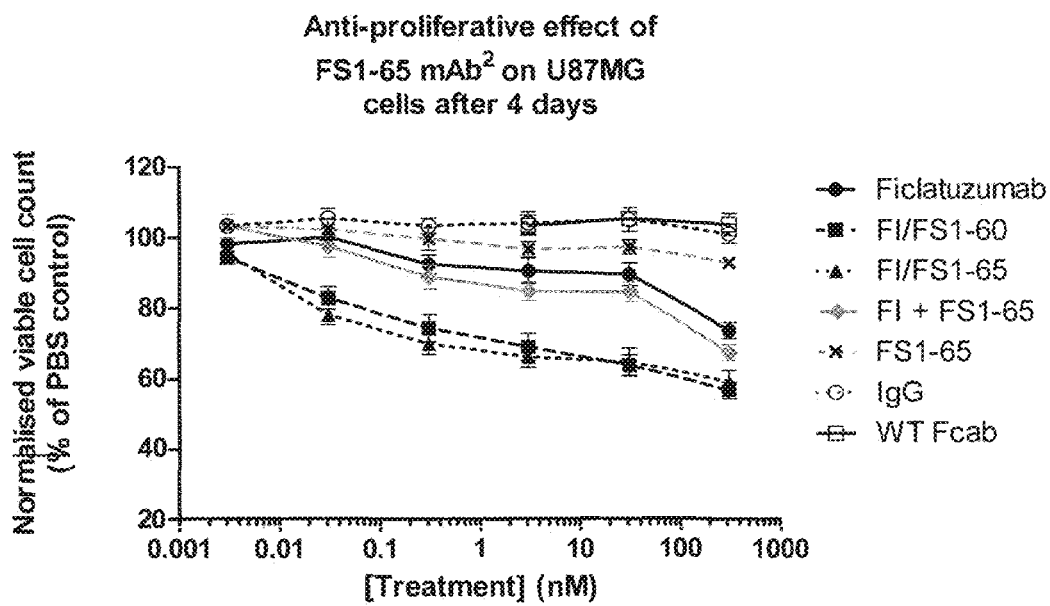
Figure 9:
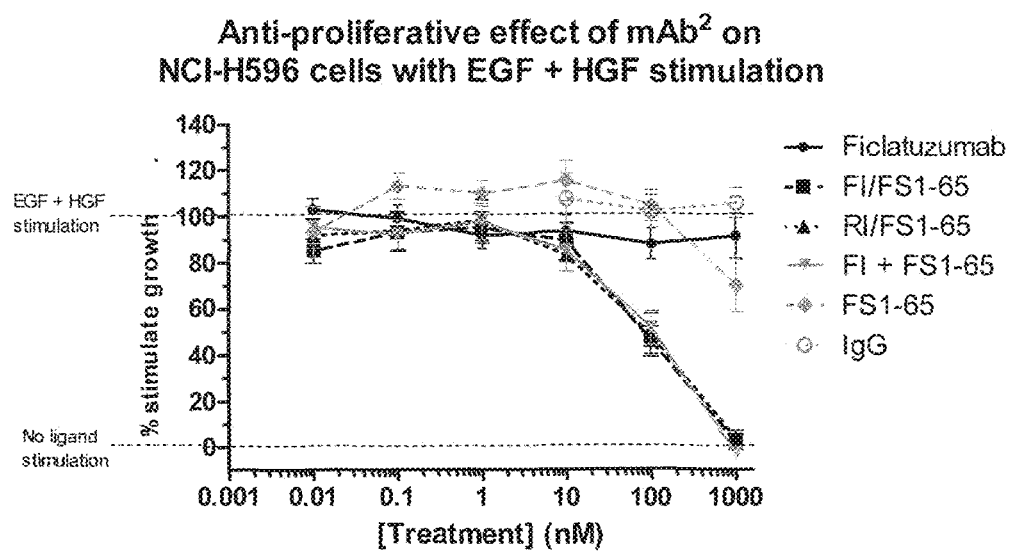
Figure 9:
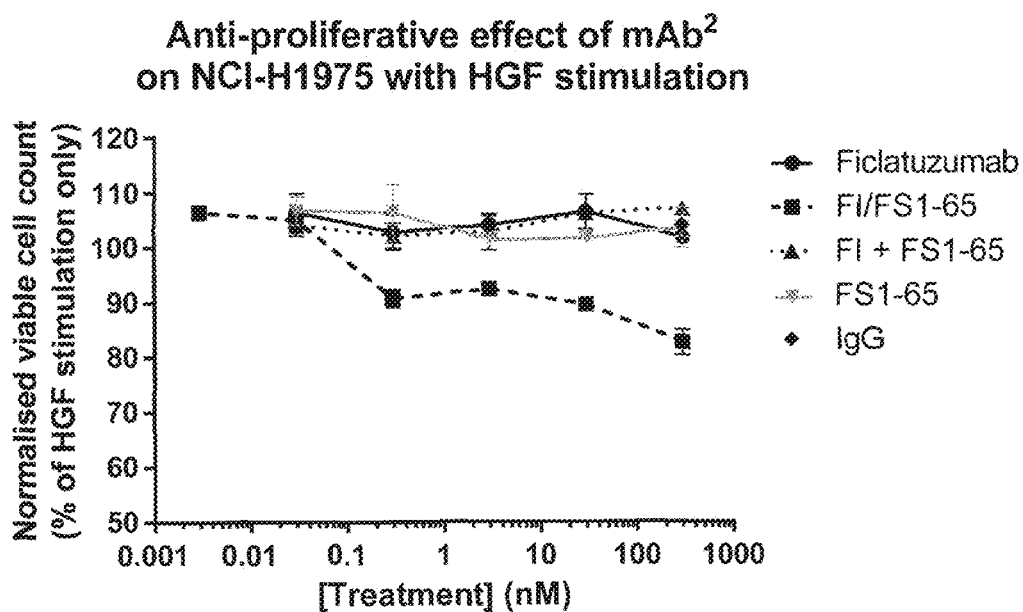
Figure 9:
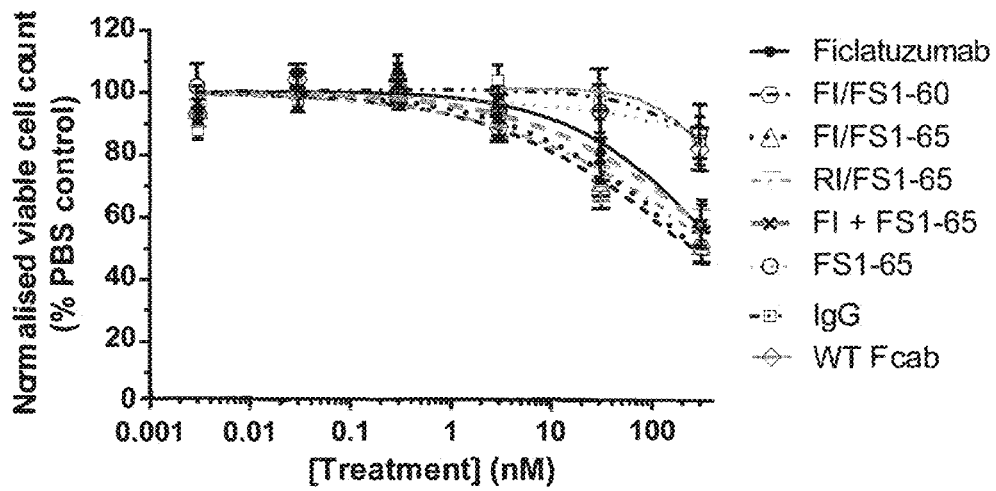
Figure 9:
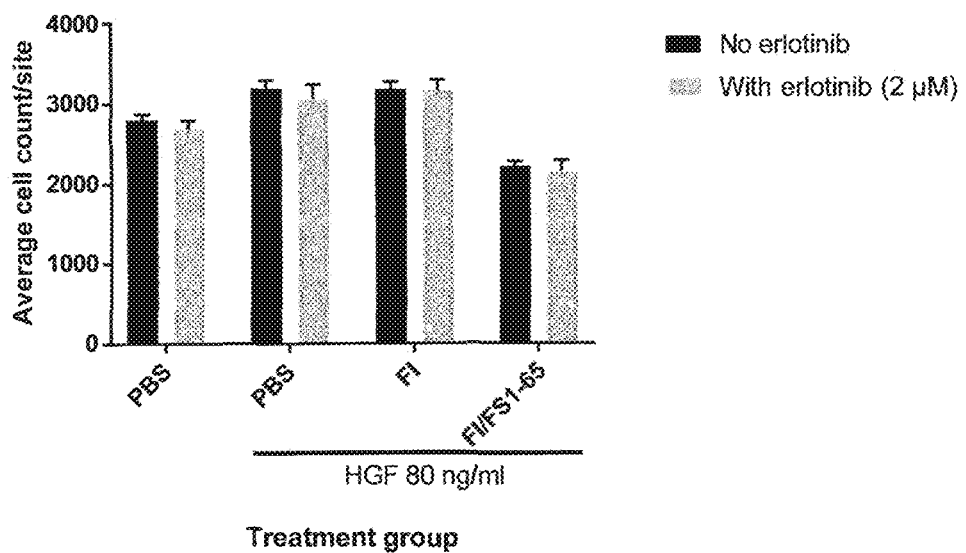
Figure 9:
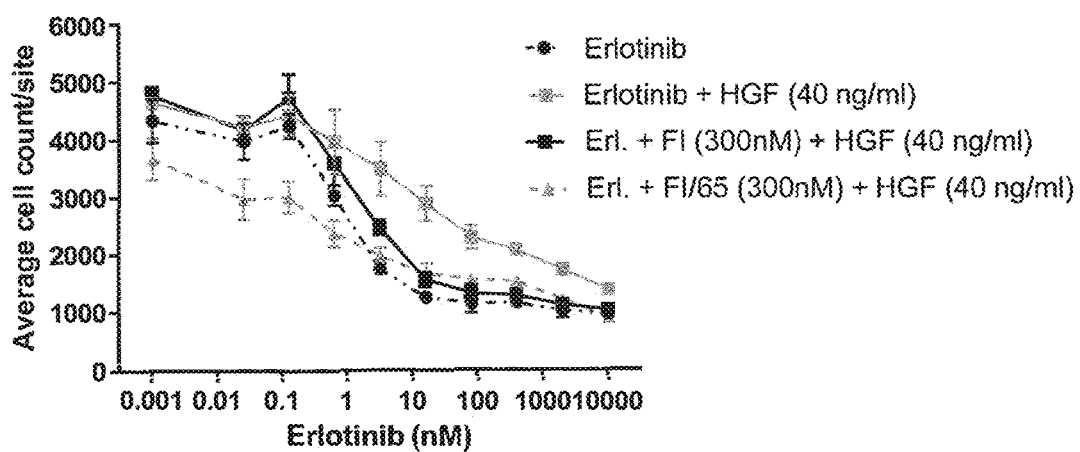

A concentration-dependent reduction in cell proliferation was observed in the presence of mAb$^2$ FI/FS1-60 and RI/FS1-60 (FIG. 9A). FI/FS1-60 and RI/FS1-60 had superior efficacy when compared to monotherapy with FI, RI or FS1-60 Fcab. FI/FS1-60 and RI/FS1-60 mAb$^2$ were superior to the treatment with FI+FS1-60 or RI+FS1-60. The assay was repeated with another mAb$^2$, FI/FS1-65, and the results reflected those observed with the FI/FS1-60 mAb$^2$ (FIG. 9B). These data showed that mAb$^2$ FI/FS1-60, RI/FS1-60 and FI/FS1-65 have anti-proliferative activity in HGF autocrine U87MG cells.

NCI-H596 Cells

NCI-H596 (ATCC HTB-178) is a lung adenosquamous cancer cell line that engages both the EGF and HGF signalling pathways and was used to investigate the ability of mAb$^2$ molecules to block proliferation. The same method was used as in the U87MG assay described above, except that the NCI-H596 cells were stimulated with both EGF and HGF ligands. One day before the treatment, the level of FBS used in the media was reduced from 10% to 1%. The next day treatments were added at various concentrations (10-1000 nM) in the presence of 2 ng/ml EGF (R&D systems, 236-EG) and 12 ng/ml HGF (PeproTech, 100-39) and incubated for 3 days at 37° C. Controls of HGF+EGF, EGF only, HGF only and no ligand stimulation were also included. The results show that FI/FS1-65 and RI/FS1-65 mAb$^2$ inhibit cell proliferation induced by HGF and EGF in a concentration dependent manner (FIG. 9C). At 1000 nM, FI/FS1-65, RI/FS1-65 and FI+FS1-65 combinations fully blocked the cell proliferation induced by ligand stimulation. On the contrary, monotherapy with FS1-65 or FI alone was unable to block stimulation when both ligands were present. These data demonstrate that the bispecific anti-EGFR/HGF mAb$^2$ FI/FS1-65 and RI/FS1-65 were efficacious in inhibiting EGF and HGF induced proliferation.

NCI-H1975 Cells

NCI-H1975 (ATCC CRL-5908) is a non-small cell lung cancer (NSCLC) cell line which expresses constitutively active mutated EGFR L858R and EGFR T790M (Kobayashi et al 2005). These mutations are acquired secondary mutations known to confer resistance to EGFR tyrosine kinase inhibitor (TKI) therapies in NSCLC patients. The NCI-H1975 cell line also expresses c-Met. The cell line was used to investigate the ability of mAb$^2$ molecules to block proliferation stimulated by HGF. The same method was used as in the U87MG assay described above, except that the NCI-H1975 cells were stimulated with HGF. One day before the treatment, the medium used was changed from containing 10% FBS to containing no serum. Treatments were added at various concentrations (0.003-300 nM) in the presence of 80 ng/ml HGF and incubated for 3 days at 37° C. The results show that treatment with FI/FS1-65 mAb$^2$ reduced cell proliferation induced by HGF in a concentration dependent manner (FIG. 9D). No effect was observed with the other treatments tested. These data demonstrated that the bispecific FI/FS1-65 mAb$^2$ was efficacious in inhibiting cell proliferation in NCI-H1975 cells harbouring EGFR activating mutations.

The NCI-H1975 cell line was also used to investigate the ability of the FI/FS1-65 mAb$^2$ to block proliferation in combination with the EGFR TKI erlotinib. FI and FI/FS1-65 mAb$^2$ were added at 300 nM with and without erlotinib (2 µM). The results show that the ability of FI/FS1-65 mAb$^2$ treatment to reduce cell proliferation induced by HGF (FIG. 9F) was not affected by the presence of erlotinib. No effect was observed with erlotinib, FI or FI+erlotinib treatment. These data demonstrated that the bispecific FI/FS1-65 mAb$^2$ was efficacious and superior to erlotinib in inhibiting cell proliferation in NCI-H1975 cells harbouring EGFR activating mutations.

KP4 Cells

KP4 (Riken RCB1005) is a pancreatic ductal cell carcinoma which has autocrine production of HGF. The cells were incubated at 37° C. in conditions recommended by the supplier with a range of concentrations (0.003-300 nM) of FI, FI/FS1-60, FI/FS1-65, RI/FS1-65, FI+FS1-65 (1:1 combination), FS1-65, human IgG1 kappa (IgG) or WT Fcab for 3 days as indicated in FIG. 9E. After 3 days, cells were analysed using cell proliferation reagent WST-1 (Roche) to determine the number of viable cells as described in the manufacturer's protocol. The stable tetrazolium salt WST-1 is cleaved to a soluble formazan by the glycolytic production of NAD(P)H in viable cells. The amount of formazan dye formed is quantitated at absorbances 450 nm and 630 nm.

A concentration-dependent reduction in cell proliferation was observed with increasing concentration of mAb$^2$ FI/FS1-60, FI/FS1-65, RI/FS1-65, combination of FI+FS1-65 and FI (FIG. 9E). The three mAb$^2$ had superior efficacy when compared to monotherapy of FI or FS1-65. FI/FS1-65 and RI/FS1-65 mAb$^2$ were also superior to treatment with FI+FS1-65. These data showed that mAb$^2$ FI/FS1-60, FI/FS1-65 and RI/FS1-65 have anti-proliferative activity in HGF autocrine KP4 cells.

HCC827 Cells

HCC827 (ATCC CRL-2868) is a lung adenocarcinoma cell line which expresses the activating EGFR E746-A750 deletion and has EGFR copy number amplification (Furugaki et al., 2014). The cell line has been shown to acquire EGFR TKI resistance via MET amplification (Shien et al., 2015). The cell line was used to investigate the ability of mAb$^2$ and erlotinib to block proliferation stimulated by HGF. The cells were cultured in 10% FBS. One day before the treatment, the FBS was reduced to 1%. Erlotinib (in 0.1% DMSO) was added to the cells at various concentrations (10 µM to 0.0256 nM) in the presence of 40 ng/ml HGF and the cells incubated for 3 days at 37° C. In some tests, 300 nM of FI or FI/FS1-65 mAb$^2$ was added in combination with erlotinib. As a vehicle control, 0.1% DMSO was used. The results show that the presence of HGF confers resistance to erlotinib (FIG. 9G). The effect of this resistance could be cancelled by combining erlotinib with FI, but the combination treatment of erlotinib+FI/FS1-65 further reduced the dose of erlotinib required to inhibit cell proliferation. These results suggest that combining erlotinib treatment with FI/FS1-65 mAb$^2$, but not with FI, could reduce the dose of erlotinib required in treatment and thus reduce potential toxicity.

Example 16—HGF Internalisation and Decrease of HGF Levels in Culture Media Induced by Anti-EGFR/HGF mAb$^2$ Treatment In order to investigate whether internalisation of HGF is the mechanism by which anti-EGFR/HGF mAb$^2$ reduce c-Met activation and inhibit cell proliferation, internalisation of HGF induced by FI/FS1-60 and FI/FS1-65 mAb$^2$ was tested using A431 NS and U87MG cells.

HGF, labelled with Lightning-Link® Rapid DyLight® 488 (Innova Biosciences, 322-0010) according to the manufacturer's instructions, was detected by flow cytometry. 6.5 nM labelled HGF was pre-incubated with 33.3 nM FI/FS1-60 or FI/FS1-65 for 1 h at room temperature. HGF with no mAb$^2$ was used as a control. The mixture was incubated with A431NS cells to bind for 1 h and the incubation was performed on ice to slow down any internalisation activity. Any unbound HGF and mAb$^2$ was removed by washing the cells twice with ice cold PBS (Lonza, BE17-516F) containing 1% BSA (Sigma, A7906). The cells were resuspended in ice cold medium and transferred to 37° C. to speed up internalisation for a period of 180, 120, 60, 30 or 10 min, with one set remaining on ice throughout as a control. At the end of the incubation period, further internalisation was inhibited by washing the cells twice with 0.05% NaN$_3$ (Sigma, S2002) in ice cold DPBS (ThermoFisher, 14040-133) containing 1% BSA. Cell surface-bound labelled HGF was quenched by incubating the cells with 200 nM anti-Alex Fluor 488® IgG (ThermoFisher, A-11094) on ice for 1 h. Internalised, labelled HGF was protected by the cell surface from this quenching, thus any labelled HGF detected was internalised HGF. Cells were stained with NucBlue® Fixed Cell ReadyProbes® Reagent (ThermoFisher, R37606) according to the manufacturer's protocol before being analysed by flow cytometry.

Corresponding experiments were performed with U87MG cells.

Figure 10:
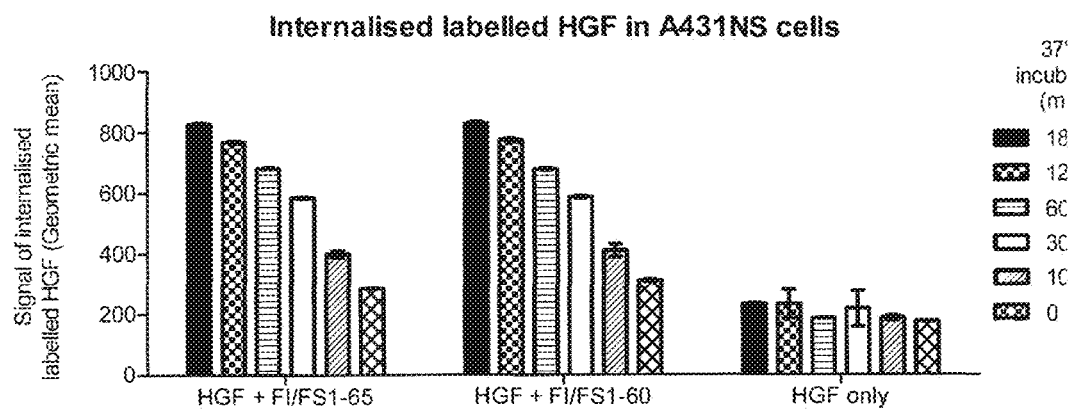
FIG. 10A shows that treatment of EGFR-positive cell line A431 NS with $mAb^2$ FI/FS1-60 and FI/FS1-65 results in internalisation of labelled HGF. The results shown in FIG. 10A indicate greater HGF internalisation with increasing incubation time. No time dependent internalisation was observed in the HGF only group.
FIG. 10B shows a repeat of the same assay using HGF autocrine U87MG cells. Treatment with $mAb^2$ FI/FS1-60 and FI/FS1-65 resulted in time-dependent internalisation of HGF. A small increase in HGF internalisation was detected with time in the absence of mAb² treatment, but at a much slower rate.
FIG. 10C shows the concentration of free HGF in media collected from U87MG cells after a 4-day incubation with the following treatments: PBS control, human IgG1 kappa (IgG), WT Fcab, FS1-65, ficlatuzumab (FI), rilotumumab (RI), a combination of FI+FS1-65 or RI+FS1-65, mAb² FI/FS1-65 and mAb² RI/FS1-65. FI, RI and combinations of these mAbs with FS1-65 lead to a reduction in HGF concentrations in media compared to the PBS control. mAb² FI/FS1-65 and RI/FS1-65 caused a greater reduction in HGF concentration.
Figure 10:
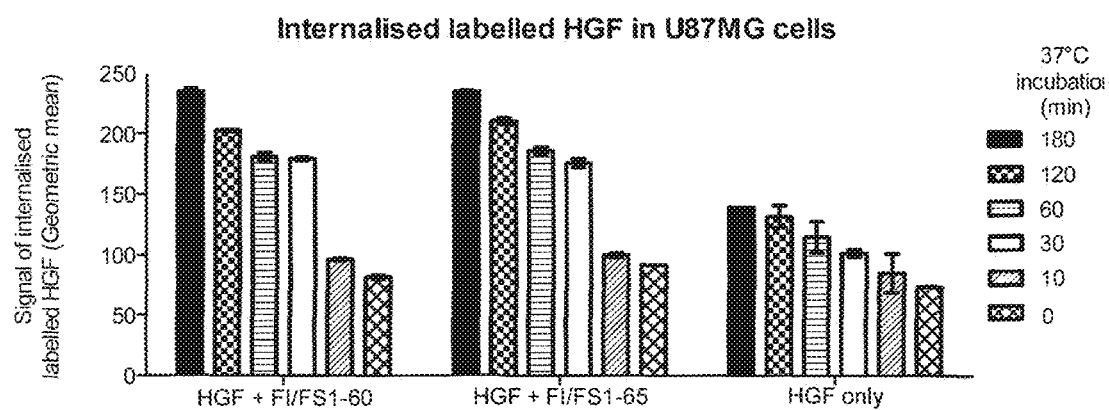
Figure 10:
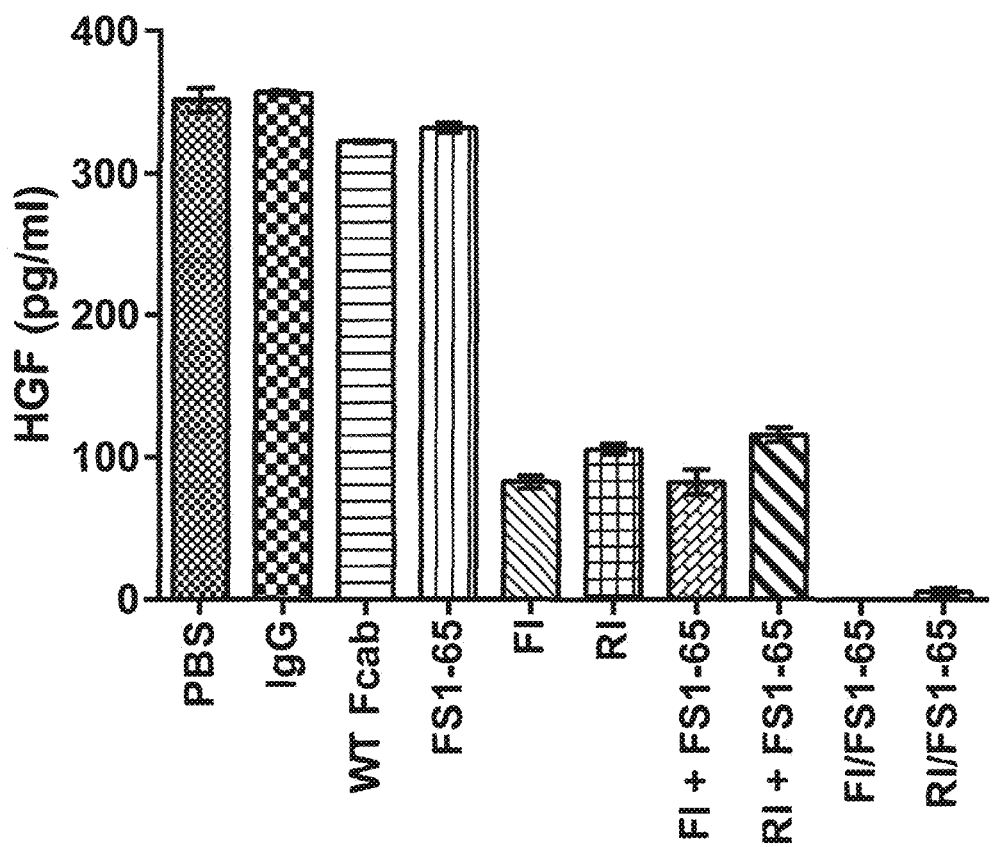

The results show that the signal of labelled HGF increased with incubation time in the presence of mAb$^2$ FI/FS1-60 and FI/FS1-65 (FIGS. 10A and 10B). HGF incubation alone did not change the signal detected regardless of time. Control cells incubated on ice throughout did not show an increase in the HGF signal. These data indicated that mAb$^2$ FI/FS1-60 and FI/FS1-65 facilitated HGF internalisation into the A431NS and U87MG cells, presumably through mAb$^2$ internalisation.

Further, incubation with anti-EGFR/HGF mAb$^2$ was more potent than the combination of HGF targeted mAb+EGFR Fcab in inhibiting the proliferation of U87MG cells (Example 15). It was hypothesised that internalisation of HGF by anti-EGFR/HGF mAb$^2$ leads to reduced level of HGF in the system. To test this hypothesis, the change in level of free HGF caused by incubation with anti-EGFR/HGF mAb$^2$ was examined in U87MG cells that secrete HGF. U87MG cultures were incubated with different treatments at 30 nM for 4 days at 37° C. The treatments were FI/FS1-65, RI/FS1-65, FI, RI, FS1-65, a combination of FI+FS1-65, a combination of RI+FS1-65, WT Fcab, human IgG1 kappa, and PBS control. On day 4, the media from each cell culture were collected for HGF level analysis. HGF concentration was measured using HGF Human ELISA Kit (ThermoFisher, KAC2211) following the manufacturer's protocol. Using monoclonal anti-HGF antibodies, the free HGF in media was detected (free HGF was defined as free HGF in the media which was bound by detection antibodies).

The results show that both FI and RI and their combinations with FS1-65 caused a significant decrease in the concentration of free HGF in the media compared to PBS, IgG, WT Fcab and FS1-65 controls, presumably by sequestering HGF (FIG. 10C). A greater reduction in free HGF levels was observed in the FI/FS1-65 and RI/FS1-65 treated cell cultures. This significant reduction is consistent with the theory that FI/FS1-65 and RI/FS1-65 remove HGF from the media both by internalising HGF into the cells via EGFR binding, as well as by sequestering HGF. This reduction in free HGF levels is expected to lead to more potent effects in inhibiting cell proliferation by mAb$^2$ than observed with the combination treatments.

Example 17—In Vivo Efficacy Studies: Anti-EGFR/HGF mAb$^2$ Treatment of Glioblastoma HGF Autocrine U87MG and NSCLC H596 Xenograft Models Glioblastoma The in vivo efficacy of the bispecific mAb$^2$ targeting EGFR and HGF was evaluated using mice grafted with HGF autocrine U87MG glioblastoma cell line. Female athymic nude mice (CRL: NU(NCr)—Foxn1$^{nu}$, Charles River) were implanted with tumours at approximately 8-12 weeks old. The U87MG glioblastoma was maintained by serial engraftment in the female nude mice. To initiate tumour growth, a 1 mm$^3$ fragment was implanted subcutaneously in the right flank of each test animal. The tumour size was measured with a calliper in two dimensions and the mean volume was calculated using the formula: (width×length)×0.5. Tumours were measured twice weekly for the duration of the study. On Day 0, animals with individual tumour volumes of 75 to 144 mm$^3$ were randomly assigned to six groups, each having eight animals with group mean tumour volumes of 102 mm$^3$. From Day 1, all mice were dosed intravenously twice weekly for up to eight weeks. The six groups of treatments were: PBS vehicle (24.9 ml/kg), FS1-60, FI, a combination of FI+FS1-60, FI/FS1-60 and RI/FS1-60, all at a dose of 60 mg/kg. Animals were euthanised if their tumour exceeded a volume of 2000 mm$^3$.

All treatments, except mice treated with FS1-60 targeting only EGFR, showed tumour remission compared to the vehicle. No differences were observed between FI and the combination of FI+FS1-60. Superior anti-tumour activity was observed in the FI/FS1-60 and RI/FS1-60 mAb$^2$ treated groups over the vehicle, FS1-60 and FI. FI/FS1-60 mAb$^2$ was also superior to the combination treatment of FI+FS1-60. The logrank (Mantel-Cox) and Gehan-Breslow-Wilcoxon tests were used to determine the significance of the difference between the overall survival experiences (survival curves) of the two groups. The results are summarized in FIG. 14. The mean tumour volumes of each group over time are shown in FIG. 11A.

In conclusion, FI/FS1-60 and RI/FS1-60 mAb$^2$ were superior to monotherapies targeting either EGFR or HGF in inhibiting tumour growth. FI/FS1-60 was also superior to the combination treatment of FI+FS1-60 targeting EGFR and HGF.

During the treatment period, serum samples were taken to determine the free human HGF secreted from the xenograft in mice receiving different treatments. On day 16, serum samples from all survivors were collected to be analysed using HGF Human ELISA Kit (ThermorFisher, KAC2211) following the manufacturer's protocol as described in Example 16. The HGF concentrations detected were normalised to the tumour sizes of the corresponding mice.

Figure 11:
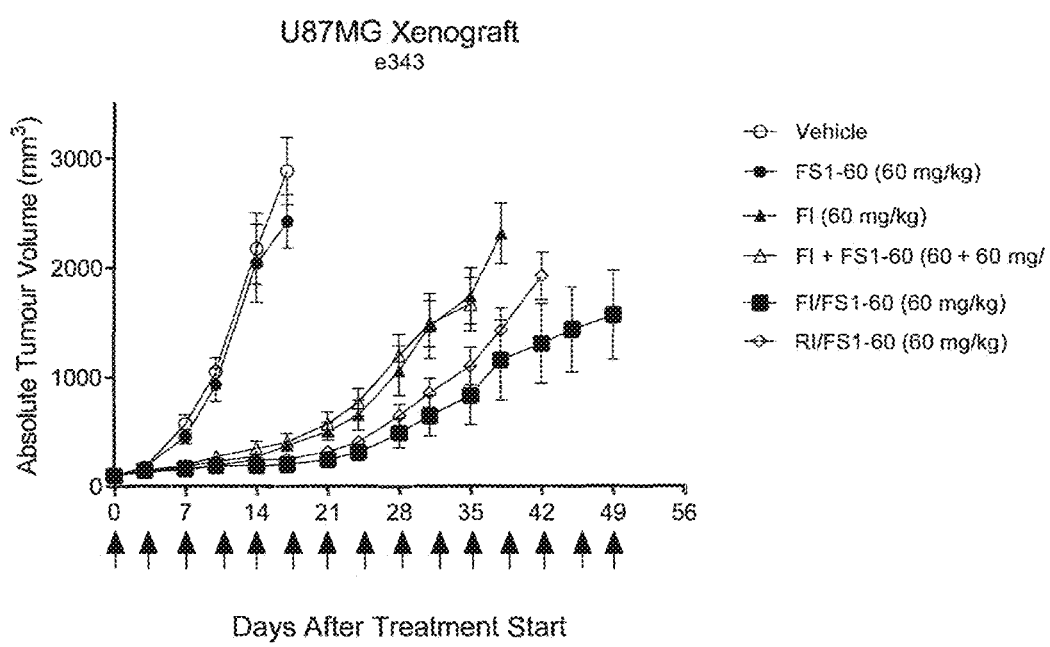
FIG. 11A shows in vivo tumour response data from the HGF autocrine U87MG model. The mean absolute tumour volumes over time are plotted for each treatment group. The arrows indicate the dosing days. Tumour measurements were taken twice a week. FI/FS1-60 and RI/FS1-60 mAb² were superior to monotherapies targeting either EGFR or HGF in inhibiting tumour growth. FI/FS1-60 was also superior to the combination treatment of FI+FS1-60 targeting EGFR and HGF.
FIG. 11B shows in vivo tumour response data from the NSCLC H596 model. The mean absolute tumour volumes over time are plotted for each treatment group. The arrows indicate the dosing days. Tumour measurements were taken twice a week. FI/FS1-60 and FI/FS1-65 mAb² were superior to monotherapies targeting either EGFR or HGF in inhibiting tumour growth.
FIG. 11C shows the survival rate of mice from the NSCLC H596 model during the course of study. The percentage of survival is plotted over time for each group. Mice treated with the two mAb² had higher survival rates compared to those treated with the combination of FI+FS1-65, monotherapy of FS1-65 or the vehicle group. In the group of mice treated with FI/FS1-60, all mice survived at the end of the study.
FIG. 11D show the concentration of free HGF detected in sera from all mice on day 16 after treatment, normalized to the tumour sizes of each mouse. Mice treated with FI/FS1-60 showed significantly reduced level of HGF compared to the vehicle group.
Figure 11:
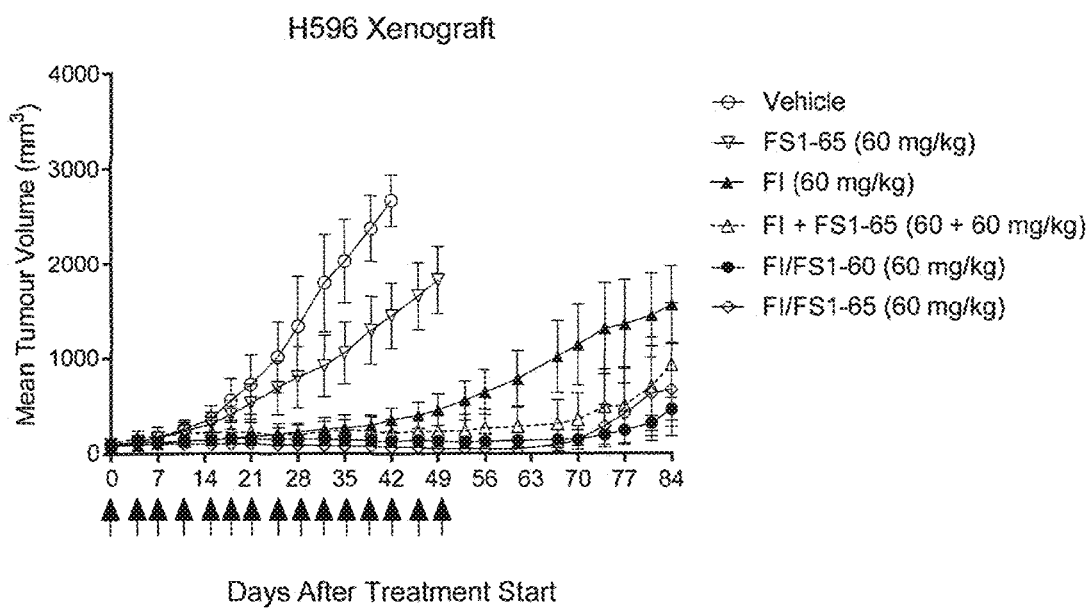
Figure 11:
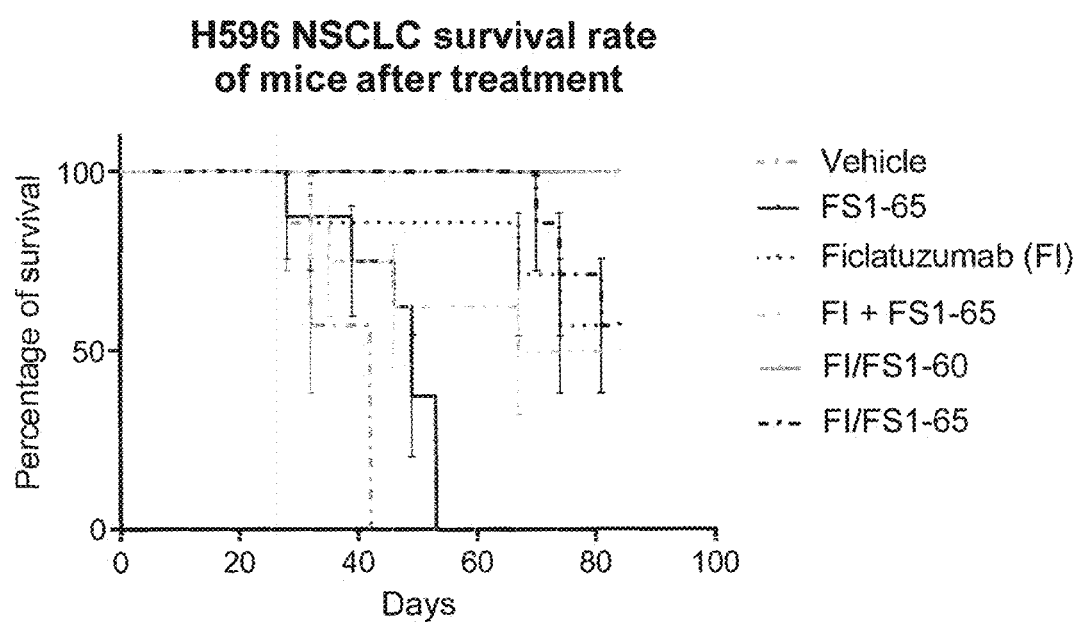
Figure 11:
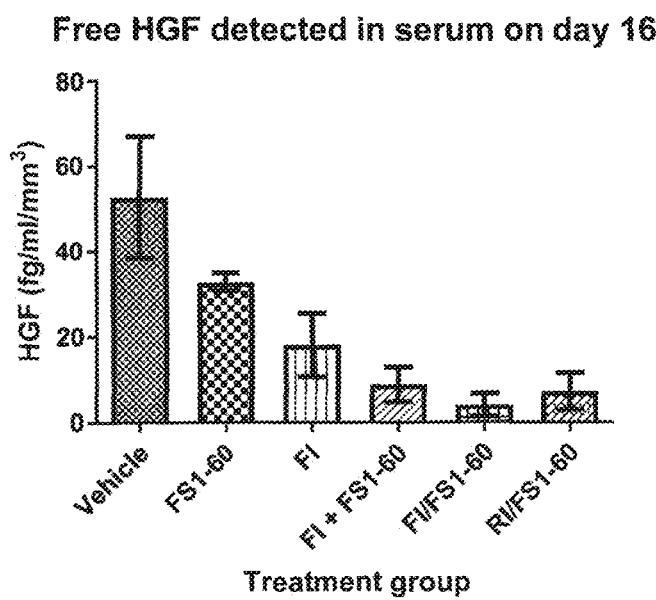

The results show that FI/FS1-60 caused a significant decrease in the concentration of free HGF in the serum compared to the vehicle group (FIG. 11D). A large reduction was observed also in the groups treated with the combination of FI+FS1-60 and RI/FS1-60 compared to the vehicle group, although they were not statistically significant. These observations are consistent with the notion that FI/FS1-60 internalises and sequesters HGF, leading to more potent effects in inhibiting cell proliferation.

NSCLC

One of the challenges of studying human cancers bearing altered HGF/Met signalling in mouse models has been the fact that mouse HGF shows low affinity for human Met and therefore do not provide an ideal environment for such human tumours to grow. The transgenic mouse expressing human HGF, hHGFtg-SCID (Van Andel Institute), provides a species-compatible HGF (human) for the tumour environment (Zhang et al, 2005).

The NSCLC cell line H596 engages both EGFR and HGF signalling pathways, but is not HGF autocrine. To evaluate the in vivo efficacy of treatment with the FI/FS1-60 and FI/FS1-65 mAb$^2$ in the H596 model, NSCLC cells were grafted to the transgenic hHGFtg-SCID mice to provide the HGF stimulating environment. All hHGFtg-SCID female mice were implanted with 1×10$^6$ cells in the right flank. When tumours reached approximately 100 mm$^3$, animals were randomised into six groups, each having eight animals. Tumours were measured twice weekly and tumour volumes were calculated using the formula: (length×width)/depth. From Day 0, six groups of implanted mice were dosed intraperitoneally twice weekly for up to seven weeks with the following treatments: PBS vehicle (24 ml/kg), FS1-65, FI, FI+FS1-65, FI/FS1-60 and FI/FS1-65, all at a dose of 60 mg/kg. Animals were euthanised if their tumour exceeded a volume of 2500 mm$^3$.

All treatments showed tumour remission compared to the vehicle. The combination treatment of FI+FS1-65 did not show improvement in overall survival compared to FS1-65 or FI monotherapies. FI/FS1-60 mAb$^2$ treatment was superior in improving overall survival compared to other treatments. The logrank (Mantel-Cox) and Gehan-Breslow-Wilcoxon tests were used to determine the significance of the difference between the overall survival experiences (survival curves) of two groups. The results are summarized in FIG. 15. The mean tumour volumes of each group over time are shown in FIG. 11B. Two out of eight animals in the FI/FS1-65 mAb$^2$ treatment group showed complete tumour remission. The survival of the mice in each group over time is shown in FIG. 11C. Mice treated with the two mAb$^2$ had higher survival rates compared to those treated with the combination of FI+FS1-65. In the group of mice treated with FI/FS1-60, all mice survived at the end of the study.

In conclusion, FI/FS1-60 and FI/FS1-65 mAb$^2$ were superior to monotherapies targeting either EGFR or HGF in inhibiting tumour growth. FI/FS1-60 was also superior to the combination treatment of FI+FS1-60 targeting EGFR and HGF.

Example 18—Reduced Skin Toxicity in Mice Treated with Anti-EGFR-Containing mAb$^2$ Skin toxicity has been observed with known anti-EGFR therapies, resulting in skin rash, lesions etc. In order to determine the toxicity of anti-EGFR Fcabs and mAb$^2$ containing anti-EGFR Fcs, an in vivo study was conducted. Anti-EGFR/CTLA4 mAb$^2$ 9D9/FS1-67 and controls (Example 11) were tested for their efficacy in controlling tumour growth in the syngeneic mouse tumour model LL2.ova as described in Kraman M, et al. (2010). The tumour cells ($5 \times 10^5$ cells) were implanted subcutaneously in the flank of female C57B16 (Charles River) mice aged 6-8 weeks and the mice were randomly assigned to four cohorts of eight mice each. On days 3, 6 and 10 after tumour implantation, the mice were injected intraperitoneally with 250 μg of the following treatments (10 mg/kg assuming 25 g/mouse): mouse IgG2a control, FS1-67 Fcab, anti-CTLA-4 9D9m2a and 9D9/FS1-67 mAb$^2$. The tumour volumes were measured with electronic callipers at days 10, 12, 14, 17, 19, 20 and 21. At day 16 pictures of the mice were taken to illustrate the observed skin toxicity.

Figure 12:
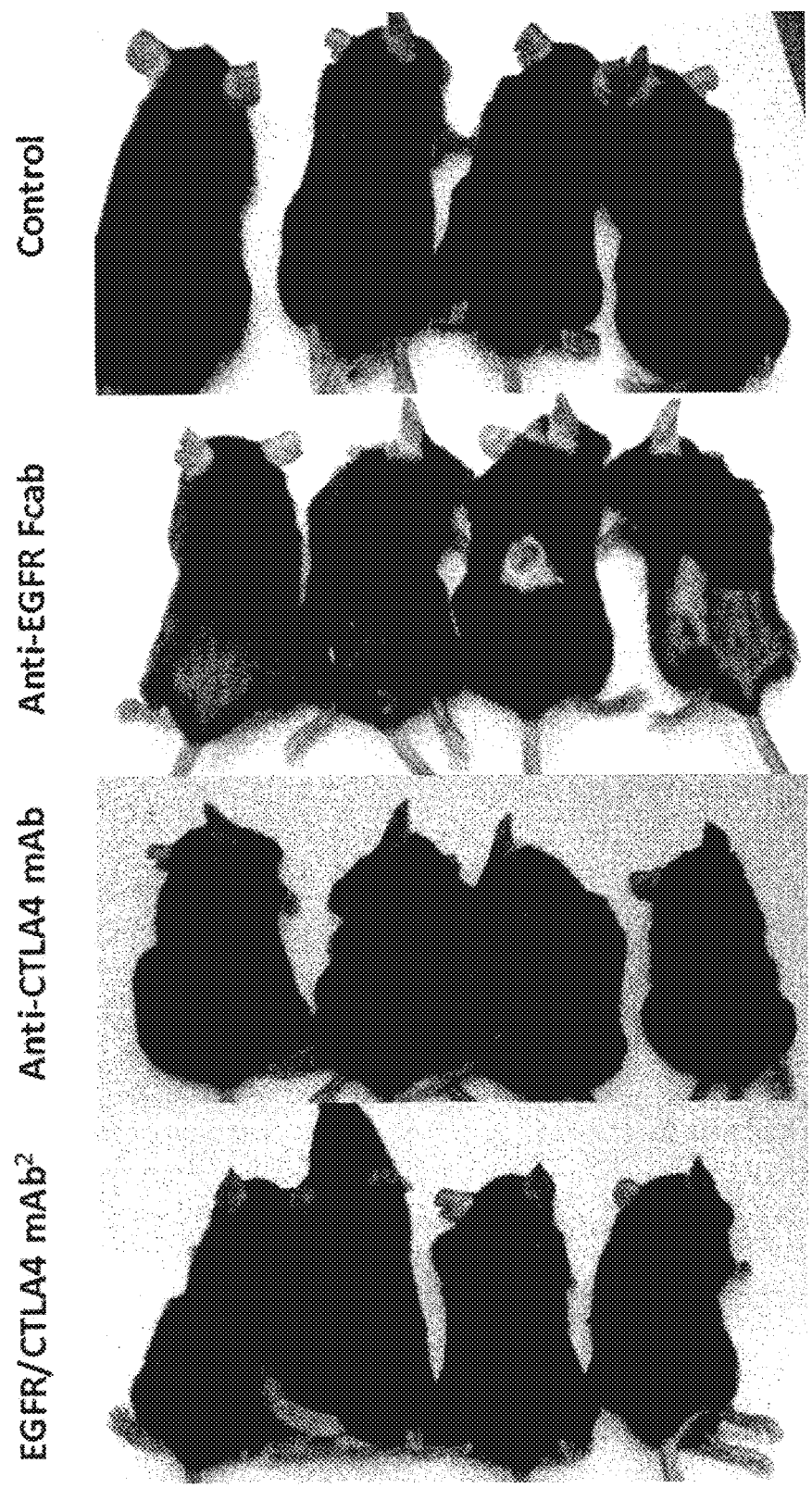
FIG. 12 shows the skin toxicity of anti-EGFR therapy in an in vivo study. Photographs of representative mice from each group taken at day 16 after tumour implantation are shown. Mice were treated with, a mouse IgG2a control (control), FS1-67 Fcab (anti-EGFR Fcab), anti-CTLA-4 9D9m2a (anti-CTLA4 mAb) or 9D9-FS1-67 mAb² (EGFR/CTLA4 mAb²). Mice treated with FS1-67 alone developed substantial hair loss and skin lesions as compared to untreated mice, anti-CTLA4 mAb treated mice or mice treated with anti-EGFR/CTLA4 mAb². Bispecificity of the mAb² resulted in reduced skin toxicity compared to the Fcab treatment alone.

The skin toxicity observed was most pronounced in mice treated with FS1-67 monotherapy. There was considerable hair loss in four of the mice and two of them showed lesions although not at the site of tumour implantation. Two of the mice treated with 9D9/FS1-67 mAb$^2$ also showed some hair loss, but not as apparent as the mice treated with FS1-67 monotherapy. The results are shown in FIG. 12. Table 13 summarises the observed skin toxicity in this trial. Without wishing to be limited by theory, it is thought that the high levels of CTLA4 expression in tumour infiltrating Tregs may be concentrating the mAb$^2$ at the tumour and limiting the effect of the EGFR Fcab on the skin, thus explaining the reduced skin toxicity observed with the mAb$^2$. The 9D9/FS1-67 mAb$^2$ also showed the highest level of control of tumour growth.

TABLE 13

In vivo study skin toxicity summary

| Group | Antibody | Mice showing hair loss | Extent of hair loss | Skin lesions |
|---|---|---|---|---|
| 1 | FS1-67 | 4/8 | +++ | 2/8 |
| 2 | 9D9m2a | 0/8 | − | 0/8 |
| 3 | 9D9/FS1-67 | 2/8 | + | 0/8 |
| 4 | Ctrl | 0/8 | − | 0/8 |

The reduced skin toxicity with the anti-EGFR-based mAb$^2$ was also observed in the in vivo efficacy study of H596. Mice in the FS1-65 group and the FI+FS1-65 combination group showed hair loss. However, in the FI/FS1-60 and FI/FS1-65 mAb$^2$ treatment groups the hair loss was noticeably reduced. The observation is consistent with the theory that the second target in the mAb$^2$ directs the bispecific molecules to sites with high expression level of the second target, limiting the effect of anti-EGFR domain on skin. Both in vivo studies conducted thus showed that anti-EGFR-based mAb$^2$ led to reduced skin toxicity.

Example 19—Biophysical Characterisation of Anti-EGFR-Based mAb$^2$ by Size Exclusion Chromatography The mAb$^2$ RI/FS1-60, RI/FS1-65, FI/FS1-60 and FI/FS1-65 were prepared by replacing the CH3 domains of the monoclonal antibodies RI and FI with the CH3 domains of the anti-EGFR Fcabs. To assess the effects of this CH3 domain swap, biophysical characterisation of the anti-EGFR-based mAb$^2$ was performed. mAb$^2$ and mAb samples were analysed by size-exclusion high performance liquid chromatography (SE-HPLC) on an Agilent 1200 series HPLC system, using a Zorbex GF-250 9.4 mm ID×25 cm column (Agilent). 80 μl aliquots of 1 mg/ml samples were injected and run in 50 mM sodium phosphate, 150 mM sodium chloride, 500 mM I-arginine, pH 6.0 at 1 ml/min for 15 minutes. Soluble aggregate levels were analysed using Chemstation software (Agilent). The mAb$^2$ exhibited symmetrical single peak SE-HPLC profiles, with a column retention time similar to that of the corresponding parental mAb (Table 14). These results demonstrated that the CH3 domain swap had minimal effect on the parental mAb structures, and that these mAb$^2$ are monomeric and do not form soluble aggregates.

TABLE 14

Biophysical characterisation by SE-HPLC

| mAb$^2$ or mAb | SE-HPLC (monomer %) | Retention time (minutes) |
|---|---|---|
| RI/FS1-60 | 100 | 9.442 |
| RI/FS1-65 | 100 | 9.963 |
| RI | 100 | 9.357 |
| FI/FS1-60 | 99.3 | 8.720 |
| FI/FS1-65 | 98.0 | 8.924 |
| FI | 99.4 | 8.551 |

Example 20—Binding of Anti-EGFR mAb$^2$ to EGFR

Anti-EGFR mAb$^2$ and Fcab were tested for binding to cell surface EGFR on cell lines NCI-H1975 (see Example 15 for details) and HCC827 (ATCC CRL-2868, a lung adenocarcinoma that has an acquired deletion [E746-A750] in the EGFR tyrosine kinase domain) by flow cytometry. The binding of RI/FS1-65, FI/FS1-65 and FS1-65 Fcab was assessed by incubating the cell lines with mAb$^2$ or Fcab in flow buffer for 1 hour on ice. Wild type (WT) Fcab and IgG were used as controls. Cells were washed and mAb$^2$ or Fcab binding was detected with an R-Phycoerythrin-conjugated anti-human IgG secondary antibody (Jackson, #109-116-098) and incubated on ice in the dark for 45 minutes. Excess secondary antibody was washed off and the signals were analysed by flow cytometry using a Flow Cytometer (FACSCanto™ II, BD Biosciences). Geometric mean fluorescence signal was plotted against the mAb² or Fcab concentration to determine the $EC_{50}$ (Table 15). All anti-EGFR mAb² and the Fcab bound to NCI-H1975 and HCC827 cell lines in a concentration dependent manner, whereas the WT Fcab and IgG did not, demonstrating the specificity of these mAb² and Fcab for EGFR.

TABLE 15

Binding affinity of anti-EGFR mAb² or Fcab to NCI-H1975 and HCC827 cell lines by flow cytometry

| Fcab | NCI-H1975 cell binding ($EC_{50}$ [nM]) | HCC827 cell binding ($EC_{50}$ [nM]) |
|---|---|---|
| RI/FS1-65 | 2.161 | 3.555 |
| FI/FS1-65 | 1.988 | 4.078 |
| FS1-65 | 1.265 | 1.960 |

The binding affinities of anti-EGFR mAb² to His-tagged human EGFR (Sino Biological) were determined using SPR. For affinity measurements, a BIAcore™ T200 instrument (GE healthcare) and a CM5 chip coated with 6120-8520 RU of anti-human Fab antibody (GE healthcare, 28-9583-25) were used. Anti-EGFR mAb² (5 µg/ml) were injected in HBS-EP+buffer (GE Healthcare) at 10 µl/min for 5 min to be captured on the anti-Fab coated CM5 chip. Concentration ranges of human EGFR (0.27-139 nM) were injected at 30 µl/min for 10 min to measure the on-rate. HBS-EP+buffer was then injected for 10 min to determine the dissociation rate. Reference subtraction was performed by injection of the EGFR antigen to a flow cell without the mAb² capture step. The anti-Fab surface was regenerated using 10 mM glycine at 30 µl/min for 60 seconds two times. The binding affinity ($K_D$) was derived from 1:1 (Langmuir) fitting model using the BIAcore™ T200 Evaluation Software Version 3.0 (GE Healthcare). The results showed that the anti-EGFR-based mAb² bind to human EGFR with affinities between 1.6-3.6 nM (see Table 16).

TABLE 16

Binding affinity ($K_D$) of anti-EGFR mAb² to human EGFR

| mAb² | Human EGFR $K_D$ (nM) |
|---|---|
| RI/FS1-60 | 3.6 |
| FI/FS1-60 | 3.5 |
| 4420/FS1-60 | 4.5 |
| RI/FS1-65 | 1.8 |
| FI/FS1-65 | 1.6 |
| 4420/FS1-65 | 2.0 |
| 4420/FS1-67 | 2.5 |

Example 21—In Vivo Efficacy Studies: Anti-EGFR mAb² Treatment of the EGFR-Driven Human Patient-Derived Lung Adenocarcinoma Xenograft Model LXFA 677

The in vivo efficacy of EGFR-targeting mock mAb² was evaluated using mice bearing human patient derived xenograft (PDX) tumours. The same method as described in Example 10 was used.

Groups of seven mice were treated with the following: mock mAb² 4420/FS1-60, 4420/FS1-65, 4420/FS1-67, cetuximab, control 4420 mAb, or PBS as a vehicle control. mAb² or control mAb samples were dosed at 20 mg/kg and the vehicle was dosed at 10 ml/kg. Seven doses of the treatments were administered intravenously over two weeks. Tumour volumes were monitored twice weekly until day 88.

Figure 13:
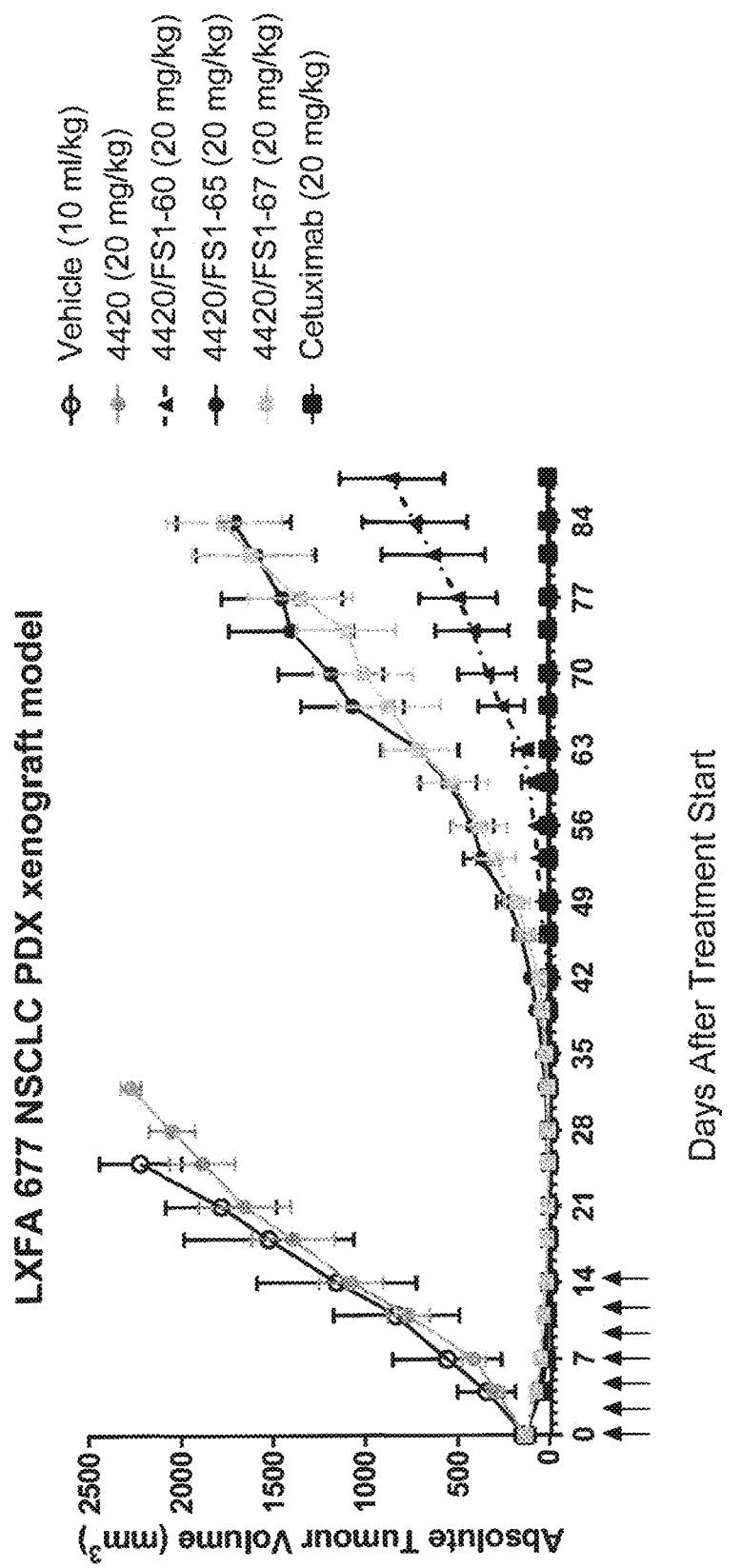
FIG. 13 shows the anti-tumour efficacy of anti-EGFR mAb² 4420/FS1-60, 4420/FS1-65 and 4420/FS1-67, cetuximab and 4420 control in mice bearing LXFA677 PDX tumours. Mice were dosed on days 0, 2, 4, 7, 9, 11 and 14, as indicated by arrows. The mean absolute tumour volumes over time in mice subjected to each treatment are shown. Tumour measurements were taken twice a week. All animals treated with anti-EGFR mAb² and cetuximab showed complete tumour regression in the course of study although relapse was observed in the mAb² groups.

Treatment with anti-EGFR mock mAb² 4420/FS1-60, 4420/FS1-65 and 4420/FS1-67 led to overall complete tumour remission, but individual tumours in all three groups underwent merely partial remission. The 4420 control mAb did not display any anti-tumour efficacy (FIG. 13). One to five weeks after the last dose, tumour regrowth was observed in all animals treated with the anti-EGFR mAb², except one mouse dosed with 4420/FS1-65. A statistically significant delay in tumour growth to 400% was observed for all mAb² relative to the vehicle control group as well as the 4420 control group (Kaplan-Meier) (Table 17). In conclusion, at well-tolerated dose levels all three mAb² led to complete remission of the EGFR-dependent PDX model LXFA 677.

It is known that the three mAb² tested are crossreactive with mouse EGFR and therefore could lead to a sink effect compared with the human EGFR specific cetuximab. Further dosing of the anti-EGFR mAb² to compensate for the sink effect is hypothesized to lead to continuous tumour remission. Alternatively, a loading dose prior to the start of treatment could also circumvent this effect.

TABLE 17

Statistical comparison of mAb² efficacy in LXFA677 in vivo study Delay in tumour growth - Kaplan-Meier

| | Significance relative to | | |
|---|---|---|---|
| | 4420/FS1-60 (20 mg/ml) | 4420/FS1-65 (20 mg/ml) | 4420/FS1-67 (20 mg/ml) |
| Vehicle control | P = 0.0003 | P = 0.0003 | P = 0.0003 |
| 4420 control | P = 0.0002 | P = 0.0002 | P = 0.0002 |

Sequence listing

Amino acid sequences of the Fcab FS1-60 CH3 domain structural loops

FS1-60 AB (SEQ ID NO: 1)

loop-LDEGGP

FS1-60 CD (SEQ ID NO: 2)

loop-TYG

FS1-60 EF (SEQ ID NO: 3)

loop-SHWRWYS

Amino acid sequence of the Fcab FS1-60 CH3 domain (SEQ ID NO: 4)

| Sequence listing |
|---|

GQPREPQVYTLPPSRDE<u>LDEGGP</u>VSLTCLVKGFYPSDIAVEWES<u>TYGP</u>

ENNYKTTPPVLDSDGSFFLYS<u>RLTV</u><u>SHWRWYS</u>GNVFSCSVMHEALHNH

YTQKSLSLSPG

Amino acid sequence of the Fcab FS1-60 CH3 domain comprising a C-terminal lysine
(SEQ ID NO: 4)
GQPREPQVYTLPPSRDE<u>LDEGGP</u>VSLTCLVKGFYPSDIAVEWES<u>TYGP</u>

ENNYKTTPPVLDSDGSFFLYS<u>RLTV</u><u>SHWRWYS</u>GNVFSCSVMHEALHNH

YTQKSLSLSPGK (SEQ ID NO: 68)

Nucleotide sequence encoding the Fcab FS1-60 CH3 domain
(SEQ ID NO: 5)
GGCCAGCCTCGAGAACCACAGGTGTACACCCTGCCCCCATCCCGGGAT

GAGTTGGATGAGGGGGGTCCTGTCAGCCTGACCTGCCTGGTCAAAGGC

TTCTATCCCAGCGACATCGCCGTGGAGTGGGAGAGCACTTATGGGCCG

GAGAACAACTACAAGACCACGCCTCCCGTGCTGGACTCCGACGGCTCC

TTCTTCCTCTACAGCAGGCTCACCGTGTCTCATTGGAGGTGGTACTCT

GGGAACGTCTTCTCATGCTCCGTGATGCATGAGGCTCTGCACAACCAC

TACACACAGAAGAGCCTCTCCCTGTCTCCGGGT

Amino acid sequence of the CH2 and CH3 domains of Fcab FS1-60
(SEQ ID NO: 6)
APELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNK

ALPAPIEKTISKAKGQPREPQVYTLPPSRDELDEGGPVSLTCLVKGFY

PSDIAVEWESTYGPENNYKTTPPVLDSDGSFFLYSRLTVSHWRWYSGN

VFSCSVMHEALHNHYTQKSLSLSPG

Nucleotide sequence encoding the CH2 and CH3 domains of Fcab FS1-60
(SEQ ID NO: 7)
GCCCCCGAGCTGCTGGGAGGCCCTTCCGTGTTTCTGTTCCCCCCAAAG

CCCAAGGACACCCTGATGATCTCCCGGACCCCCGAAGTGACCTGCGTG

GTGGTGGATGTGTCCCACGAGGACCCTGAAGTGAAGTTCAATTGGTAC

GTGGACGGCGTGGAAGTGCACAACGCCAAGACCAAGCCCAGAGAGGAA

CAGTACAACTCCACCTACCGGGTGGTGTCCGTGCTGACCGTGCTGCAC

CAGGATTGGCTGAACGGCAAAGAGTACAAGTGCAAGGTGTCCAACAAG

GCCCTGCCTGCCCCCATCGAAAAGACCATCTCCAAGGCCAAGGGCCAG

CCCCGGGAACCCCAGGTGTACACACTGCCCCCTAGCAGGGACGAGCTG

GATGAAGGCGGACCTGTGTCCCTGACCTGTCTCGTGAAGGGCTTCTAC

CCCTCCGATATCGCCGTGGAATGGGAGTCCACCTACGGCCCCGAGAAC

AACTACAAGACCACCCCCCCTGTGCTGGACTCCGACGGCTCCTTCTTT

CTGTACTCCCGCCTGACCGTGTCCCACTGGCGGTGGTACTCTGGCAAC

GTGTTCTCCTGCAGCGTGATGCACGAGGCCCTGCACAACCACTACACC

CAGAAGTCCCTGTCCCTGAGCCCCGGC

Amino acid sequences of the Fcab FS1-65 CH3 domain structural loops
FS1-65 AB
(SEQ ID NO: 1)
loop-LDEGGP

| Sequence listing | |
|---|---|
| FS1-65 CD loop-TYG | (SEQ ID NO: 2) |
| FS1-65 EF loop-SYWRWVK | (SEQ ID NO: 8) |
| Amino acid sequence of the Fcab FS1-65 CH3 domain<br>GQPREPQVYTLPPSRDE<u>LDEGGP</u>VSLTCLVKGFYPSDIAVEWES<u>TYGP</u><br>ENNYKTTPPVLDSDGSFFLYSKLTV<u>SYWRWVK</u>GNVFSCSVMHEALHNH<br>YTQKSLSLSPG | (SEQ ID NO: 9) |
| Nucleotide sequence encoding the Fcab FS1-65 CH3 domain<br>GGCCAGCCTCGAGAACCACAGGTGTACACCCTGCCCCCATCCCGGGAT<br>GAGTTGGATGAGGGGGGTCCTGTCAGCCTGACCTGCCTGGTCAAAGGC<br>TTCTATCCCAGCGACATCGCCGTGGAGTGGGAGAGCACTTATGGGCCG<br>GAGAACAACTACAAGACCACGCCTCCCGTGCTGGACTCCGACGGCTCC<br>TTCTTCCTCTACAGCAAGCTCACCGTGTCTTACTGGAGGTGGGTTAAA<br>GGGAACGTCTTCTCATGCTCCGTGATGCATGAGGCTCTGCACAACCAC<br>TACACACAGAAGAGCCTCTCCCTGTCTCCGGGT | (SEQ ID NO: 10) |
| Amino acid sequence of the CH2 and CH3 domains of Fcab FS1-65<br>APELLGGPSVFLFPPKPKDTLMISRTPEVTCVVVDVSHEDPEVKFNWY<br>VDGVEVHNAKTKPREEQYNSTYRVVSVLTVLHQDWLNGKEYKCKVSNK<br>ALPAPIEKTISKAKGQPREPQVYTLPPSRDE<u>LDEGGP</u>VSLTCLVKGFY<br>PSDIAVEWES<u>TYG</u>PENNYKTTPPVLDSDGSFFLYSKLTV<u>SYWRWVK</u>GN<br>VFSCSVMHEALHNHYTQKSLSLSPG | (SEQ ID NO: 11) |
| Nucleotide sequence encoding the CH2 and CH3 domains of Fcab FS1-65<br>GCCCCCGAGCTGCTGGGAGGCCCTTCCGTGTTTCTGTTCCCCCCAAAG<br>CCCAAGGACACCCTGATGATCTCCCGGACCCCCGAAGTGACCTGCGTG<br>GTGGTGGATGTGTCCCACGAGGACCCTGAAGTGAAGTTCAATTGGTAC<br>GTGGACGGCGTGGAAGTGCACAACGCCAAGACCAAGCCCAGAGAGGAA<br>CAGTACAACTCCACCTACCGGGTGGTGTCCGTGCTGACCGTGCTGCAC<br>CAGGATTGGCTGAACGGCAAAGAGTACAAGTGCAAGGTGTCCAACAAG<br>GCCCTGCCTGCCCCCATCGAAAAGACCATCTCCAAGGCCAAGGGCCAG<br>CCTCGAGAACCACAGGTGTACACCCTGCCCCCATCCCGGGATGAGTTG<br>GATGAGGGGGGTCCTGTCAGCCTGACCTGCCTGGTCAAAGGCTTCTAT<br>CCCAGCGACATCGCCGTGGAGTGGGAGAGCACTTATGGGCCGGAGAAC<br>AACTACAAGACCACGCCTCCCGTGCTGGACTCCGACGGCTCCTTCTTC<br>CTCTACAGCAAGCTCACCGTGTCTTACTGGAGGTGGGTTAAAGGGAAC<br>GTCTTCTCATGCTCCGTGATGCATGAGGCTCTGCACAACCACTACACA<br>CAGAAGAGCCTCTCCCTGTCTCCGGGT | (SEQ ID NO: 12) |
| Amino acid sequences of the Fcab FS1-67 CH3 structural loops<br>FS1-67 AB | |

-continued

Sequence listing loop-TDDGP (SEQ ID NO: 13)

FS1-67 CD
loop-TYG (SEQ ID NO: 2)

FS1-67 EF
loop-SYWRWYK (SEQ ID NO: 14)

Amino acid sequence of Fcab FS1-67 CH3 domain
(SEQ ID NO: 15)
GQPREPQVYTLPPSRDETDDGPVSLTCLVKGFYPSDIAVEWESTYGPE

NNYKTTPPVLDSDGSFFLYSKLTVSYWRWYKGNVFSCSVMHEALHNHY

TQKSLSLSPG

Nucleotide sequence encoding the Fcab FS1-67 CH3 domain
(SEQ ID NO: 16)
GGCCAGCCTCGAGAACCACAGGTGTACACCCTGCCCCCATCCCGGGAT

GAGACTGACGACGGTCCGGTCAGCCTGACCTGCCTGGTCAAAGGCTTC

TATCCCAGCGACATCGCCGTGGAGTGGGAGAGCACTTATGGGCCGGAG

AACAACTACAAGACCACGCCTCCCGTGCTGGACTCCGACGGATCCTTC

TTCCTCTACAGCAAGCTCACCGTGTCTTACTGGAGGTGGTACAAAGGG

AACGTCTTCTCATGCTCCGTGATGCATGAGGCTCTGCACAACCACTAC

ACACAGAAGAGCCTCTCCCTGTCTCCGGGT

Amino acid sequence of the CH2 and CH3 domains of Fcab FS1-67
(SEQ ID NO: 17)
APELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNK

ALPAPIEKTISKAKGQPREPQVYTLPPSRDETDDGPVSLTCLVKGFYP

SDIAVEWESTYGPENNYKTTPPVLDSDGSFFLYSKLTVSYWRWYKGNV

FSCSVMHEALHNHYTQKSLSLSPG

Nucleotide sequence encoding the CH2 and CH3 domains of Fcab FS1-67
(SEQ ID NO: 18)
GCCCCCGAGCTGCTGGGAGGCCCTTCCGTGTTTCTGTTCCCCCCAAAG

CCCAAGGACACCCTGATGATCTCCCGGACCCCCGAAGTGACCTGCGTG

GTGGTGGATGTGTCCCACGAGGACCCTGAAGTGAAGTTCAATTGGTAC

GTGGACGGCGTGGAAGTGCACAACGCCAAGACCAAGCCCAGAGAGGAA

CAGTACAACTCCACCTACCGGGTGGTGTCCGTGCTGACCGTGCTGCAC

CAGGATTGGCTGAACGGCAAAGAGTACAAGTGCAAGGTGTCCAACAAG

GCCCTGCCTGCCCCCATCGAAAAGACCATCTCCAAGGCCAAGGGCCAG

CCTCGAGAACCACAGGTGTACACCCTGCCCCCATCCCGGGATGAGACT

GACGACGGTCCGGTCAGCCTGACCTGCCTGGTCAAAGGCTTCTATCCC

AGCGACATCGCCGTGGAGTGGGAGAGCACTTATGGGCCGGAGAACAAC

TACAAGACCACGCCTCCCGTGCTGGACTCCGACGGATCCTTCTTCCTC

TACAGCAAGCTCACCGTGTCTTACTGGAGGTGGTACAAAGGGAACGTC

TTCTCATGCTCCGTGATGCATGAGGCTCTGCACAACCACTACACACAG

AAGAGCCTCTCCCTGTCTCCGGGT

| Sequence listing |
| --- |

Amino acid sequence of the Fcab FS1-60, Fcab FS1-65, and
Fcab FS1-67 CH2 domain (SEQ ID NO: 19)

APELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNK

ALPAPIEKTISKAK

Nucleotide sequence encoding the Fcab FS1-60, Fcab FS1-65, and
Fcab FS1-67 CH2 domain (SEQ ID NO: 20)

GCCCCCGAGCTGCTGGGAGGCCCTTCCGTGTTTCTGTTCCCCCCAAAG

CCCAAGGACACCCTGATGATCTCCCGGACCCCCGAAGTGACCTGCGTG

GTGGTGGATGTGTCCCACGAGGACCCTGAAGTGAAGTTCAATTGGTAC

GTGGACGGCGTGGAAGTGCACAACGCCAAGACCAAGCCCAGAGAGGAA

CAGTACAACTCCACCTACCGGGTGGTGTCCGTGCTGACCGTGCTGCAC

CAGGATTGGCTGAACGGCAAAGAGTACAAGTGCAAGGTGTCCAACAAG

GCCCTGCCTGCCCCCATCGAAAAGACCATCTCCAAGGCCAAG

Amino acid sequences of rilotumumab (RI) CDRs
RI CDR1

(SEQ ID NO: 21)

VH-IYYWS

RI CDR2

(SEQ ID NO: 22)

VH-YVYYSGSTNYNPSLKS

RI CDR3

(SEQ ID NO: 23)

VH-GGYDFWSGYFDY

RI CDR1

(SEQ ID NO: 24)

VL-RASQSVDSNLA

RI CDR2

(SEQ ID NO: 25)

VL-GASTRAT

RI CDR3

(SEQ ID NO: 26)

VL-QQYINWPPIT

Amino acid sequence of the rilotumumab (RI) heavy chain

Italics = Rilotumumab VH (CDRs are underlined);
bold = human IgG2 CH1; bold and underlined = human IgG2 hinge;
bold and italics = human IgG2 CH2;
bold, italics and underlined = human IgG2 CH3

(SEQ ID NO: 27)

*QVQLQESGPGLVKPSETLSLTCTVSGGSIS<u>IYYWS</u>WIRQPPGKGLEWIG<u>YVYYSGSTNYNPSLKS</u>RV*

*TISVDTSKNQFSLKLNSVTAADTAVYYCAR<u>GGYDFWSGYFDY</u>WGQGTLVTVSS*__ASTKGPSVFPLAP__

__CSRSTSESTAALGCLVKDYFPEPVTVSWNSGALTSGVHTFPAVLQSSGLYSLSSVVTVPSSNFGTQ__

__TYTCNVDHKPSNTKVDKTV<u>ERKCCVECPPCP</u>__*__APPVAGPSVFLFPPKPKDTLMISRTPEVTCVVVDV__*

*__SHEDPEVQFNWYVDGVEVHNAKTKPREEQFNSTFRVVSVLTVVHQDWLNGKEYKCKVSNKGLPA__*

*__PIEKTISKTK__<u>GQPREPQVYTLPPSREEMTKNQVSLTCLVKGFYPSDIACEWESNGQPENNYKTTPPM__</u>*

*<u>__LDSDGSFFLYSKLTVDKSRWQQGNVFSCSVMHEALHNHYTQKSLSLSPG__</u>*

Amino acid sequence of the rilotumumab (RI) and RI/FS1-60,
RI/FS1-65, and RI/FS1-67 light chain
Italics = Rilotumumab VL (CDRs are underlined);
bold = human IgG kappa constant region (SEQ ID NO: 28)

```
                          Sequence listing
```

*EIVMTQSPATLSVSPGERATLSC<u>RASQSVDSNLA</u>WYRQKPGQAPRLLI*

*Y<u>GASTRATGI</u>PARFSGSGSGTEFTLTISSLQSEDFAVYYC<u>QQYINWPP</u>*

*<u>IT</u>FGQGTRLEIKR*TVAAPSVFIFPPSDEQLKSGTASVVCLLNNFYPRE

AKVQWKVDNALQSGNSQESVTEQDSKDSTYSLSSTLTLSKADYEKHKV

YACEVTHQGLSSPVTKSFNRGEC

Amino acid sequence of the rilotumumab (RI) VH domain
(SEQ ID NO: 29)

QVQLQESGPGLVKPSETLSLTCTVSGGSIS<u>IYYWS</u>WIRQPPGKGLEWI

G<u>VYYSGSTNYNPSLKS</u>RVTISVDTSKNQFSLKLNSVTAADTAVYYCA

R<u>GGYDFWSGYFDY</u>WGQGTLVTVSS

Amino acid sequence of the rilotumumab (RI) VL domain
(SEQ ID NO: 30)

EIVMTQSPATLSVSPGERATLSC<u>RASQSVDSNLA</u>WYRQKPGQAPRLLI

Y<u>GASTRATGI</u>PARFSGSGSGTEFTLTISSLQSEDFAVYYC<u>QQYINWPP</u>

<u>IT</u>FGQGTRLEIKR

Amino acid sequences of ficlatuzumab (FI) CDR's
FI CDR1
(SEQ ID NO: 31)
VH-TYWMH

FI CDR2
(SEQ ID NO: 32)
VH-EINPTNGHTNYNQKFQG

FI CDR3
(SEQ ID NO: 33)
VH-NYVGSIFDY

FI CDR1
(SEQ ID NO: 34)
VL-KASENVVSYVS

FI CDR2
(SEQ ID NO: 35)
VL-GASNRES

FI CDR3
(SEQ ID NO: 36)
VL-GQSYNYPYT

Amino acid sequence of the ficlatuzumab (FI) heavy chain
Italics = Ficlatuzumab VH (CDRs are underlined);
bold = human IgG1 CH1;
bold and underlined = human IgG1 hinge;
bold and italics = human IgG1 CH2;
bold, italics and underlined = human IgG1 CH3
(SEQ ID NO: 37)

*QVQLVQPGAEVKKPGTSVKLSCKASGYTFT<u>TYWMH</u>WVRQAPGQGLEWIG<u>EINPTNGHTNYNQKFQG</u>*

*RATLTVDKSTSTAYMELSSLRSEDTAVYYCAR<u>NYVGSIFDY</u>WGQGTLLTVSS*ASTKGPSVFPLAPS

SKSTSGGTAALGCLVKDYFPEPVTVSWNSGALTSGVHTFPAVLQSSGLYSLSSVVTVPSSSLGTQT

YICNVNHKPSNTKVDKRV<u>EPKSCDKTHTCPPCP</u>*APELLGGPSVFLFPPKPKDTLMISRTPEVTCVVV*

*DVSHEDPEVKFNWYVDGVEVHNAKTKPREEQYNSTYRVVSVLTVLHQDWLNGKEYKCKVSNKAL*

*PAPIEKTISKAK<u>GQPREPQVYTLPPSREEMTKNQVSLTCLVKGFYPSDIAVEWESNGQPENNYKTTP</u>*

*<u>PVLDSDGSFFLYSKLTVDKSRWQQGNVFSCSVMHEALHNHYTQKSLSLSPG</u>*

Amino acid sequence of the ficlatuzumab (FI) and FI/FS1-60,
FI/FS1-65, and FI/FS1-67 light chain
Italics = Ficlatuzumab VL (CDRs are underlined);
bold = human IgG kappa constant region
(SEQ ID NO: 38)

| Sequence listing |
|---|
| *DIVMTQSPDSLAMSLGERVTLNCKASENVVSYVSWYQQKPGQSPKLLI* |
| *YGASNRESGVPDRFSGSGSATDFTLTISSVQAEDVADYHCGQSYNYPY* |
| *TFGQGTKLEIKR*TVAAPSVFIFPPSDEQLKSGTASVVCLLNNFYPREA |
| KVQWKVDNALQSGNSQESVTEQDSKDSTYSLSSTLTLSKADYEKHKVY |
| ACEVTHQGLSSPVTKSFNRGEC |

| Amino acid sequence of the ficlatuzumab (FI) VH domain | (SEQ ID NO: 39) |
|---|---|
| QVQLVQPGAEVKKPGTSVKLSCKASGYTFT<u>TYWMH</u>WVRQAPGQGLEWI | |
| G<u>EINPTNGHTNYNQKFQG</u>RATLTVDKSTSTAYMELSSLRSEDTAVYYC | |
| AR<u>NYVGSIFDY</u>WGQGTLLTVSS | |

| Amino acid sequence of the ficlatuzumab (FI) VL domain | (SEQ ID NO: 40) |
|---|---|
| DIVMTQSPDSLAMSLGERVTLNC<u>KASENVVSYVS</u>WYQQKPGQSPKLLI | |
| Y<u>GASNRES</u>GVPDRFSGSGSATDFTLTISSVQAEDVADYHC<u>GQSYNYPY</u> | |
| <u>T</u>FGQGTKLEIKR | |

| Amino acid sequence of the mAb$^2$RI/FS1-60 heavy chain | (SEQ ID NO: 41) |
|---|---|
| QVQLQESGPGLVKPSETLSLTCTVSGGSISIYYWSWIRQPPGKGLEWI | |
| GYVYYSGSTNYNPSLKSRVTISVDTSKNQFSLKLNSVTAADTAVYYCA | |
| RGGYDFWSGYFDYWGQGTLVTVSSASTKGPSVFPLAPCSRSTSESTAA | |
| LGCLVKDYFPEPVTVSWNSGALTSGVHTFPAVLQSSGLYSLSSVVTVP | |
| SSNFGTQTYTCNVDHKPSNTKVDKTVERKCCVECPPCPAPPVAGPSVF | |
| LFPPKPKDTLMISRTPEVTCVVVDVSHEDPEVQFNWYVDGVEVHNAKT | |
| KPREEQFNSTFRVVSVLTVVHQDWLNGKEYKCKVSNKGLPAPIEKTIS | |
| KTKGQPREPQVYTLPPSRDELDEGGPVSLTCLVKGFYPSDIAVEWEST | |
| YGPENNYKTTPPVLDSDGSFFLYSRLTVSHWRWYSGNVFSCSVMHEAL | |
| HNHYTQKSLSLSPG | |

| Amino acid sequence of the mAb$^2$FI/FS1-60 heavy chain | (SEQ ID NO: 42) |
|---|---|
| QVQLVQPGAEVKKPGTSVKLSCKASGYTFTTYWMHWVRQAPGQGLEWI | |
| GEINPTNGHTNYNQKFQGRATLTVDKSTSTAYMELSSLRSEDTAVYYC | |
| ARNYVGSIFDYWGQGTLLTVSSASTKGPSVFPLAPSSKSTSGGTAALG | |
| CLVKDYFPEPVTVSWNSGALTSGVHTFPAVLQSSGLYSLSSVVTVPSS | |
| SLGTQTYICNVNHKPSNTKVDKRVEPKSCDKTHTCPPCPAPELLGGPS | |
| VFLFPPKPKDTLMISRTPEVTCVVVDVSHEDPEVKFNWYVDGVEVHNA | |
| KTKPREEQYNSTYRVVSVLTVLHQDWLNGKEYKCKVSNKALPAPIEKT | |
| ISKAKGQPREPQVYTLPPSRDELDEGGPVSLTCLVKGFYPSDIAVEWE | |
| STYGPENNYKTTPPVLDSDGSFFLYSRLTVSHWRWYSGNVFSCSVMHE | |
| ALHNHYTQKSLSLSPG | |

| Amino acid sequence of the mAb$^2$RI/FS1-65 heavy chain | (SEQ ID NO: 43) |
|---|---|
| QVQLQESGPGLVKPSETLSLTCTVSGGSISIYYWSWIRQPPGKGLEWI | |
| GYVYYSGSTNYNPSLKSRVTISVDTSKNQFSLKLNSVTAADTAVYYCA | |
| RGGYDFWSGYFDYWGQGTLVTVSSASTKGPSVFPLAPCSRSTSESTAA | |

| Sequence listing |
|---|
| LGCLVKDYFPEPVTVSWNSGALTSGVHTFPAVLQSSGLYSLSSVVTVP |
| SSNFGTQTYTCNVDHKPSNTKVDKTVERKCCVECPPCPAPPVAGPSVF |
| LFPPKPKDTLMISRTPEVTCVVVDVSHEDPEVQFNWYVDGVEVHNAKT |
| KPREEQFNSTFRVVSVLTVVHQDWLNGKEYKCKVSNKGLPAPIEKTIS |
| KTKGQPREPQVYTLPPSRDELDEGGPVSLTCLVKGFYPSDIAVEWEST |
| YGPENNYKTTPPVLDSDGSFFLYSKLTVSYWRWVKGNVFSCSVMHEAL |
| HNHYTQKSLSLSPG |
| Amino acid sequence of the mAb²FI/FS1-65 heavy chain (SEQ ID NO: 44) |
| QVQLVQPGAEVKKPGTSVKLSCKASGYTFTTYWMHWVRQAPGQGLEWI |
| GEINPTNGHTNYNQKFQGRATLTVDKSTSTAYMELSSLRSEDTAVYYC |
| ARNYVGSIFDYWGQGTLLTVSSASTKGPSVFPLAPSSKSTSGGTAALG |
| CLVKDYFPEPVTVSWNSGALTSGVHTFPAVLQSSGLYSLSSVVTVPSS |
| SLGTQTYICNVNHKPSNTKVDKRVEPKSCDKTHTCPPCPAPELLGGPS |
| VFLFPPKPKDTLMISRTPEVTCVVVDVSHEDPEVKFNWYVDGVEVHNA |
| KTKPREEQYNSTYRVVSVLTVLHQDWLNGKEYKCKVSNKALPAPIEKT |
| ISKAKGQPREPQVYTLPPSRDELDEGGPVSLTCLVKGFYPSDIAVEWE |
| STYGPENNYKTTPPVLDSDGSFFLYSKLTVSYWRWVKGNVFSCSVMHE |
| ALHNHYTQKSLSLSPG |
| Amino acid sequence of the mAb²RI/FS1-67 heavy chain (SEQ ID NO: 45) |
| QVQLQESGPGLVKPSETLSLTCTVSGGSISIYYWSWIRQPPGKGLEWI |
| GYVYYSGSTNYNPSLKSRVTISVDTSKNQFSLKLNSVTAADTAVYYCA |
| RGGYDFWSGYFDYWGQGTLVTVSSASTKGPSVFPLAPCSRSTSESTAA |
| LGCLVKDYFPEPVTVSWNSGALTSGVHTFPAVLQSSGLYSLSSVVTVP |
| SSNFGTQTYTCNVDHKPSNTKVDKTVERKCCVECPPCPAPPVAGPSVF |
| LFPPKPKDTLMISRTPEVTCVVVDVSHEDPEVQFNWYVDGVEVHNAKT |
| KPREEQFNSTFRVVSVLTVVHQDWLNGKEYKCKVSNKGLPAPIEKTIS |
| KTKGQPREPQVYTLPPSRDETDDGPVSLTCLVKGFYPSDIAVEWESTY |
| GPENNYKTTPPVLDSDGSFFLYSKLTVSYWRWYKGNVFSCSVMHEALH |
| NHYTQKSLSLSPG |
| Amino acid sequence of the mAb²FI/FS1-67 heavy chain (SEQ ID NO: 46) |
| QVQLVQPGAEVKKPGTSVKLSCKASGYTFTTYWMHWVRQAPGQGLEWI |
| GEINPTNGHTNYNQKFQGRATLTVDKSTSTAYMELSSLRSEDTAVYYC |
| ARNYVGSIFDYWGQGTLLTVSSASTKGPSVFPLAPSSKSTSGGTAALG |
| CLVKDYFPEPVTVSWNSGALTSGVHTFPAVLQSSGLYSLSSVVTVPSS |
| SLGTQTYICNVNHKPSNTKVDKRVEPKSCDKTHTCPPCPAPELLGGPS |
| VFLFPPKPKDTLMISRTPEVTCVVVDVSHEDPEVKFNWYVDGVEVHNA |
| KTKPREEQYNSTYRVVSVLTVLHQDWLNGKEYKCKVSNKALPAPIEKT |
| ISKAKGQPREPQVYTLPPSRDETDDGPVSLTCLVKGFYPSDIAVEWES |

```
TYGPENNYKTTPPVLDSDGSFFLYSKLTVSYWRWYKGNVFSCSVMHEA

LHNHYTQKSLSLSPG
```

Amino acid sequence of the human IgG1 Fc fragment
(wildtype [WT] Fcab)
(SEQ ID NO: 47)
```
TCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCL

VKGFYPSDIAVEWESNGQPENNYKTTPPVLDSDGSFFLYSKLTVDKSR

WQQGNVFSCSVMHEALHNHYTQKSLSLSPG
```

Amino acid sequence of the human IgG1 hinge region
(SEQ ID NO: 48)
```
EPKSCDKTHTCPPCP
```

Amino acid sequence of the truncated human IgG1 hinge region
(SEQ ID NO: 49)
```
TCPPCP
```

Amino acid sequence of the 9D9 light chain
(SEQ ID NO: 50)
```
DIVMTQTTLSLPVSLGDQASISCRSSQSIVHSNGNTYLEWYLQKPGQS

PKLLIYKVSNRFSGVPDRFSGSGSGTDFTLKISRVEAEDLGVYYCFQG

SHVPYTFGGGTKLEIKRADAAPTVSIFPPSSEQLTSGGASVVCFLNNF

YPKDINVKWKIDGSERQNGVLNSWTDQDSKDSTYSMSSTLTLTKDEYE

RHNSYTCEATHKTSTSPIVKSFNRNEC
```

Nucleotide sequence encoding the 9D9 light chain
(SEQ ID NO: 51)
```
GACATCGTGATGACCCAGACCACCCTGAGCCTGCCCGTGAGCCTGGGC

GACCAGGCCAGCATCAGCTGCAGAAGCAGCCAGAGCATCGTGCACAGC

AACGGCAACACCTACCTGGAGTGGTACCTGCAGAAGCCCGGCCAGAGC

CCCAAGCTGCTGATCTACAAGGTGAGCAACAGATTCAGCGGCGTGCCC

GACAGATTCAGCGGCAGCGGCAGCGGCACCGACTTCACCCTGAAGATC

AGCAGAGTGGAGGCCGAGGACCTGGGCGTGTACTACTGCTTCCAGGGC

AGCCACGTGCCCTACACCTTCGGCGGCGGCACCAAGCTGGAGATCAAG

AGAGCCGACGCCGCCCCCACCGTGAGCATCTTCCCCCCCAGCAGCGAG

CAGCTGACCAGCGGCGGCGCCAGCGTGGTGTGCTTCCTGAACAACTTC

TACCCCAAGGACATCAACGTGAAGTGGAAGATCGACGGCAGCGAGAGA

CAGAACGGCGTGCTGAACAGCTGGACCGACCAGGACAGCAAGGACAGC

ACCTACAGCATGAGCAGCACCCTGACCCTGACCAAGGACGAGTACGAG

AGACACAACAGCTACACCTGCGAGGCCACCCACAAGACCAGCACCAGC

CCCATCGTGAAGAGCTTCAACAGAAACGAGTGC
```

Amino acid sequence of the 9D9m2a heavy chain
(SEQ ID NO: 52)
```
EIQLQQSGPVLVKPGASVKMSCKASGYTFTDYYMNWVKQSHGKSLEWI

GVINPYNGDTSYNQKFKGKATLTVDKSSSTAYMELNSLTSEDSAVYYC

ARYYGSWFAYWGQGTLITVSTAKTTAPSVYPLAPVCGDTTGSSVTLGC

LVKGYFPEPVTLTWNSGSLSSGVHTFPAVLQSDLYTLSSSVTVTSSTW
```

| Sequence listing |
|---|
| PSQSITCNVAHPASSTKVDKKIEPRGPTIKPCPPCKCPAPNLLGGPSV |
| FIFPPKIKDVLMISLSPIVTCVVVDVSEDDPDVQISWFVNNVEVHTAQ |
| TQTHREDYNSTLRVVSALPIQHQDWMSGKEFKCKVNNKDLPAPIERTI |
| SKPKGSVRAPQVYVLPPPEEEMTKKQVTLTCMVTDFMPEDIYVEWTNN |
| GKTELNYKNTEPVLDSDGSYFMYSKLRVEKKNWVERNSYSCSVVHEGL |
| HNHHTTKSFSRTPGK |

Nucleotide sequence encoding the 9D9m2a heavy chain (SEQ ID NO: 53)

GAGATCCAGCTGCAGCAGAGCGGCCCCGTGCTGGTGAAGCCCGGCGCC
AGCGTGAAGATGAGCTGCAAGGCCAGCGGCTACACCTTCACCGACTAC
TACATGAACTGGGTGAAGCAGAGCCACGGCAAGAGCCTGGAGTGGATC
GGCGTGATCAACCCCTACAACGGCGACACCAGCTACAACCAGAAGTTC
AAGGGCAAGGCCACCCTGACCGTGGACAAGAGCAGCAGCACCGCCTAC
ATGGAGCTGAACAGCCTGACCAGCGAGGACAGCGCCGTGTACTACTGC
GCCAGATACTACGGCAGCTGGTTCGCCTACTGGGGCCAGGGCACCCTG
ATCACCGTGAGCACCGCCAAGACCACCGCCCCCAGCGTGTACCCCCTG
GCCCCCGTGTGCGGCGACACCACCGGCAGCAGCGTGACCCTGGGCTGC
CTGGTGAAGGGCTACTTCCCCGAGCCCGTGACCCTGACCTGGAACAGC
GGCAGCCTGAGCAGCGGCGTGCACACCTTCCCCGCCGTGCTGCAGAGC
GACCTGTACACCCTGAGCAGCAGCGTGACCGTGACCAGCAGCACCTGG
CCCAGCCAGAGCATCACCTGCAACGTGGCCCACCCCGCCAGCAGCACC
AAGGTGGACAAGAAGATCGAGCCCAGAGGCCCCACCATCAAGCCCTGC
CCCCCCTGCAAGTGCCCCGCCCCCAACCTGCTGGGCGGCCCCAGCGTG
TTCATCTTCCCCCCCAAGATCAAGGACGTGCTGATGATCAGCCTGAGC
CCCATCGTGACCTGCGTGGTGGTGGACGTGAGCGAGGACGACCCCGAC
GTGCAGATCAGCTGGTTCGTGAACAACGTGGAGGTGCACACCGCCCAG
ACCCAGACCCACAGAGAGGACTACAACAGCACCCTGAGAGTGGTGAGC
GCCCTGCCCATCCAGCACCAGGACTGGATGAGCGGCAAGGAGTTCAAG
TGCAAGGTGAACAACAAGGACCTGCCCGCCCCCATCGAGAGAACCATC
AGCAAGCCCAAGGGCAGCGTGAGAGCCCCCCAGGTGTACGTGCTGCCC
CCCCCCGAGGAGGAGATGACCAAGAAGCAGGTGACCCTGACCTGCATG
GTGACCGACTTCATGCCCGAGGACATCTACGTGGAGTGGACCAACAAC
GGCAAGACCGAGCTGAACTACAAGAACACCGAGCCCGTGCTGGACAGC
GACGGCAGCTACTTCATGTACAGCAAGCTGAGAGTGGAGAAGAAGAAC
TGGGTGGAGAGAAACAGCTACAGCTGCAGCGTGGTGCACGAGGGCCTG
CACAACCACCACACCACCAAGAGCTTCAGCAGAACCCCCGGCAAG

Amino acid sequence of the 9D9h1 heavy chain (SEQ ID NO: 54)

EIQLQQSGPVLVKPGASVKMSCKASGYTFTDYYMNWVKQSHGKSLEWI
GVINPYNGDTSYNQKFKGKATLTVDKSSSTAYMELNSLTSEDSAVYYC
ARYYGSWFAYWGQGTLITVSTAKTTAPSVYPLAPVCGDTTGSSVTLGC

LVKGYFPEPVTLTWNSGSLSSGVHTFPAVLQSDLYTLSSSVTVTSSTW
PSQSITCNVAHPASSTKVDKKIEPKSCDKTHTCPPCPAPELLGGPSVF
LFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALH
NHYTQKSLSLSPG

Nucleotide sequence encoding the 9D9h1 heavy chain (SEQ ID NO: 55)

GAGATCCAGCTGCAGCAGAGCGGCCCCGTGCTGGTGAAGCCCGGCGCC
AGCGTGAAGATGAGCTGCAAGGCCAGCGGCTACACCTTCACCGACTAC
TACATGAACTGGGTGAAGCAGAGCCACGGCAAGAGCCTGGAGTGGATC
GGCGTGATCAACCCCTACAACGGCGACACCAGCTACAACCAGAAGTTC
AAGGGCAAGGCCACCCTGACCGTGGACAAGAGCAGCAGCACCGCCTAC
ATGGAGCTGAACAGCCTGACCAGCGAGGACAGCGCCGTGTACTACTGC
GCCAGATACTACGGCAGCTGGTTCGCCTACTGGGGCCAGGGCACCCTG
ATCACCGTGAGCACCGCCAAGACCACCGCCCCCAGCGTGTACCCCCTG
GCCCCCGTGTGCGGCGACACCACCGGCAGCAGCGTGACCCTGGGCTGC
CTGGTGAAGGGCTACTTCCCCGAGCCCGTGACCCTGACCTGGAACAGC
GGCAGCCTGAGCAGCGGCGTGCACACCTTCCCCGCCGTGCTGCAGAGC
GACCTGTACACCCTGAGCAGCAGCGTGACCGTGACCAGCAGCACCTGG
CCCAGCCAGAGCATCACCTGCAACGTGGCCCACCCCGCCAGCAGCACC
AAGGTGGACAAGAAGATCGAGCCCAAGAGCTGCGACAAGACCCACACC
TGCCCCCCCTGCCCCGCCCCCGAGCTGCTGGGCGGCCCCAGCGTGTTC
CTGTTCCCCCCCAAGCCCAAGGACACCCTGATGATCAGCAGAACCCCC
GAGGTGACCTGCGTGGTGGTGGACGTGAGCCACGAGGACCCCGAGGTG
AAGTTCAACTGGTACGTGGACGGCGTGGAGGTGCACAACGCCAAGACC
AAGCCCAGAGAGGAGCAGTACAACAGCACCTACAGAGTGGTGAGCGTG
CTGACCGTGCTGCACCAGGACTGGCTGAACGGCAAGGAGTACAAGTGC
AAGGTGAGCAACAAGGCCCTGCCCGCCCCCATCGAGAAGACCATCAGC
AAGGCCAAGGGCCAGCCCAGAGAGCCCCAGGTGTACACCCTGCCCCCC
AGCAGAGACGAGCTGACCAAGAACCAGGTGAGCCTGACCTGCCTGGTG
AAGGGCTTCTACCCCAGCGACATCGCCGTGGAGTGGGAGAGCAACGGC
CAGCCCGAGAACAACTACAAGACCACCCCCCCCGTGCTGGACAGCGAC
GGCAGCTTCTTCCTGTACAGCAAGCTGACCGTGGACAAGAGCAGATGG
CAGCAGGGCAACGTGTTCAGCTGCAGCGTGATGCACGAGGCCCTGCAC
AACCACTACACCCAGAAGAGCCTGAGCCTGAGCCCCGGCAAG

Amino acid sequence of the 9D9/FS1-67 heavy chain (SEQ ID NO: 56)

EIQLQQSGPVLVKPGASVKMSCKASGYTFTDYYMNWVKQSHGKSLEWI

Sequence listing

GVINPYNGDTSYNQKFKGKATLTVDKSSSTAYMELNSLTSEDSAVYYC

ARYYGSWFAYWGQGTLITVSTAKTTAPSVYPLAPVCGDTTGSSVTLGC

LVKGYFPEPVTLTWNSGSLSSGVHTFPAVLQSDLYTLSSSVTVTSSTW

PSQSITCNVAHPASSTKVDKKIEPKSCDKTHTCPPCPAPELLGGPSVF

LFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTIS

KAKGQPREPQVYTLPPSRDETDDGPVSLTCLVKGFYPSDIAVEWESTY

GPENNYKTTPPVLDSDGSFFLYSKLTVSYWRWYKGNVFSCSVMHEALH

NHYTQKSLSLSPG

Nucleotide sequence encoding the 9D9/FS1-67 heavy chain
(SEQ ID NO: 57)

GAGATCCAGCTGCAGCAGAGCGGCCCCGTGCTGGTGAAGCCCGGCGCC

AGCGTGAAGATGAGCTGCAAGGCCAGCGGCTACACCTTCACCGACTAC

TACATGAACTGGGTGAAGCAGAGCCACGGCAAGAGCCTGGAGTGGATC

GGCGTGATCAACCCCTACAACGGCGACACCAGCTACAACCAGAAGTTC

AAGGGCAAGGCCACCCTGACCGTGGACAAGAGCAGCAGCACCGCCTAC

ATGGAGCTGAACAGCCTGACCAGCGAGGACAGCGCCGTGTACTACTGC

GCCAGATACTACGGCAGCTGGTTCGCCTACTGGGGCCAGGGCACCCTG

ATCACCGTGAGCACCGCCAAGACCACCGCCCCCAGCGTGTACCCCCTG

GCCCCCGTGTGCGGCGACACCACCGGCAGCAGCGTGACCCTGGGCTGC

CTGGTGAAGGGCTACTTCCCCGAGCCCGTGACCCTGACCTGGAACAGC

GGCAGCCTGAGCAGCGGCGTGCACACCTTCCCCGCCGTGCTGCAGAGC

GACCTGTACACCCTGAGCAGCAGCGTGACCGTGACCAGCAGCACCTGG

CCCAGCCAGAGCATCACCTGCAACGTGGCCCACCCCGCCAGCAGCACC

AAGGTGGACAAGAAGATCGAGCCCAAGAGCTGCGACAAGACCCACACC

TGCCCCCCCTGCCCCGCCCCCGAGCTGCTGGGCGGCCCCAGCGTGTTC

CTGTTCCCCCCCAAGCCCAAGGACACCCTGATGATCAGCAGAACCCCC

GAGGTGACCTGCGTGGTGGTGGACGTGAGCCACGAGGACCCCGAGGTG

AAGTTCAACTGGTACGTGGACGGCGTGGAGGTGCACAACGCCAAGACC

AAGCCCAGAGAGGAGCAGTACAACAGCACCTACAGAGTGGTGAGCGTG

CTGACCGTGCTGCACCAGGACTGGCTGAACGGCAAGGAGTACAAGTGC

AAGGTGAGCAACAAGGCCCTGCCCGCCCCCATCGAGAAGACCATCAGC

AAGGCCAAGGGCCAGCCCAGAGAGCCCCAGGTGTACACCCTGCCCCCC

AGCAGAGACGAGACCGACGACGGCCCCGTGAGCCTGACCTGCCTGGTG

AAGGGCTTCTACCCCAGCGACATCGCCGTGGAGTGGGAGAGCACCTAC

GGCCCCGAGAACAACTACAAGACCACCCCCCCCGTGCTGGACAGCGAC

GGCAGCTTCTTCCTGTACAGCAAGCTGACCGTGAGCTACTGGAGATGG

TACAAGGGCAACGTGTTCAGCTGCAGCGTGATGCACGAGGCCCTGCAC

AACCACTACACCCAGAAGAGCCTGAGCCTGAGCCCCGGC

Amino acid sequence of the Ipilimumab light chain

| Sequence listing | |
|---|---|
| DIQMTQSPGTLSLSPGERATLSCRASQSVGSSYLAWYQQKPGQAPRLL<br>IYGAFSRATGIPDRFSGSGSGTDFTLTISRLEPEDFAVYYCQQYGSSP<br>WTFGQGTKVEIKRTVAAPSVFIFPPSDEQLKSGTASVVCLLNNFYPRE<br>AKVQWKVDNALQSGNSQESVTEQDSKDSTYSLSSTLTLSKADYEKHKV<br>YACEVTHQGLSSPVTKSFNRGEC | (SEQ ID NO: 58) |
| Nucleotide sequence encoding the Ipilimumab light chain<br>GACATCCAGATGACCCAGAGCCCCGGCACCCTGAGCCTGAGCCCCGGC<br>GAGAGAGCCACCCTGAGCTGCAGAGCCAGCCAGAGCGTGGGCAGCAGC<br>TACCTGGCCTGGTACCAGCAGAAGCCCGGCCAGGCCCCCAGACTGCTG<br>ATCTACGGCGCCTTCAGCAGAGCCACCGGCATCCCCGACAGATTCAGC<br>GGCAGCGGCAGCGGCACCGACTTCACCCTGACCATCAGCAGACTGGAG<br>CCCGAGGACTTCGCCGTGTACTACTGCCAGCAGTACGGCAGCAGCCCC<br>TGGACCTTCGGCCAGGGCACCAAGGTGGAGATCAAGAGAACCGTGGCC<br>GCCCCCAGCGTGTTCATCTTCCCCCCCAGCGACGAGCAGCTGAAGAGC<br>GGCACCGCCAGCGTGGTGTGCCTGCTGAACAACTTCTACCCCAGAGAG<br>GCCAAGGTGCAGTGGAAGGTGGACAACGCCCTGCAGAGCGGCAACAGC<br>CAGGAGAGCGTGACCGAGCAGGACAGCAAGGACAGCACCTACAGCCTG<br>AGCAGCACCCTGACCCTGAGCAAGGCCGACTACGAGAAGCACAAGGTG<br>TACGCCTGCGAGGTGACCCACCAGGGCCTGAGCAGCCCCGTGACCAAG<br>AGCTTCAACAGAGGCGAGTGC | (SEQ ID NO: 59) |
| Amino acid sequence of the Ipilimumab heavy chain<br>QVQLVESGGGVVQPGRSLRLSCAASGFTFSSYTMHWVRQAPGKGLEWV<br>TFISYDGNNKYYADSVKGRFTISRDNSKNTLYLQMNSLRAEDTAIYYC<br>ARTGWLGPFDYWGQGTLVTVSSASTKGPSVFPLAPSSKSTSGGTAALG<br>CLVKDYFPEPVTVSWNSGALTSGVHTFPAVLQSSGLYSLSSVVTVPSS<br>SLGTQTYICNVNHKPSNTKVDKKVERKCCVECPPCPAPPVAGPSVFLF<br>PPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKA<br>KGQPREPQVYTLPPSRDELTKNQVSLTCLVKGFYPSDIAVEWESNGQP<br>ENNYKTTPPVLDSDGSFFLYSKLTVDKSRWQQGNVFSCSVMHEALHNH<br>YTQKSLSLSPG | (SEQ ID NO: 60) |
| Nucleotide sequence encoding the Ipilimumab heavy chain<br>CAGGTGCAGCTGGTGGAGAGCGGCGGCGGCGTGGTGCAGCCCGGCAGA<br>AGCCTGAGACTGAGCTGCGCCGCCAGCGGCTTCACCTTCAGCAGCTAC<br>ACCATGCACTGGGTGAGACAGGCCCCCGGCAAGGGCCTGGAGTGGGTG<br>ACCTTCATCAGCTACGACGGCAACAACAAGTACTACGCCGACAGCGTG<br>AAGGGCAGATTCACCATCAGCAGAGACAACAGCAAGAACACCCTGTAC<br>CTGCAGATGAACAGCCTGAGAGCCGAGGACACCGCCATCTACTACTGC | (SEQ ID NO: 61) |

```
GCCAGAACCGGCTGGCTGGGCCCCTTCGACTACTGGGGCCAGGGCACC

CTGGTGACCGTGAGCAGCGCCAGCACCAAGGGCCCCAGCGTGTTCCCC

CTGGCCCCCAGCAGCAAGAGCACCAGCGGCGGCACCGCCGCCCTGGGC

TGCCTGGTGAAGGACTACTTCCCCGAGCCCGTGACCGTGAGCTGGAAC

AGCGGCGCCCTGACCAGCGGCGTGCACACCTTCCCCGCCGTGCTGCAG

AGCAGCGGCCTGTACAGCCTGAGCAGCGTGGTGACCGTGCCCAGCAGC

AGCCTGGGCACCCAGACCTACATCTGCAACGTGAACCACAAGCCCAGC

AACACCAAGGTGGACAAGAAGGTGGAGAGAAAGTGCTGCGTGGAGTGC

CCCCCCTGCCCCGCCCCCCCCGTGGCCGGCCCCAGCGTGTTCCTGTTC

CCCCCCAAGCCCAAGGACACCCTGATGATCAGCAGAACCCCCGAGGTG

ACCTGCGTGGTGGTGGACGTGAGCCACGAGGACCCCGAGGTGAAGTTC

AACTGGTACGTGGACGGCGTGGAGGTGCACAACGCCAAGACCAAGCCC

AGAGAGGAGCAGTACAACAGCACCTACAGAGTGGTGAGCGTGCTGACC

GTGCTGCACCAGGACTGGCTGAACGGCAAGGAGTACAAGTGCAAGGTG

AGCAACAAGGCCCTGCCCGCCCCCATCGAGAAGACCATCAGCAAGGCC

AAGGGCCAGCCCAGAGAGCCCCAGGTGTACACCCTGCCCCCCAGCAGA

GACGAGCTGACCAAGAACCAGGTGAGCCTGACCTGCCTGGTGAAGGGC

TTCTACCCCAGCGACATCGCCGTGGAGTGGGAGAGCAACGGCCAGCCC

GAGAACAACTACAAGACCACCCCCCCCGTGCTGGACAGCGACGGCAGC

TTCTTCCTGTACAGCAAGCTGACCGTGGACAAGAGCAGATGGCAGCAG

GGCAACGTGTTCAGCTGCAGCGTGATGCACGAGGCCCTGCACAACCAC

TACACCCAGAAGAGCCTGAGCCTGAGCCCCGGCAAG

Amino acid sequences of HuL2G7 CDRs
HuL2G7 CDR1
                                                    (SEQ ID NO: 62)
VH-GNWIE HuL2G7 CDR2
                                                    (SEQ ID NO: 63)
VH-EILPGSNTNYNEFKFKG HuL2G7 CDR3
                                                    (SEQ ID NO: 64)
VH-GGHYYGSSWDY HuL2G7 CDR1
                                                    (SEQ ID NO: 65)
VL-KASENVVTYVS HuL2G7 CDR2
                                                    (SEQ ID NO: 66)
VL-GASNRYT HuL2G7 CDR3
                                                    (SEQ ID NO: 67)
VL-GQGYSYPYT
```

The nucleic and amino acid sequence listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (93,257 bytes), which was created on Jan. 9, 2019, and is incorporated by reference herein.

REFERENCES

All documents mentioned in this specification are incorporated herein by reference in their entirety.

Amman et al (2005) "Aberrant Epidermal growth Factor Receptor Signaling and Enhanced Sensitivity to EGFR Inhibitors in Lung Cancer"; Cancer Res; 65; 226

Castoldi R. et al. (2013) "A novel bispecific EGFR/<et antibody blocks tumor-promoting phenotypic effects induced by resistance to EGFR inhibition and has potent antitumor activity"; Oncogene; 32, 5593-5601

Hudson L. G., Zeineldin R., Silberberg M., Stack M. S. (2009) "Activated epidermal growth factor receptor in ovarian cancer"; Cancer Treat Res; 149; 203-226

Furugaki K et al. (2014) "Loss of an EGFR-amplified chromosome 7 as a novel mechanism of acquired resistance to EGFR-TKIs in EGFR-mutated NSCLC cells"; Lung Cancer; 83; 44-50

Kawas L H, Yamamoto B J, Wright J W, Harding J W. Mimics of the Dimerisation Domain of Hepatocyte Growth Factor Exhibit Anti-Met and Anticancer Activity. J. Pharmacol. Exp. Ther. 2011; 339(2):509-18.

Kobayashi S et al. (2005) "EGFR mutation and resistance of non-small-cell lung cancer to gefitinib", N Engl J Med; 352: 786-792

Pao W., Miller V., Politi K., Riely G., Somwar R., Zakowski M., Kris M., Varmus H., (2005) "Acquired resistance of lung adenocarcinomas to gefitinib or erlotinib is associated with a second mutation in the EGFR kinase domain", PLoS Med, 2(3); e73

Kraman M, et al. Suppression of antitumor immunity by stromal cells expressing fibroblast activation protein-alpha. Science 2010; 330(6005): 827-830

Masuda H., Zhang D., Bartholomeusz C., Doihara H., Hortobagyi, G. N., Ueno, N. T. (2013) "Role of epidermal growth factor receptor in breast cancer"; Breast Cancer Res Treat; 136(2)

Naldini L., Tamagnone L., Vigna E. (1992) "Extracellular proteolytic cleavage by i=urokinase is required for activation of hepatocyte growth factor/scatter factor"; EMBO J, 11: 4825-4833

Organ S. L and Tsao M (2011) "An overview of the c-MET signalling pathway"; Ther Adv Med Oncol; 3 (1 Suppl); s7-s19

Pao W., Chmielecki J. (2010) "Rational, biologically based treatment of EGFR-mutant non-small-cell lung cancer"; Nature Reviews Cancer 10, 760-774

Pedersen M W, Jacobsen H J, Koefoed K, Hey A, Pyke C, Haurum J S, Kragh M. Sym004: A Novel Synergistic Anti-Epidermal Growth Factor Receptor Antibody Mixture with Superior Anticancer Efficacy. Cancer Res. 2010; 70(2):588-97.

Ramakrishnan M. S., Eswaraiah A., Crombet T., Piedra., Saurez G., Iyer H., Arvind A. S. (2009) "Nimotuzumab, a promising therapeutic monoclonal for treatment of tumors of epithelial origin", mAbs; 1 (1); 41-48

Saletti P., Molinari F., De Dosso S., Frattini M. (2015) "EGFR signalling in colorectal cancer: a clinical perspective"; Gastrointestinal Cancer: Targets and Therapy; 5; 21-38

Scambia G., Panici P. B., Ferrandina G., Battaglia F., Distefano M., D'Andrea G. (1994) "Significance of epidermal growth factor receptor expression in primary human endometrial cancer"; Int J Cancer; 1; 26-30

Shien K. et al. (2013) "Acquired Resistance to EGFR Inhibitors Is Associated with a Manifestation of Stem cell-like Properties in Cancer Cells"; Cancer Res; 73(10): 3051-3061

Smilek P. et al. (2012) "Epidermal growth factor receptor (EGFR) expression and mutations in the EGFR signalling pathway in correlation with anti-EGFR therapy in head and neck squamous cell carcinomas"; Neoplasma; 59(5); 508-15

Spano J. P., et al. (2005) "Epidermal growth factor receptor signalling in colorectal cancer: preclinical data and therapeutic perspectives"; Ann Oncol; 16(2); 189-194

Spiess C., Merchant M., Huang A., Zheng Z., Yang N., Peng J., Ellerman D., Shatz W., Reilly D., Yansura D., Scheer J. M. (2013) "Bispecific antibodies with natural architecture produced by co-culture of bacteria expressing two distinct half-antibodies", Nat Biotech 31 (8): 753

Stone A., Harrington K. Frakes M, Blank., Rajanna S (2014) "EGFR and c-Met inhibitors and effective in reducing tumorigenicity in cancer" J Carcinog Mutagen 5: 173

Taylor T. E., Furnari F. B., Cavanee W. K. (2012) "Targeting EGFR for treatment of glioblastoma: Molecular basis to overcome resistance"; Curr Cancer Drug Targets; 12(3); 197-209

Terashima M., Kitada K., Ochiai A., Ichikawa W., Kurahashi I., Sakuramoto S., Katai H., Sano T., Imamura H., Sasako M. (2012) "Impact of expression of Human Epidermal Growth Factor Receptors EGFR and ERBB2 on survival in Stage II/III gastric cancer", Clin Cancer Res; 18(21); 5992-6000

Troiani T., Martinelli E., Capasso A., Morgillo F., Orditura M (2012) "Targeting EGFR in pancreatic cancer treatment"; Curr Drug Targets; 13; 802-10

Uribe P. and Gonzalez S. (2011) "Epidermal growth factor receptor (EGFR) and squamous cell carcinoma of the skin: molecular bases for EGFR-targeted therapy"; Pathol Res Pract; 207(6); 337-42

Voigt M., Braig F., Gothel M., Schulte A., Lamszuz K., Bokemeyer C., Binder M. (2012) "Functional panitumumab and cetuximab epitopes", Neoplasia; 14 (11); 1023-1031

Zimmermann M., Zouhair A., Azria D., Ozsahin M. (2006) "The epidermal growth factor receptor (EGFR) in head and neck cancer; its role and treatment implications"; Radiat Oncol; 1; 11.

The invention claimed is:

1. An antibody molecule, comprising an EGFR antigen-binding site located in a CH3 domain of the antibody molecule, wherein the EGFR binding site comprises the amino acid sequences:

(i)
LDEGGP (SEQ ID NO: 1)
and

SHWRWYS; (SEQ ID NO: 3)

(ii)
LDEGGP (SEQ ID NO: 1)
and

SYWRWVK; (SEQ ID NO: 8)
or (iii)
TDDGP (SEQ ID NO: 13)
and

SYWRWYK; (SEQ ID NO: 14)

and wherein the amino acid sequence set forth in SEQ ID NO: 1 or 13 is located in the AB loop of the CH3 domain and the amino acid sequence set forth in SEQ ID NO: 3, 8, or 14 is located in the EF loop of the CH3 domain.

2. The antibody molecule according to claim 1, wherein the EGFR antigen-binding site further comprises the amino acid sequence TYG (SEQ ID NO: 2) in the CD loop of the CH3 domain.

3. The antibody molecule according to claim 2, wherein the antibody molecule comprises the CH3 domain set forth in SEQ ID NO: 4, 9, or 15.

4. The antibody molecule according to claim 1, wherein the antibody molecule further comprises a CH2 domain.

5. The antibody molecule according to claim 3, wherein the antibody molecule comprises the sequence set forth in SEQ ID NO: 6, 11, or 17.

6. The antibody molecule according to claim 1, wherein the antibody molecule comprises a CDR-based antigen-binding site.

7. The antibody molecule according to claim 1, wherein the antibody molecule is an immunoglobulin isotype.

8. The antibody molecule according to claim 6, wherein the CDR-based antigen-binding site binds to human HGF and comprises the complementarity determining regions (CDRs) of antibody rilotumumab set forth in SEQ ID NOs: 21-26 or the CDRs of antibody ficlatuzumab set forth in SEQ ID NOs: 31-36.

9. The antibody molecule according to claim 8, wherein the CDR-based antigen-binding site comprises the CDRs of antibody rilotumumab set forth in SEQ ID NOs: 21-26.

10. The antibody molecule according to claim 8, wherein the CDR-based antigen-binding site comprises the CDRs of antibody ficlatuzumab set forth in SEQ ID NOs: 31-36.

11. The antibody molecule according to claim 9, comprising the VH and VL domains of antibody rilotumumab set forth in SEQ ID NOs: 29 and 30.

12. The antibody molecule according to claim 10, comprising the VH and VL domains of antibody ficlatuzumab set forth in SEQ ID NOs: 39 and 40.

13. The antibody molecule according to claim 9, comprising the heavy chain sequence set forth in any one of SEQ ID NOs: 41, 43, or 45.

14. The antibody molecule according to claim 13, comprising the light chain sequence set forth in SEQ ID NO: 28.

15. The antibody molecule according to claim 10, comprising the heavy chain sequence set forth in any one of SEQ ID NOs: 42, 44, or 46.

16. The antibody molecule according to claim 15, comprising the light chain sequence set forth in SEQ ID NO: 38.

17. The antibody molecule according to claim 7, wherein the immunoglobulin isotype is immunoglobulin G.

18. The antibody molecule according to claim 17, wherein the immunoglobulin G is of IgG1, IgG2, IgG3, or IgG4 subclass.

19. The antibody molecule according to claim 3, wherein the CH3 domain comprises a lysine residue (K) at the immediate C-terminus of the sequence set forth in SEQ ID NO: 4, 9, or 15.

20. A nucleic acid encoding the antibody molecule according to claim 1.

* * * * *

UNITED STATES PATENT AND TRADEMARK OFFICE
CERTIFICATE OF CORRECTION

| | |
|---|---|
| PATENT NO. | : 11,629,193 B2 |
| APPLICATION NO. | : 16/319235 |
| DATED | : April 18, 2023 |
| INVENTOR(S) | : Tuna et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 458 days.

Signed and Sealed this
Twelfth Day of November, 2024

Katherine Kelly Vidal
*Director of the United States Patent and Trademark Office*